(12) United States Patent
Khodadoust et al.

(10) Patent No.: US 6,300,092 B1
(45) Date of Patent: Oct. 9, 2001

(54) METHODS OF USE OF A NOVEL LYSYL OXIDASE-RELATED PROTEIN

(75) Inventors: Mehran M. Khodadoust, Brookline; Kyle J. MacBeth, Boston, both of MA (US)

(73) Assignee: Millennium Pharmaceuticals Inc., Cambridge, MA (US)

( * ) Notice: Subject to any disclaimer, the term of this patent is extended or adjusted under 35 U.S.C. 154(b) by 0 days.

(21) Appl. No.: 09/448,076

(22) Filed: Nov. 23, 1999

Related U.S. Application Data

(63) Continuation-in-part of application No. 09/276,400, filed on Mar. 25, 1999, now Pat. No. 6,140,056.
(60) Provisional application No. 60/117,580, filed on Jan. 27, 1999.

(51) Int. Cl.[7] ............................... C12Q 1/52; C12Q 1/26; G01N 33/53; C12N 9/10; C12N 9/02
(52) U.S. Cl. ............................... 435/16; 435/25; 435/7.1; 435/193; 435/189
(58) Field of Search ............................... 435/16, 25, 7.1, 435/193, 189

(56) References Cited

PUBLICATIONS

Bedell–Hogan, Debra et al., "Oxidation, cross–linking, and insolubilization of recombinant tropoelastin by purified lysyl oxidase", *Journal of Biological Chemistry*, 268(14):10345–10350 (1993).

Chengzhen, R. et al "Reduced Lysyl Oxidase Messenger RNA Levels in Experimental and Human Prostrate Cancer" *Cancer Res.* 58:1285–1290, 1998.

Dangott, Lawrence J et al. "Cloning of the mRNA for the protein that crosslinks to the egg peptide speract". *Proc Natl. Acad. Sci USA*, 86:2128–2132 (1989).

Freeman, Mason et al. "An ancient, highly conserved family of cysteine–rich protein domains reveled by cloning type I and type II murine macrophage scavenger receptors", *Proc. Natl. Acad. Sci. USA*, 87:8810–8814 (1990).

GenBank® Accession No. AA269410 for Soares mouse 3NME12 5 *Mus Musculus* cDNA clone 6–Oxidase Precursor.

GenBank® Accession No. AA369741 for Pancreas tumor II *Homo sapiens* cDNA 5" end; Apr. 21, 1997.

GenBank® Accession No. AA522066 for Barstead mouse myotubes MPLRB6 *Mus musculus* cDNA clone IMAGE:903231 5' similar to SW.WC11_BOVIN P30205 Antigen WC1.1, Jul. 17, 1997.

GenBank® Accession No. AA530866 for NCI_CGAP_Pr21 *Homo sapiens* cDNA clone IMAGE:98478 3'; Aug. 20, 1997.

GenBank® Accession No. AA625414 for Soares_NhHMPu_S1 *Homo sapiens* cDNA clone IMAGE.1047259 af69b10.r1 Soares_NhHMPu_S1 *Homo sapiens* cDNA clone IMAGE:1047259 5'; Mar. 2, 1998.

GenBank® Accession No. AA673141 for Soares mouse mammary gland NbMMG *Mus musculus* cDNA clone IMAGE.820637 5'; Nov. 26, 1997.

GenBank® Accession No. for AA792234 for Soares mouse mammary gland NbMMG *Mus musculus* cDNA clone complete cds (Mouse); Feb. 9, 1998.

GenBank® Accession No. AA852888 for normal Human Trabecular Bone Cells *Homo sapiens* cDNA clone NHTHBCae01a08, May 12, 1999.

GenBank® Accession No. AA852889 for normal Human Trabecular Bone Cells *Homo sapiens* cDNA clone NHTBCae01a08; May 12, 1999.

GenBank® Accession No. AI082055 for Soares_senescent_fibroblasts_HbHSF *Homo sapiens* cDNA clone IMAGE:1678980 3' similar to TR Q08397 Q08397 Protein–Lysine Oxidase Homolog Precursor, contains TR1.t1 MSR1 repetitive element; Oct. 7, 1998.

GenBank® Accession No. AI148499 for Soares_placenta_8to9weeks_2NBHP8to9W *Homo sapiens* cDNA clone IMAGE:171462 3'; Oct. 27, 1998.

GenBank® Accession No. AI180353 for normalized rat spleen, Bento Soares Rattus sp. CDNA clone RSPCV22 3' end, Jan. 20, 1999.

GenBank® Accession No. AAI249780 for NCI_CGAP_Pan1 *Homo sapiens* cDNA clone IMAGE:2004863 3' similar to TR Q60997 Q60997 CRP–Ductin Precursor; contains TAR1 t1 TAR1 repetitive element, Feb. 3, 1999.

GenBank® Accession No. AI251754 for Soares_NFL_T_GBC_S1 *Homo sapiens* cDNA clone IMAGE:1854302 3'; Jan. 27, 1999.

GenBank® Accession No. AI262314 for NCI_CGAP_Co8 *Homo sapiens* cDNA clone IMAGE. 1870845 3', Jan. 28, 1999.

GenBank® Accession No. AI291580 for Soares_placenta_8to9weeks_2NbHP8to9W *Homo sapiens* cDNA clone IMAGE:1894465 3'; Nov. 30, 1998.

GenBank® Accession No. AI291685 for Soares_placenta_8to9weeks_2NbHP8to9W *Homo sapiens* cDNA clone IMAGE:1894522 3'; Jan. 29, 1999.

(List continued on next page.)

*Primary Examiner*—Rebecca E. Prouty
(74) *Attorney, Agent, or Firm*—Lahive & Cockfield, LLP; Amy E. Mandragouras; Debra J. Milasincic

(57) ABSTRACT

Novel Lor-2 polypeptides, proteins, and nucleic acid molecules are disclosed. In addition to isolated, full-length Lor-2 proteins, the invention further provides isolated Lor-2 fusion proteins, antigenic peptides and anti-Lor-2 antibodies. The invention also provides Lor-2 nucleic acid molecules, recombinant expression vectors containing a nucleic acid molecule of the invention, host cells into which the expression vectors have been introduced and non-human transgenic animals in which a Lor-2 gene has been introduced or disrupted. Diagnostic, screening and therapeutic methods utilizing compositions of the invention are also provided.

17 Claims, 14 Drawing Sheets

PUBLICATIONS

GenBank® Accession No. AAB49697 for lysyl oxidase–related protein, Mar. 16, 1997.

GenBank® Accession No. AAC79085 for lysyl oxidase homolog; Apr. 14, 1999.

GenBank® Accession No. AAC83205 for lysyl oxidase–related protein 2; Mar. 15, 1999.

GenBank® Accession No. AAC95338 for LOR2 protein. Mar. 15, 1999.

GenBank® Accession No. AC003061 for Mouse chromosome 6 BAC Clone b245c12, complete sequence, Dec. 8, 1998.

GenBank® Accession No. AC005033 for *Homo sapiens* clone NH0140K04, complete sequence, Jan. 14, 1999.

GenBank® Accession No. AC005041 for *Homo sapiens* clone NH0523H20, complete sequence, Mar. 24, 1999.

GenBank® Accession No. AF053368 for *Mus musculus* lysyl oxidase–related protein 2 (Lor2) mRNA, complete cds Mar. 15, 1999.

GenBank® Accession No. AF084363 for *Mus musculus* D6MM5e protein (D6Mm5e) and DOK protein (Dok) genes, complete cds, and LOR2 protein (Lor2) gene, partial cds; Mar. 15, 1999.

GenBank® Accession No. AF103901 for *Perca flavescens* lysyl oxidase homolog (PLO1) mRNA, partial cds, Apr. 14, 1999.

GenBank® Accession No. HSU89942 for Human Lysyl oxidase–related protein (WS9–14) mRNA, complete cds; Mar. 16, 1997.

Hamalainen, Eija–Riitta et al. "Molecular cloning of human lysyl oxidase and assignment of the gene to chromosome 5a23.3–31.2", *Genomics*, 11:508–516 (1991).

Jang,Wonhee et al., "Comparative sequence of human and mouse BAC clones the mnd2 region of Chromosome 2p13", *Cold Spring Harbor Laboratory Press*, 9:53–61 (1999).

Jourdan–LeSaux, Claude et al, "The LOXL2 gene encodes a new lysyl oxidase–like protein and is expressed at high levels in reproductive tissues", *Journal of Biological Company*, 274(18):12939–12944 (1999).

Kagan, H.M. et al., "Catalytic properties and structural components of lysyl oxidase" from Ciba Foundation Symposium *The molecular biology and pathology of elastic tissues. Ciba Foundation Symposium 192*, pp 100–121 (1995).

Kenyon, Kaylene et al, "A novel human cDNA with a predicted protein similar to lysyl oxidase maps to chromosome 15q24–q25", *Journal of Biological Chemistry*; 268(5):18435–18437 (1993).

Kim, Youngho et al, "Coexpression of the lysyl oxidase–like gene (LOXL) and the gene encoding type II procollagen in induced liver fibrosis", *Journal of Cellular Biochemistry*, 72:181–188 (1999).

Kim, Youngho et al., "A new gene with sequence and structural similarity to the gene encoding human lysyl oxidase", *Journal of Biological Chemistry*, 270(13):7176–7182 (1995).

Saito, Hiroshi et al., "Regulation of a novel gene encoding a lysyl oxidase–related protein in cellular adhesion and senescence", *Journal of Biological Chemistry*, 272(13):8157–8160 (1997).

Somers, Shaw S. et al., "Comparison of transforming growth factor β and a human tumour–derived suppressor factor", *Cancer Immunology Immunotherapy*, pp 217–222 (1991).

Trackman, Philip C et al., "Cloning of rat aorta lysyl oxidase cDNA: complete codons and predicted amino acid sequence", *Biochemistry*,29:4863–4870 (1990).

CGTCCGCCAC GCGTCCGGAC TAGTTCTAGA TCGCGAGCGG CCGCCCTTTT
TTTTTTTTTT TTGGAAGTCC TAGGACTGAT CTCCAGGACC AGCACTCTTC
TCCCAGCCCT TAGGGTCCTG CTCGGCAAG GCCTTCCCTG CC ATG CGA
CCT GTC AGT GTC TGG CAG TGG AGC CCC TGG GGG CTG CTG CTG
TGC CTG CTG TGC AGT TCG TGC TTG GGG TCT CCG TCC CCT TCC
ACG GGC CCT GAG AAG AAG GCC GGG AGC CAG GGG CTT CGG TTC
CGG CTG GCT GGC TTC CCC AGG AAG CCC TAC GAG GGC CGC GTG
GAG ATA CAG CGA GCT GGT GAA TGG GGC ACC ATC TGC GAT GAT
GAC TTC ACG CTG CAG GCT GCC CAC ATC CTC TGC CGG GAG CTG
GGC TTC ACA GAG GCC ACA GGC TGG ACC CAC AGT GCC AAA TAT
GGC CCT GGA ACA GGC CGC ATC TGG CTG GAC AAC TTG AGC TGC
AGT GGG ACC GAG CAG AGT GTG ACT GAA TGT GCC TCC CGG GGC
TGG GGG AAC AGT GAC TGT ACG CAC GAT GAG GAT GCT GGG GTC
ATC TGC AAA GAC CAG CGC CTC CCT GGC TTC TCG GAC TCC AAT
GTC ATT GAG GTA GAG CAT CAC CTG CAA GTG GAG GAG GTG CGA
ATT CGA CCC GCC GTT GGG TGG GGC AGA CGA CCC CTG CCC GTG
ACG GAG GGG CTG GTG GAA GTC AGG CTT CCT GAC GGC TGG TCG
CAA GTG TGC GAC AAA GGC TGG AGC GCC CAC AAC AGC CAC GTG
GTC TGC GGG ATG CTG GGC TTC CCC AGC GAA AAG AGG GTC AAC
GCG GCC TTC TAC AGG CTG CTA GCC CAA CGG CAG CAA CAC TCC
TTT GGT CTG CAT GGG GTG GCG TGC GTG GGC ACG GAG GCC CAC
CTC TCC CTC TGT TCC CTG GAG TTC TAT CGT GCC AAT GAC ACC
GCC AGG TGC CCT GGG GGG GGC CCT GCA GTG GTG AGC TGT GTG
CCA GGC CCT GTC TAC GCG GCA TCC AGT GGC CAG AAG AAG CAA
CAA CAG TCG AAG CCT CAG GGG GAG GCC CGT GTC CGT CTA AAG
GGC GGC GCC CAC CCT GGA GAG GGC CGG GTA GAA GTC CTG AAG
GCC AGC ACA TGG GGC ACA GTC TGT GAC CGC AAG TGG GAC CTG
CAT GCA GCC AGC GTG GTG TGT CGG AGC TGG GCT TCG GGA GT
GCT CGA GAA GCT CTG AGT GGC GCT CGC ATG GGG CAG GGC ATG
GGT GCT ATC CAC CTG AGT GAA GTT CGC TGC TCT GGA CAG GAG
CTC TCC CTC TGG AAG TGC CCC ACA AGA ACA TCA CAG CTG AG
GAT TGT TCA CAT AGC CAG GAT GCC GGG GTC CGG TGC AAC CTA
CCT TAC ACT GGG GCA GAG ACC AGG ATC GAC TCA GTG GGC
CGC AGC AAC ATG AGG GGC GAG TCG AGG TGC AAA TAG GGG GA

*FIG. 1A*

```
CCT GGG CCC CTT CGC TGG GGC CTC ATC TGT GGG GAT GAC TGG
GGG ACC CTG GAG GCC ATG GTG GCC TGT AGG CAA CTG GGT CTG
GGC TAC GCC AAC CAC GGC CTG CAG GAG ACC TGG TAC TGG GAC
TCT GGG AAT ATA ACA GAG GTG GTG ATG AGT GGA GTG CGC TGC
ACA GGG ACT GAG CTG TCC CTG GAT CAG TGT GCC CAT CAT GGC
ACC CAC ATC ACC TGC AAG AGG ACA GGG ACC CGC TTC ACT GCT
GGA GTC ATC TGT TCT GAG ACT GCA TCA GAT CTG TTG CTG CAC
TCA GCA CTG GTG CAG GAG ACC GCC TAC ATC GAA GAC GGG CCC
CTG CAT ATG TTG TAC TGT GCT GCG GAA GAG AAC TGC CTG GCC
AGC TCA GCC CGC TCA GCC AAC TGG CCC TAT GGT CAC CGG CGT
CTG CTC CGA TTC TCC TCC CAG ATC CAC AAC CTG GGA CGA GCT
GAC TTC AGG CCC AAG GCT GGG CGC CAC TCC TGG GTG TGG CAC
GAG TGC CAT GGG CAT TAC CAC AGC ATG GAC ATC TTC ACT CAC
TAT GAT ATC CTC ACC CCA AAT GGC ACC AAG GTG GCT GAG GGC
CAC AAA GCT AGT TTC TGT CTC GAA GAC ACT GAG TGT CAG GAG
GAT GTC TCC AAG CGG TAT GAG TGT GCC AAC TTT GGA GAG CAA
GGC ATC ACT GTG GGT TGC TGG GAT CTC TAC CGG CAT GAC ATT
GAC TGT CAG TGG ATT GAC ATC ACG GAT GTG AAG CCA GGA AAC
TAC ATT CTC CAG GTT GTC ATC AAC CCA AAC TTT GAA GTA GCA
GAG AGT GAC TTT ACC AAC AAT GCA ATG AAA TGT AAC TGC AAA
TAT GAT GGA CAT AGA ATC TGG GTG CAC AAC TGC CAC ATT GGT
GAT GCC TTC AGT GAA GAG GCC AAC AGG AGG TTT GAA CGC TAC
CCT GGC CAG ACC AGC AAC CAG ATT ATC TAAGTGCCAC TGCCCTCTGC
AAACCACCAC TGGCCCCTAA TGGCAGGGGT CTGAGGCTGC CATTACCTCA
GGAGCTTACC AAGAAACCCA TGTCAGCAAC CGCACTCATC AGACCATGCA
CTATGGATGT GGAACTGTCA AGCAGAAGTT TTCACCCTCC TTCAGAGGCC
AGCTGTCAGT ATCTGTAGCC AAGCATGGGA ATCTTTGCTC CCAGGCCCAG
CACCGAGCAG AACAGACCAG AGCCCACCAC ACCACAAAGA GCAGCACCTG
ACTAACTGCC CACAAAAGAT GGCAGCAGCT CATTTCTTT AATAGGAGGT
CAGGATGGTC AGCTCCAGTA TCTCCCCTAA GTTTAGGGGG ATACAGCTTT
ACCTCTAGCC TTTTGGTGGG GGAAAAGATC CAGCCCTCCC ACCTCATTTT
TTACTATAAT ATGTTGCTAG GTATAATTTT ATTTTATATA AAAGTGTTT
CTGTGATTCT TCAGAAAAAA AAAAAAAAAA AAAAAAAAAA AAAAAAAA
```

*FIG. 1B*

```
ATG CGA CCT GTC AGT GTC TGG CAG TGG AGC CCC TGG GGG CTG CTG
CTG TGC CTG CTG TGC AGT TCG TGC TTG GGG TCT CCG TCC CCT TCC
ACG GGC CCT GAG AAG AAG GCC GGA GCC AGG GGC TTC GGT TCC GGC
TGG CTG GCT TCC CCA GGA AGC CCT ACG AGG GCC GCG TGG AGA TAC
AGC GAG CTG GTG AAT GGG GCA CCA TCT GCG ATG ATG ACT TCA CGC
TGC AGG CTG CCC ACA TCC TCT GCG GGA GCT GGG CTT CAC AGA GGC
CAC AGG CTG GAC CCA CAG TGC CAA ATA TGG CCC TGG AAC AGG CCG
CAT CTG GCT GGA CAA CTT GAG CTG CAG TGG GAC CGA GCA GAG TGT
GAC TGA ATG TGC CTC CCG GGG CTG GGG GAA CAG TGA CTG TAC CAC
GAT GAG GAT GCT GGG GTC ATC TGC AAA GAC CAG CGC CTC CCT GGC
TTC TCG GAC TCC AAT GTC ATT GAG GTA GAG CAT CAC CTG CAA GTG
GAG GAG GTG CGA ATT CGA CCC GCC GTT GGG TGG GGC AGA CGA CCC
CTG CCC GTG ACG GAG GGG CTG GTG GAA GTC AGG CTT CCT GAC GGC
TGG TCG CAA GTG TGC GAC AAA GGC TGG AGC GCC CAC AAC AGC CAC
GTG GTC TGC GGG ATG CTG GGC TTC CCC AGC GAA AAG AGG GTC AAC
GCG GCC TTC TAC AGG CTG CTA GCC CAA CGG CAG CAA CAC TCC TTT
GGT CTG CAT GGG GTG GCG TGC GTG GGC ACG GAG GCC CAC CTC TCC
CTC TGT TCC CTG GAG TTC TAT CGT GCC AAT GAC ACC GCC AGG TGC
CCT GGG GGG GGC CCT GCA GTG GTG AGC TGT GTG CCA GGC CCT GTC
TAC GCG GCA TCC AGT GGC CAG AAG AAG CAA CAA CAG TCG AAG CCT
CAG GGG GAG GCC CGT GTC CGT CTA AAG GGC GGC GCC CAC CCT GGA
GAG GGC CGG GTA GAA GTC CTG AAG GCC AGC ACA TGG GGC ACA GTC
TGT GAC CGC AAG TGG GAC CTG CAT GCA GCC AGC GTG GTG TGT CGG
GAG CTG GGC TTC GGG AGT GCT CGA GAA GCT CTG AGT GGC GCT CGC
ATG GGG CAG GGC ATG GGT GCT ATC CAC CTG AGT GAA GTT CGC TGC
TCT GGA CAG GAG CTC TCC CTC TGG AAG TGC CCC ACA AGA ACA TC
ACA GCT GAG GAT TGT TCA CAT AGC CAG GAT GCC GGG GTC CGG TGC
AAC CTA CCT TAC ACT GGG GCA GAG ACC AGG ATC CGA CTC AGT GGG
GGC CGC AGC CAA CAT GAG GGG CGA GTC GAG GTG CAA ATA GGG GA
CCT GGG CCC CTT CGC TGG GGC CTC ATC TGT GGG GAT GAC TGG GGG
ACC CTG GAG GCC ATG GTG GCC TGT AGG CAA CTG GGT CTG GCT TAC
GCC AAC CAC GGC CTG CAG GAG ACC TGG TAC TGG GAC TCT GGG AAT
```

*FIG. 2A*

```
ATA ACA GAG GTG GTG ATG AGT GGA GTG CGC TGC ACA GGG ACT GAG
CTG TCC CTG GAT CAG TGT GCC CAT CAT GGC ACC CAC ATC ACC TGC
AAG AGG ACA GGG ACC CGC TTC ACT GCT GGA GTC ATC TGT TCT GAG
ACT GCA TCA GAT CTG TTG CTG CAC TCA GCA CTG GTG CAG GAG ACC
GCC TAC ATC GAA GAC CGG CCC CTG CAT ATG TTG TAC TGT GCT GCG
GAA GAG AAC TGC CTG GCC AGC TCA GCC CGC TCA GCC AAC TGG CCC
TAT GGT CAC CGG CGT CTG CTC CGA TTC TCC TCC CAG ATC CAC AAC
CTG GGA CGA GCT GAC TTC AGG CCC AAG GCT GGG CGC CAC TCC TGG
GTG TGG CAC GAG TGC CAT GGG CAT TAC CAC AGC ATG GAC ATC TTC
ACT CAC TAT GAT ATC CTC ACC CCA AAT GGC ACC AAG GTG GCT GAG
GGC CAC AAA GCT AGT TTC TGT CTC GAA GAC ACT GAG TGT CAG GAG
GAT GTC TCC AAG CGG TAT GAG TGT GCC AAC TTT GGA GAG CAA GGC
ATC ACT GTG GGT TGC TGG GAT CTC TAC CGG CAT GAC ATT GAC TGT
CAG TGG ATT GAC ATC ACG GAT GTG AAG CCA GGA AAC TAC ATT CTC
CAG GTT GTC ATC AAC CCA AAC TTT GAA GTA GCA GAG AGT GAC TTT
ACC AAC AAT GCA ATG AAA TGT AAC TGC AAA TAT GAT GGA CAT AGA
ATC TGG GTG CAC AAC TGC CAC ATT GGT GAT GCC TTC AGT GAA GAG
GCC AAC AGG AGG TTT GAA CGC TAC CCT GGC CAG ACC AGC AAC CAG
ATT ATC TAA
```

*FIG. 2B*

```
MRPVSVWQWS PWGLLLCLLC SSCLGSPSPS TGPEKKAGSQ GLRFRLAGFP
RKPYEGRVEI QRAGEWGTIC DDDFTLQAAH ILCRELGFTE ATGWTHSAKY
GPGTGRIWLD NLSCSGTEQS VTECASRGWG NSDCTHDEDA GVICKDQRLP
GFSDSNVIEV EHHLQVEEVR IRPAVGWGRR PLPVTEGLVE VRLPDGWSQV
CDKGWSAHNS HVVCGMLGFP SEKRVNAAFY RLLAQRQQHS FGLHGVACVG
TEAHLSLCSL EFYRANDTAR CPGGPAVVS CVPGPVYAAS SGQKKQQQSK
PQGEARVRLK GGAHPGEGRV EVLKASTWGT VCDRKWDLHA ASVVCRELGF
GSAREALSGA RMGQGMGAIH LSEVRCSGQE LSLWKCPHKN ITAEDCSHSQ
DAGVRCNLPY TGAETRIRLS GGRSQHEGRV EVQIGGPGPL RWGLICGDDW
GTLEAMVACR QLGLGYANHG LQETWYWDSG NITEVVMSGV RCTGTELSLD
QCAHHGTHIT CKRTGTRFTA GVICSETASD LLLHSALVQE TAYIEDRPLH
MLYCAAEENC LASSARSANW PYGHRRLLRF SSQIHNLGRA DFRPKAGRHS
WVWHECHGHY HSMDIFTHYD ILTPNGTKVA EGHKASFCLE DTECQEDVSK
RYECANFGEQ GITVGCWDLY RHDIDCQWID ITDVKPGNYI LQVVINPNFE
VAESDFTNNA MKCNCKYDGH RIWVHNCHIG DAFSEEANRR FERYPGQTSN
QII
```

```
        1                                                              60
LOX     MRFA------------WTVLLGPLQ-----------LCALVHCAPPAAGQQQP---------
huLOL   MALA------------RGSRQLGALV---------WGACLCVLVH------GQQAQ------
huLor   MERPLCSHLCSCLAMLALLSPLSLAQYDSWPHYPEYFQQPAPEYHQPQAPANVAKIQLRL
muLor-2 M-RAVSVWYCCPWGLLLLHCL-C-----------SFSVGSPSPS-ISPEKKVGSQLRFRL
huLor-2 M-RPVSVWQWSPWGLLL--CLLC-----------SSCLGSPSPS-TGPEKKAGSQGLRFRL 61                                                             120
LOX     ---PREPPAAPGAWRQQIQWENN-GQVFSL-------LSLGSQY-----------------
huLOL   ---P-GQGSDPARWRQLIQWENN-GQVYSL-------LNSGSEYVPA-------GPQRSESSSR
huLor   AGQKRKHSEGRVEVYYDGQWGTVCDDDFSIHAAHVVCRELGYVEAKSWTASSSYGKGEGP
muLor-2 AGFPRKPYEGRVEIQRAGEWGTICDDDFTLQAAHVLCRELGFTEATGWTHSAKYGPGTGR
huLor-2 AGFPRKPYEGRVEIQRAGEWGTICDDDFTLQAAHILCRELGFTEATGWTHSAKYGPGTGR 121                                                            180
LOX     -----------------QPQRRRDPGAA--------VPG----AANASAQQPRTP
huLOL   -----------GAPQAQQRRSHGSPRRRQAPSLP-------LPG-RVGSDTVRGQARHP
huLor   VLLA---------IWLDNLHCTGNEATLAACTSNGWGVTDCKHTEDVGVVCSDKRIPGFKFDNSLINQIENLN
muLor-2 IWLDNLSCRGTEGSVTECASRGWGNSDCTHDEDAGVICKDQRLPGF--SDSNVIEVEH-Q
huLor-2 IWLDNLSCSGTEQSVTECASRGWGNSDCTHDEDAGVICKDQRLPGF--SDSNVIEVEH-H 181                                                            240
LOX     ILL--IRD----N-----------RTAAG------RTRTAGSSGVTAG-----------
huLOL   FGFGQVPD----NWREVAVGDSTGMALARTSVS------QQRHGGSASSVSAS-AFAST-
huLor   IQVEDIRIRAILSTYRKRTPVMEGYVEVKEGKTWKQICDKHWTAKNSRVVCGMFGFPGER
muLor-2 LQVEEVRLRPAVEWGRRPLPVTEGLVEVRLPEGWSQVCDKGWSAHNSHVVCGMLGFPGEK
huLor-2 LQVEEVRIRPAVGWGRRPLPVTEGLVEVRLPDGWSQVCDKGWSAHNSHVVCGMLGFPSEK
```

FIG. 5B

```
           241
LOX        ------------RP-RPTARHWF------------------------------QAGY-----------STSRA     300
huLOL      ------------YRQ-QPSYPQQFPY------------------------------PQAPF-----VSQYENYDPASRT
huLor      TYNTKVYKMFASRRKQRYWPFSMDCTGTEAHISSCKLGPQVSLDPMKNVTCENGLPAVVS
muLor-2    RVNMAFYRMLAQKKQHSFGLHSVACVGTEAHLSLCSLE---FYRANDTTRCSGGNPAVVS
huLor-2    RVNAAFYRLLAQRQQHSFGLHGVACVGTEAHLSLCSLE---FYRANDTARCPGGGPAVVS 301                                                                              360
LOX        ------------------------REAGPSR----AENQTAPGEVPAL-----------SNLRP
huLOL      YDQGFVY------------------YRPAGGGV----GAGAAVASAGVI-----------YPYQP
huLor      CVPGQVFSPDGPSRFRKAYKPE-QPLVRLRGGAYIGEGRVEVLKNGEWGTVCDDKWDLVS
muLor-2    CVLGPLYATFTGQKKQQHSKPQGEARVRLKGGAHQEGRVEVLKAGTWGTVCDRKWDLQA
huLor-2    CVPGPVYAASSGQKKQQQSKPQGEARVRLKGGAHPGEGRVEVLKASTWGTVCDRKWDLHA 361                                                                              420
LOX        ------------------------RVDGMVGDD---------------------PYNP-----
huLOL      PS--------------------------------------------------------------
huLor      RA------RYEEYGGGEELPEYPPQG-----FYPAPERPYVPPPPPPD
muLor-2    ASVVCRELGFGSAKEAVTGSRLGQGIGPIHLNEIQCTGNEKSIIDCKFNA-ESQGCNHEE
huLor-2    ASVVCPELGFGFGTAREALSGARMGQGMGAIHLSEVRCSGQEPSLWRCPSKNITAEDCSHSQ
           ASVVCRELGFGSAREALSGARMGQGMGAIHLSEVRCSGQELSLWKCPHKNITAEDCSHSQ 421                                                                              480
LOX        -------YK------YSDDNPYYNYYDTYERPRPG-------------GRYRP--------GYGTG
huLOL      GLDRRYSHSLYSEGTPGFE---QAYPDPGPEAAQAHGGDPRLGWYPPYANP--PPEAYGPP
huLor      DAGVRCNTP-AMGLQKKLRLNGGRNPYEGRVEVLVERNGSLVWGMVCGQNWGIVEAMVVC
muLor-2    DAGVRCNLP-YTGVETKIRLSGGRSRYEGRVEVQIGIPGHLRWGLICGDDWGTLEAMVAC
huLor-2    DAGVRCNLP-YTGAETRIRLSGGRSQHEGRVEVQIGGPGPLRWGLICGDDWGTLEAMVAC
```

FIG. 5C

```
          481                                                           540
LOX       --------Y-----------------------FQ----------------------------Y
huLOL     RALEPPY-----------------LPVRSSDTPPPGGE------RNGAQQGRLSVGSVY
huLor     RQLGLGFASNAFQETWYWHGDVNSNKVVMSGVKCSGTELSLAHCRHDGEDVACPQGGVQY
muLor-2   RQLGLGYANHGLQETWYWDSG-NVTEVMSGVRCTGSELSLNQCAHHSSHITCKKTGTRF
huLor-2   RQLGLGYANHGLQETWYWDSG-NITEVMSGVRCTGTELSLDQCAHHGTHITCKRTGTRF 541                                                           600
LOX       --------GLPDLVADPYYIQASTYVQKMSMYNLRCAAEENCLASTAYRADVRDYDHRVL
huLOL     RPNQN-GRGLPDLVPDPNYVQASTYVQRAHLYSLRCAAEEKCLASTAYAPEATDYDVRVL
huLor     GAGVACSETAPDLVLNAEMVQQTTYLEDRPMFMLQCAMEENCLSASAAQTD-PTTGYRRL
muLor-2   TAGVICSETASDLLLHSALVQETAYIEDRPLHMLYCAAEENCLASSARSAN-WPYGHRRL
huLor-2   TAGVICSETASDLLLHSALVQETAYIEDRPLHMLYCAAEENCLASSARSAN-WPYGHRRL 601                                                           660
LOX       LRFPQRVKNQGTSDFLPSRPRYSWEWHSCHQHYHSMDEFSHYDLLDANTQRRVAEGHKAS
huLOL     LRFPQRVKNQGTADFLPNRPRHTWEWHSCHQHYHSMDEFSHYDLLDAATGKKVAEGHKAS
huLor     LRFSSQIHNNGQSDFRPKNGRHAWIWHDCHRHYHSMEVFTHYDLLNLN-GTKVAEGHKAS
muLor-2   LRFSSQIHNLGRADFRPKAGRHSWVHECHGHYHSMDIFTHYDILTPN-GTKVAEGHKAS
huLor-2   LRFSSQIHNLGRADFRPKAGRHSWVHECHGHYHSMDIFTHYDILTPN-GTKVAEGHKAS 661                                                           720
LOX       FCLEDTSCDYGYHRRFACTAHT-QGLSPGCYDTYGADIDCQWIDITDVKPGNYILKVSVN
huLOL     FCLEDSTCDFGNLKRYACTSHT-QGLSPGCYDTYNADIDCQWIDITDVQPGNYILKVHVN
huLor     FCLEDTECECGDIQKNYECANFGDQGITMGCWDMYRHDIDCQWVDITDVPPGDYLFQVVIN
muLor-2   FCLEDTECQEDVSKRYECANFGEQGITVGCWDLYRHDIDCQWIDITDVKPGNYILQVVIN
huLor-2   FCLEDTECQEDVSKRYECANFGEQGITVGCWDLYRHDIDCQWIDITDVKPGNYILQVVIN
```

FIG. 5D

```
       721                                                            779
LOX    PSYLVPESDYTNNVVRCDIRYTGHHAYASGCTI-------------------------SPY
huLOL  PKYIVLESDFTNNVVRCNIHYTGRYVSATNCKI------------------------VQS
huLor  PNFEVAESDYSNNIMKCRSRYDGHRIWMYNCHIGGSFSEETEKKFEHFSGLLNNQLSPQ
muLor-2 PNFEVAESDFTNNAMKCNCKYDGHRIWVHNCHIGDAFSEEANRRFERYPGQTSNQIV--
huLor-2 PNFEVAESDFTNNAMKCNCKYDGHRIWVHNCHIGDAFSEEANRRFERYPGQTSNQII--
```

METHODS OF USE OF A NOVEL LYSYL OXIDASE-RELATED PROTEIN

RELATED APPLICATIONS

The present application is a continuation-in-part application of prior-filed U.S. patent application Ser. No. 09/276,400 entitled "Novel MSP-18 Protein and Nucleic Acid Molecules and Uses Therefor", filed Mar. 25, 1999 now U.S. Pat. No. 6,140,056, issued Oct. 31, 2000, which claims the benefit of prior-filed U.S. Provisional Patent Application Ser. No. 60/117,580 entitled "Novel MSP-18 Protein and Nucleic Acid Molecules and Uses Therefor", filed Jan. 27, 1999. The content of the above-referenced patent applications is incorporated herein by this reference in its entirety.

BACKGROUND OF THE INVENTION

Lysyl oxidase ("LOX") is an extracellular copper enzyme that initiates the crosslinking of collagens and elastin by catalyzing oxidative deamination of the $\epsilon$-amino group in certain lysine and hydroxylysine residues of collagens and lysine residues of elastin (Smith-Mungo and Kagan (1998) *Matrix Biol.* 16:387–398 and Kaman in *Biology of Extracellular Matrix,* ed. Mecham (1986) *Academic Press* pp. 321–389). Lysyl oxidase has been shown to be important in a variety of cellular and physiologic processes including biogenesis of connective tissue matrices and bone resorption. A deficiency in lysyl oxidase activity is found in two X-linked, recessively inherited connective tissue disorders, the type IX variant of the Ehlers-Danlos syndrome and the Menkes syndrome, and in the X-linked, recessively inherited mottled series of allelic mutant mice (all characterized by abnormalities in copper metabolism). (Byers et al. (1980) *New Engl. J. Med.* 303:61–65; Royce et al. (1980) *Biochemistry J.* 192:579–586; Kuivaniemi et al. (1982) *J. Clin. Invest.* 69:730–733; Kuivaniemi et al. (1985) *Amer. J. Human. Genet.* 37:798–808; Peltonen et al. (1983) *Biochemistry* 22:6156–6163; Rowe et al. (1977) *J. Biol. Chem.* 252:939–942; Starcher et al. (1977) *Biochem. Biophys. Res. Commun.* 78:706–712; Danks in *The Metabolic Basis of inherited Disease",* eds. Stanbury et al. *(1983),* McGraw-Hill pp. 1251–1268). Increased lysyl oxidase activity has been associated with fibrotic disorders such as atherosclerosis, hypertension, and liver and pulmonary fibrosis. (Kagan, supra).

More recently there have been identified proteins having structural and/or functional similarities to lysyl oxidase. For example, a lysyl oxidase-like protein, referred to herein as "LOL", was identified from a human skin fibroblast cDNA library that contains extensive homology to several coding domains within the human lysyl oxidase mRNA which is believed to be involved in collagen maturation. (Kenyon et al. (1993) *J. Biol. Chem.* 268:18435–18437 and Kim et al. (1995) *J. Biol. Chem.* 270:7176–7182). Recent cloning and analysis of the mouse LOL gene (Kim et al. (1999) *J. Cell Biochem.* 72:181–188) demonstrated that steady state levels of LOL mRNA and type III procollagen mRNA increased coincidentally early in the development of liver fibrosis. In contrast, steady state levels of lysyl oxidase mRNA increased throughout the onset of hepatic fibrosis and appeared in parallel with the increased steady state levels of pro-alpha (I) collagen mRNA, suggesting that the LOL protein is involved in the development of lysine-derived cross-links in collagenous substrates. Moreover, the substrate specificity of the LOL protein may be different to that of lysyl oxidase and this difference may be collagen-type specific.

Likewise, a protein referred to herein as lysyl-oxidase related protein ("Lor") has been identified which inhibits many of the structural features of lysyl oxidase and is overexpressed in senescent fibroblasts and is believed to play a role in age-associated changes in extracellular proteins. (Saito et al. (1997) *J. Biol. Chem.* 272:8157–8160). Lor contains four domains referred to herein as scavenger receptor cysteine-rich domains ("SRCR domains") which are believed to be involved in binding to other cell surface proteins or extracellular molecules. The SRCR domain joins a long list of other widely distributed cysteine-containing domains found in extracellular portions of membrane proteins and in secreted proteins (Doolittle (1985) *Trends Biochem. Sci.* 10:233–237; Krieger in *Molecular Structures of Receptors,* eds. Rossow et al. (1986) *Horwood, Chichester,* U.K pp. 210–231). Examples include the EGF-like domain, immunoglobulin superfamily domains, the LDL receptor/complement. C9 domain, clotting factor Kringle domains, and fibronectin domains. These disulfide cross-linked domains appear to provide stable core structures that (i) are able to withstand the rigors of the extracellular environment; (ii) are well suited for a variety of biochemical tasks, often involving binding; and (iii) are readily juxtaposed to other types of domains to permit the construction of complex mosaic proteins. (Doolittle supra; Sudhof et al. (1985) *Science* 228:815–822). Lastly, a mouse cDNA encoding a putative protein having sequence homology to lysyl oxidase has recently been identified having the Accession No. AF053368, referred to herein as "Lor-2".

Lysyl oxidases ("LOXs") have been immunolocalized to the extracellular matrix regions of stroma surrounding early breast cancers (Decitre et al. (1998) *Lab Invest.* 78:143–151), with decreased expression observed in the stroma surrounding invasive breast cancers (Peyrol et al. (1997) *Am. J. Pathol.* 150:497–507). A progressive loss of LOX expression has also been observed during prostrate cancer progression in mice (Ren et al. (1998) *Cancer Res.* 58:1285–1290). These observations suggest that lysyl oxidases may function as tumor suppressors.

It has further been shown that human Lor is highly expressed in all adherent tumor cell lines examined, but not in cell lines that grow in suspension (Saito et al., supra), suggesting that LOXs can increase the adhesion properties of tumor cells. Lor expression was demonstrated to be concomitant with upregulation of type I procollagen. As adhesion properties contribute to the ability of tumor cells to colonize new sites, a tumor-promoting role for LOXs is also probable.

A greater understanding of the role which lysyl oxidase-like as well as SCRC domain containing proteins play in various disorders would lead to the determination of highly specific drug targets which would work to treat these disorders, e.g., cardiovascular disorders, a disorder arising from altered lysyl oxidase-like activity or a disorder arising from improperly regulated SRCR-domain containing protein activity giving rise to improperly regulated cellular processes.

SUMMARY OF THE INVENTION

The present invention is based, at least in part, on the discovery of novel nucleic acid molecules and proteins encoded by such nucleic acid molecules, referred herein as Lysyl Oxidase Related-2 ("Lor-2") molecules. The Lor-2 nucleic acid and protein molecules of the present invention are useful as modulating agents in regulating a variety of cellular processes (e.g., cellular processes in the cardiovascular system, for example, cardiac cellular processes). The Accordingly, in one aspect, this invention provides isolated nucleic acid molecules encoding Lor-2 proteins or portions thereof, as well as nucleic acid fragments suitable as primers or hybridization probes for the detection of Lor-2-encoding nucleic acids. In another embodiment, an isolated nucleic acid molecule of the present invention preferably encodes a Lor-2 protein which includes a signal sequence and/or is secreted. In yet another embodiment, an isolated nucleic acid molecule of the present invention preferably encodes a Lor-2 protein which lacks a signal sequence and/or is intracellular.

In one embodiment, a Lor-2 nucleic acid molecule of the invention is at least 60%, 65%, 70%, 75%, 80%, 85%, 90%, 91%, 92%, 93%, 94%, 95%, 96%, 97%, 98%, 99%, or more homologous to a nucleic acid sequence (e.g., to the entire length of the nucleotide sequence) having the nucleotide sequence shown in SEQ ID NO:1 or a complement thereof.

In a preferred embodiment, the isolated nucleic acid molecule includes the nucleotide sequence shown in SEQ ID NO:1, or a complement thereof. In another embodiment, the nucleic acid molecule includes nucleotides 143–2401 shown in SEQ ID NO:1. In another preferred embodiment, the nucleic acid molecule has the nucleotide sequence shown in SEQ ID NO:1. In another preferred embodiment, the nucleic acid molecule comprises a fragment of at least 50 contiguous nucleotides of the nucleotide sequence shown in SEQ ID NO: 1, or a complement thereof.

In another embodiment, a Lor-2 nucleic acid molecule includes a nucleotide sequence encoding a protein having an amino acid sequence at least about 60%, 65%, 70%, 75%, 80%, 85%, 90%, 91%, 92%, 93%, 94%, 95%, 96%, 97%, 98%, 99%, or more homologous to the amino acid sequence shown in SEQ ID NO:2.

In another preferred embodiment, an isolated nucleic acid molecule encodes the amino acid sequence of human Lor-2. In yet another preferred embodiment, the nucleic acid molecule includes a nucleotide sequence encoding a protein having the amino acid sequence shown in SEQ ID NO: 2. In yet another preferred embodiment, the nucleic acid molecule includes a nucleotide sequence encoding a protein at least 753 amino acids in length. In yet another preferred embodiment, the nucleic acid molecule includes a nucleotide sequence encoding a protein at least 728 amino acids in length. In a further preferred embodiment, the nucleic acid molecule encodes a protein having a Lor-2 activity (as described herein).

Another embodiment of the invention features nucleic acid molecules, preferably Lor-2 nucleic acid molecules, which specifically detect Lor-2 nucleic acid molecules relative to nucleic acid molecules encoding non-Lor-2 proteins. For example, in one embodiment, such a nucleic acid molecule is at least 300, 400, 500, 600, 650, 700, 750, or 753 nucleotides in length and hybridizes under stringent conditions to a nucleic acid molecule comprising the nucleotide sequence shown in SEQ ID NO:1, or a complement thereof. In a particularly preferred embodiment, the nucleic acid molecule comprises a fragment of at least 50 contiguous nucleotides of the nucleotide sequence of SEQ ID NO:1, SEQ ID NO:3, or a complement thereof. In another preferred embodiment, the nucleic acid molecules are at least 25, 50, 75, 100, 150, 200, 250 or more nucleotides (e.g., contiguous) in length and hybridize under stringent conditions to SEQ ID NO:1. In other preferred embodiments, the nucleic acid molecule encodes a naturally occurring allelic variant of a polypeptide having the amino acid sequence shown in SEQ ID NO:2, wherein the nucleic acid molecule hybridizes to a nucleic acid molecule having the nucleotide sequence shown in SEQ ID NO:1 under stringent conditions.

Another embodiment of the invention provides an isolated nucleic acid molecule which is antisense to a Lor-2 nucleic acid molecule, e.g., the coding strand of a Lor-2 nucleic acid molecule.

Another aspect of the invention provides a vector comprising a Lor-2 nucleic acid molecule. In certain embodiments, the vector is a recombinant expression vector. In another embodiment, the invention provides a host cell containing a vector of the invention. The invention also provides a method for producing a protein, preferably a Lor-2 protein, by culturing in a suitable medium, a host cell, e.g., a mammalian host cell such as a non-human mammalian cell, of the invention containing a recombinant expression vector, such that the protein is produced.

Another aspect of this invention features isolated or recombinant Lor-2 proteins and polypeptides. In one embodiment, the isolated polypeptide includes one or more of the following: a signal sequence, a LOX domain and at least one SCRC domain. In another embodiment, the isolated polypeptide includes a signal sequence, a LOX domain and at least two, three, or four SCRC domains. In another embodiment, the isolated protein preferably includes a signal sequence, a LOX domain, at least one SCRC domain and has an amino acid sequence which is at least 60%, 65%, 70%, 75%, 80%, 85%, 90%, 91%, 92%, 93%, 94%, 95%, 96%, 97%, 98%, 99% or more homologous to a protein having the amino acid sequence shown in SEQ ID NO:2. In yet another embodiment, the isolated protein, preferably a Lor-2 protein, includes a signal sequence, a LOX domain, at least one SCRC domain and is expressed and/or functions in cells of the cardiovascular system.

In yet another embodiment, an isolated protein, preferably a Lor-2 protein, has a signal sequence and/or is secreted. In another embodiment, the isolated protein, preferably a Lor-2 protein, includes a signal sequence, a LOX domain, at least one SCRC domain and is encoded by a nucleic acid molecule having a nucleotide sequence which hybridizes under stringent hybridization conditions to a nucleic acid molecule comprising the nucleotide sequence shown in SEQ ID NO:1.

In another embodiment, the isolated protein, preferably a Lor-2 protein, has an amino acid sequence at least about 60%, 65%, 70%, 75%, 80%, 85%, 90%, 91%, 92%, 93%, 94%, 95%, 96%, 97%, 98%, 99% or more homologous to a polypeptide having the amino acid sequence shown in SEQ ID NO:2 (e.g., the entire amino acid sequence shown in SEQ ID NO:2). In another embodiment, the invention features fragments of the proteins having the amino acid sequence shown in SEQ ID NO:2, wherein the fragment comprises at least about 25, 50, 75, 100, 150, 200, 250 or more amino acids (e.g, contiguous amino acids) of the amino acid sequence shown in SEQ ID NO:2. In another embodiment, the protein, preferably a Lor-2 protein, has the amino acid sequence shown in SEQ ID NO:2.

Another embodiment of the invention features an isolated protein, preferably a Lor-2 protein, which is encoded by a nucleic acid molecule having a nucleotide sequence at least about 60%, 65%, 70%, 75%, 80%, 85%, 90%, 91%, 92%, 93%, 94% 95%, 96%, 97%, 98%, 99%, or more homologous to a nucleic acid having the nucleotide sequence (e.g., to the entire length of the nucleotide sequence) shown in SEQ ID NO:1, or a complement thereof. This invention further features an isolated protein, preferably a Lor-2 protein, which is encoded by a nucleic acid molecule having a nucleotide sequence which hybridizes under stringent hybridization conditions to a nucleic acid molecule comprising the nucleotide sequence shown in SEQ ID NO:1, or a complement thereof.

The proteins of the present invention or portions thereof, e.g., biologically active portions thereof, can be operatively linked to a non-Lor-2 polypeptide (e.g., heterologous amino acid sequences) to form fusion proteins. The invention further features antibodies, such as monoclonal or polyclonal antibodies, that specifically bind proteins of the invention, preferably Lor-2 proteins. In addition, the Lor-2 proteins or portions thereof can be incorporated into pharmaceutical compositions, which optionally include pharmaceutically acceptable carriers.

In another aspect, the present invention provides a method for detecting the presence of a Lor-2 nucleic acid molecule, protein or polypeptide in a biological sample by contacting the biological sample with an agent capable of detecting a Lor-2 nucleic acid molecule, protein or polypeptide such that the presence of a Lor-2 nucleic acid molecule, protein or polypeptide is detected in the biological sample (e.g., a breast tissue sample or tumor sample).

In another aspect, the present invention provides a method for detecting the presence of Lor-2 activity in a biological sample by contacting the biological sample with an agent capable of detecting an indicator of Lor-2 activity such that the presence of Lor-2 activity is detected in the biological sample.

In another aspect, the invention provides a method for modulating Lor-2 activity comprising contacting a cell capable of expressing Lor-2 with an agent that modulates Lor-2 activity such that Lor-2 activity in the cell is modulated. In one embodiment, the agent inhibits Lor-2 activity. In another embodiment, the agent stimulates Lor-2 activity. In one embodiment, the agent is an antibody that specifically binds to a Lor-2 protein. In another embodiment, the agent modulates expression of Lor-2 by modulating transcription of a Lor-2 gene or translation of a Lor-2 mRNA. In yet another embodiment, the agent is a nucleic acid molecule having a nucleotide sequence that is antisense to the coding strand of a Lor-2 mRNA or a Lor-2 gene.

In one embodiment, the methods of the present invention are used to treat a subject having a disorder characterized by aberrant Lor-2 protein or nucleic acid expression or activity by administering an agent which is a Lor-2 modulator to the subject. In one embodiment, the Lor-2 modulator is a Lor-2 protein. In another embodiment the Lor-2 modulator is a Lor-2 nucleic acid molecule. In yet another embodiment, the Lor-2 modulator is a peptide, peptidomimetic, or other small molecule. In one embodiment, the disorder characterized by aberrant Lor-2 protein or nucleic acid expression is a cardiovascular disorder, e.g., congestive heart failure, ischemia, cardiac hypertrophy, ischemic-reperfusion injury or a disorder arising from improperly regulated Lor-2 protein action on target molecules/cells giving rise to improperly regulated cellular processes. In another embodiment, the disorder characterized by aberrant Lor-2 protein or nucleic acid expression is a proliferative disorder, e.g., cancer.

The present invention also provides a diagnostic assay for identifying the presence or absence of a genetic alteration characterized by at least one of (i) aberrant modification or mutation of a gene encoding a Lor-2 protein; (ii) misregulation of the gene; and (iii) aberrant post-translational modification of a Lor-2 protein, wherein a wild-type form of the gene encodes a protein with a Lor-2 activity.

Also provided are methods for diagnosing a tumor in a subject, determining the metastatic potential of a tumor or forming a prognosis, which include contacting a tumor sample form the individual with an agent capable of detecting Lor-2 (e.g., Lor-2 expression or activity), determining the amount of Lor-2, and forming the diagnosis, determination or prognosis based on the amount of Lor-2.

In another aspect the invention provides a method for identifying a compound that binds to or modulates the activity of a Lor-2 protein, by providing an indicator composition comprising a Lor-2 protein having Lor-2 activity, contacting the indicator composition with a test compound, and determining the effect of the test compound on Lor-2 activity in the indicator composition to identify a compound that modulates the activity of a Lor-2 protein.

Also featured are methods of regulating metastasis in an individual or inhibiting tumor progression in an individual which include administering to the individual a Lor-2 modulator (e.g., a Lor-2 inhibitor).

Other features and advantages of the invention will be apparent from the following detailed description and claims.

BRIEF DESCRIPTION OF THE DRAWINGS

FIGS. 1A–B depicts the cDNA sequence of human Lor-2. The nucleotide sequence corresponds to nucleic acids 1–2920 of SEQ ID NO:1.

FIGS. 2A–2B depicts the cDNA sequence of human Lor-2. The amino acid sequence corresponds to amino acids 1–753 of SEQ ID NO:2.

FIG. 3 depicts the coding sequence of human Lor-2. The nucleotide sequence corresponds to nucleic acids 1–2259 of SEQ ID NO:3.

FIGS. 5A–5D depicts a multiple sequence alignment of the amino acid sequence of human lysyl oxidase, LOX (Accession Number 2144342) (SEQ ID NO:5), human lysyl oxidase-like protein, LOL (Accession Number L21186) (SEQ ID NO:6), human lysyl oxidase-related protein, Lor (Accession Number U89942) (SEQ ID NO:7), murine lysyl oxidase-related protein 2, Lor-2 (Accession No. AF053368, SEQ ID NO:8), and the amino acid sequence of human Lor-2 (corresponding amino acids 1 to 753 of SEQ ID NO:2). The alignment was generated using the Clustal algorithm which is part of the MegAlign™ software package. The multiple alignment parameters are as follows: Gap Penalty=10; Gap Length Penalty=10. The pairwise alignment parameters are as follows: K-tuple=1; Gap Penalty=3; Window=5; Diagonals Saved=5; Weight Residue Table= PAM250. The SCRC domains are indicated in italics. The lysyl oxidase domain is indicated in bold. The copper binding site is overlined. The lysyl oxidase-related region is underlined. (For the huLO sequence depicted, the amino acid residues corresponding to the processed enzyme are underlined.)

DETAILED DESCRIPTION OF THE INVENTION

Figure 4:
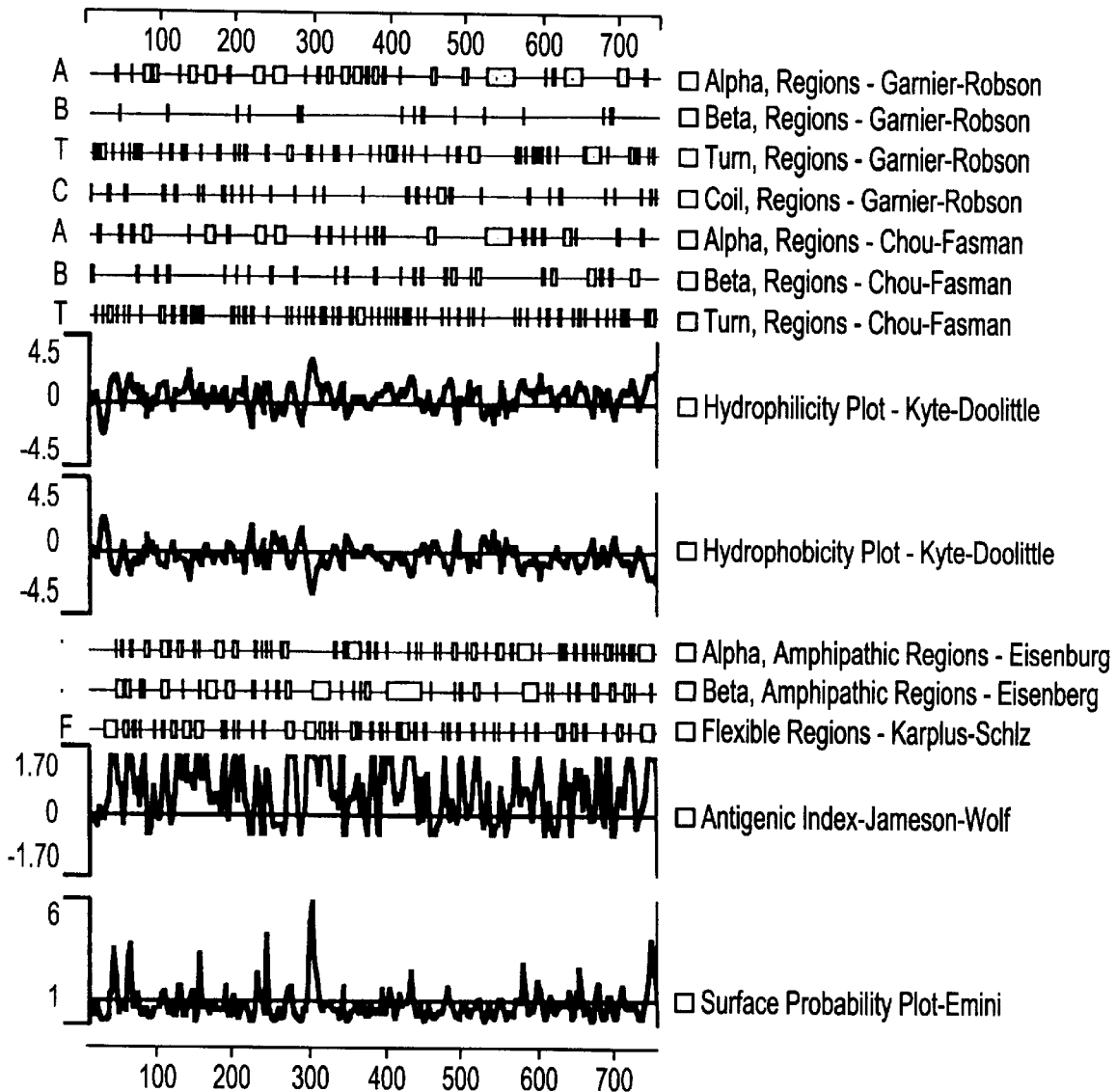
FIG. 4 shows a protean analysis of the Lor-2 amino acid sequence depicted in SEQ ID NO:2. Shown are regions identified with the following algorithms: alpha, beta turn and coil regions, Garnier-Robson algorithm (Garnier et al. (1978) *J Mol Biol* 120:97); alpha, beta, and turn regions, Chou-Fasman algorithm (Chou and Fasman (1978) *Adv in Enzymol Mol* 47:45–148); hydrophilicity and hydrophobicity plots, Kyte-Doolittle algorithm (Kyte and Doolittle (1982) *J Mol Biol* 157:105–132); alpha amphipathic and beta amphipathic regions, Eisenberg algorithm (Eisenberg et al. (1982) *Nature* 299:371–374); flexible regions, Karplus-Schulz algorithm (Karplus and Schulz (1985) *Naturwissens-Chafen* 72:212–213); antigenic index, Jameson-Wolf algorithm (Jameson and Wolf (1988) *CABIOS* 4:121–136); surface probability plot, Emini algorithm (Emini et al. (1985) *J Virol* 55:836–839).

The present invention is based, at least in part, on the discovery of novel molecules, referred to herein as Lysyl Oxidase Related-2 ("Lor-2") molecules or "Lor-2" nucleic acid and polypeptide molecules, which play a role in or function in a variety of cellular processes in the cardiovascular system, e.g., cardiac cell function. In another embodiment, the Lor-2 molecules of the present invention modulate the activity of one or more proteins involved in a cardiovascular disorder, e.g., congestive heart failure, ischemia, cardiac hypertrophy, ischemic-reperfusion injury.

As used herein, the term "cardiovascular disorder" includes a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, coronary artery disease, valvular disease, arrhythmias, and cardiomyopathies.

As used herein, the term "congestive heart failure" includes a condition characterized by a diminished capacity of the heart to supply the oxygen demands of the body. Symptoms and signs of congestive heart failure include diminished blood flow to the various tissues of the body, accumulation of excess blood in the various organs, e.g., when the heart is unable to pump out the blood returned to it by the great veins, exertional dyspnea, fatigue, and/or peripheral edema, e.g., peripheral edema resulting from left ventricular dysfunction. Congestive heart failure may be acute or chronic. The manifestation of congestive heart failure usually occurs secondary to a variety of cardiac or systemic disorders that share a temporal or permanent loss of cardiac function. Examples of such disorders include hypertension, coronary artery disease, valvular disease, and cardiomyopathies, e.g., hypertrophic, dilative, or restrictive cardiomyopathies. Congestive heart failure is described in, for example, Cohn J. N. et al. (1998) *American Family Physician* 57:1901–04, the contents of which are incorporated herein by reference.

As used herein, the term "cardiac cellular processes" includes intra-cellular or inter-cellular processes involved in the functioning of the heart. Cellular processes involved in the nutrition and maintenance of the heart, the development of the heart, or the ability of the heart to pump blood to the rest of the body are intended to be covered by this term. Such processes include, for example, cardiac muscle contraction, distribution and transmission of electrical impulses, and cellular processes involved in the opening and closing of the cardiac valves. The term "cardiac cellular processes" further includes processes such as the transcription, translation and post-translational modification of proteins involved in the functioning of the heart, e.g., myofilament specific proteins, such as troponin I, troponin T, myosin light chain 1 (MLC1), and α-actinin.

One embodiment of the invention features Lor-2 nucleic acid molecules, preferably human Lor-2 molecules, which were identified from a cDNA library made from the heart of a patient with congestive heart failure (CHF). The Lor-2 nucleic acid and protein molecules of the invention are described in further detail in the following subsections.

In yet another embodiment, the isolated proteins of the present invention, preferably Lor-2 proteins, can be identified based on the presence at least one SRCR domain and/or a lysyl oxidase domain and/or and a signal sequence.

In a preferred embodiment, a Lor-2 family member includes at least 1, 2, 3, 4, or more scavenger receptor cysteine-rich ("SRCR") domains. Scavenger receptors are proteins which have been implicated in the development of atherosclerosis and other macrophage-associated functions. For example, the type I mammalian macrophage scavenger receptors are membrane glycoproteins implicated in the pathologic deposition of cholesterol in arterial walls during atherogenesis (Freeman et al. (1990) *Proc. Natl. Acad. Sci. U.S.A.* 87:8810–8814). Scavenger receptors are characterized by the presence of a cysteine-rich domain, which is proposed to be involved in binding of physiological ligands (e.g., cell-surface proteins). This cysteine rich domain is referred to herein and in the art as a scavenger receptor cysteine-rich ("SRCR") domains. Intra- or intercellular binding of ligand to the SRCR domain is believed to play a role in signaling or adhesion As defined herein, a SRCR domain includes a protein domain which is about 88–112 amino acid residues in length and has about 16–60% identity with a SRCR of type I human macrophage scavenger receptor (e.g., amino acid residues 353–450 of SEQ ID NO:10). In another embodiment, a SRCR is abuse 90–110, 92–108, 94–106, or 95, 96, 97, 98, 99, 100, 101, 102, 103, 104, 105, or 106 amino acid residues in length and has about 22–54%, 26–50%, 28–48%, or 29%, 30%, 31%, 32%, 33%, 34%, 35%, 36%, 37%, 38%, 39%, 40%, 41%, 42%, 43%, 44%, 45%, 46%, or 47% identity with a SRCR of type I human macrophage scavenger receptor (e.g., amino acid residues 353–450 of SEQ ID NO:10). For example, a SRCR domain can be found in murine type I scavenger receptor (Accession No. 1709140) from about amino acid residues 360–457. SRCR domains also have been found in diverse secreted and other cell-surface proteins from humans (e.g., CD5 and complement factor I), mice (Ly-1), and sea urchins (speract receptor). Moreover, many proteins include more than one SRCR domain (e.g., Ly-1 includes 3 SRCR domains and the speract receptor includes 4 SRCR domains). Likewise, human Lor-2 includes 4 SRCR domains, as set forth below.

To identify the presence of an SRCR in a Lor-2 family member, the amino acid sequence of the protein family member can be searched against a database of HMMs (e.g., the Pfam database, release 3.3) e.g., using the default parameters. For example, the search can be performed using the hmmsf program (family specific) and threshold score of 15 for determining a hit. hmmsf is available as part of the HMMER package of search programs (HMMER 2.1.1, December 1998) which is freely distributed by the Washington University school of medicine. In one embodiment, a hit to a SRCR HMM having a score of at least 30–40, preferably at least 50–60, more preferably at least 70–80, and more preferably at least 90 or more is determinative of the presence of a SRCR domain within a query protein. A search using the amino acid sequence of SEQ ID NO:2 was performed against the HMM database resulting in the identification of 4 SRCR domains in the amino acid sequence of SEQ ID NO:2. Accordingly, in one embodiment of the invention, a Lor-2 protein has an SRCR domain at about amino acids 51–145 of SEQ ID NO:2. (Score of 91.4 against the SRCR domain profile HMM Accession No. PF00530). In another embodiment, a Lor-2 protein has an SRCR domain at about amino acids 183–282 of SEQ ID NO:2. (Score of 35.8). In another embodiment, a Lor-2 protein has an SRCR domain at about amino acids 310–407 of SEQ ID NO:2. (Score of 128.9). In another embodiment, a Lor-2 protein has an SRCR domain at about amino acids 420–525 of SEQ ID NO:2. (Score of 55.2). The SRCRs of Lor-2, as well as those of huLor and muLor-2 are indicated by italics in FIG. 5.

Lor-2 family members can further include at least one or more speract receptor repeated domain ("SRRD") signatures. The speract receptor is a transmembrane glycoprotein of 500 amino acid residues (Dangott et al. (1989) *PNAS U.S.A.* 86:2128–2132) which consists of a large extracellular domain of 450 which contains four repeats of a ~115 amino acids termed more speract receptor repeated domain or "SRRDs". Multiple sequence alignment of the four repeats reveals at least 17 perfectly conserved residues (including six cysteines, six glycines, and three glutamates). A SRRD signature has been generated from an alignment of the four SRRDs and has the consensus sequence: G-x(5)-G-x(2)-E-x(6)-W-G-x(2)-C-x(3)-[FYW]-x(8)-C-x(3)-G, corresponding to SEQ ID NO:4. The SRRD signature is further described in PROSITE Document, Accession No. PDOC00348 (http://expasy.ch/cgi-bin/prosite-search-ac?PDOC00021) and as PROSITE Accession No. PS00420. In one embodiment, a SRRD signature is included within a SRCR. For example, a SRRD can be found in a SRCR of the C-terminal section of the mammalian macrophage scavenger receptor type I (Freeman et al. (1990) *PNAS U.S.A.* 87:8810–8814). Likewise, a SRRD signature can be found within the SRCR domain of human Lor-2 from about amino acids 312–349 of SEQ ID NO:2.

The consensus sequences herein are described according to standard Prosite Signature designation (e.g., all amino acids are indicated according to their universal single letter designation; X designates any amino acid; X(n) designates any n amino acids, e.g., X (2) designates any 2 amino acids; [FYW] indicates any one of the amino acids appearing within the brackets, e.g., any one of F, Y, or W, in the alternative, any one of Phe, Tyr, or Trp; and {x} indicates any amino but the amino acid included within the brackets.)

Lor-2 family members can further include at least one domain characteristic of lysyl oxidase, referred to herein as a lysyl oxidase domain or "LOX domain". Lysyl oxidase is an extracellular copper-dependent enzyme that catalyzes the oxidative deamination of peptidyl lysine residues in precursors of various collagens and elastins. The deaminated lysines are then able to form aldehyde cross-links. (Krebs et al. (1993) *Biochem. Biophys. Acta.* 1202:7–12). The amino acid sequence of lysyl oxidase includes a signal sequence (e.g., amino acids 1 to 21 of human lysyl oxidase set forth as SEQ ID NO:5, a pro-peptide region (e.g., amino acids 22 to 168 of SEQ ID NO:5), and a region corresponding to the active, processed protein (e.g, amino acids 169–417 of SEQ ID NO:5), which is responsible for the enzymatic function of the molecule. Lysyl oxidase can be further characterized by the presence of a copper-binding site (Krebs et al. (1993) *Biochem. Biophys. Acta.* 12–2:7–12) having four conserved histidine residues that presumably supply the nitrogen ligands for copper coordination, and a quinone cofactor binding site (Wang et al. (1996) *Science* 273:1078–1084) (e.g, his289, his292, his294, and his296 of SEQ ID NO:5), also referred to as a "copper talon". The copper binding site of human Lor-2 can be found, for example, at about amino acids 286–296 of SEQ ID NO:5.

Accordingly, as used herein, the term "LOX domain" includes a protein domain which is about 245–275 amino acid residues in length, and has about 38–64% identity with the amino acid sequence of processed lysyl oxidase (e.g., amino acid residues 169–417 of SEQ ID NO:5). Preferably, a LOX domain is about 225–300, more preferably about 230–290 amino acid residues in length, and more preferably about 235–285, or 240–280 amino acid residues in length, and has about 34–65% identity, preferably about 42–62%, and more preferably about 46–56% or 50–52% identity with the amino acid sequence of processed lysyl oxidase (e.g., amino acid residues 169–417 of SEQ ID NO:5). For example, a LOX domain can be found in huLOL (SEQ ID NO:6) from about amino acids 310–574; in huLor (SEQ ID NO:7) from about amino acids 481–751; in mu Lor-2 (SEQ ID NO:8) from about amino acids 464–733; and in huLor-2 (SEQ ID NO:2) from about amino acids 463–732. The LOX domains of huLOL, huLor, muLor-2, and huLor-2 are indicated in bold in FIG. 5.

In another embodiment, a LOX domain is involved in a lysyl oxidase or lysyl oxidase-like function. Lysyl oxidase or lysyl oxidase-like functions include, for example, aminotransferase activity, peptidyl lysine oxidation, oxidative deamination of lysine, cross-linking of extracellular matrix components, copper binding, and/or copper metabolism. Lysyl oxidase or lysyl oxidase-like functions are described in detail, for example, in Kagan et al. in *Catalytic Properties and structural components of lysyl oxidase,* John Wiley & Sons (1995) pp. 100–121, the contents of which are incorporated herein by reference. In yet another embodiment, a LOX domain has at least one, preferably two, and more preferably three or four histidine residues corresponding to the conserved histidine residues of lysyl oxidase which are involved in copper binding. For example, a LOX domain of a human Lor-2 sequence set forth in SEQ ID NO:2 (e.g, amino acid residues 330–732 in SEQ ID NO:2) has four histidine residues (e.g., his604, his607, his609, and his611 of SEQ ID NO:2) which correspond to those of human lysyl oxidase set forth as SEQ ID NO:5.

A LOX domain in a protein can further be included within a lysyl oxidase-related region ("LOX-related region"). A LOX-related region within a protein (e.g., within a Lor-2 family member) includes a protein region which is about 380–580, preferably about 390–550, more preferably about 400, 420, 450 or 500 amino acid residues in length and has at least 30–35%, 40–45%, 50–55%, 60–65%, 70–75%, 80–85%, or 90–95% homology with, for example, the amino acid sequence of human LOX. To identify the presence of a LOX-related region in a Lor-2 family member, the amino acid sequence of the protein family member can be searched against the HMM database, as described previously. In one embodiment, a hit to a LOX HMM having a score of at least 100–110, preferably at least 120–130, more preferably at least 140–150, and more preferably at least 160 or more is determinative of the presence of a LOX-related region within a query protein. A search using the amino acid sequence of SEQ ID NO:2 was performed against the HMM database resulting a hit to a LOX HMM from about amino acids 330–732 of SEQ ID NO:2. (Score of 166.6 against the LOX domain profile HMM Accession No. PF01186). Similar LOX-related regions were identified in muLor-2 from about amino acids 318–733 of SEQ ID NO:8 (Score of 162.8), in huLOL from about amino acids 1–574 of SEQ ID NO:6 (Score of 382.2) and in huLor from about amino acids 358–751 of SEQ ID NO:7 (Score of 146.8). In yet another embodiment, a lysyl oxidase-related region has at least 40–45%, 50–55%, 60–65%, 70–75%, 80–85%, or 90–95% homology with the amino acid sequence of a LOX domain of a human Lor-2 sequence set forth in SEQ ID NO:2 (e.g., amino acid residues 330–732 in SEQ ID NO:2). The lysyl oxidase-related regions of huLOL, huLor, muLor-2 and huLor-2 are underlined in FIG. 5, as are the amino acids corresponding to processed lysyl oxidase (e.g., amino acids 169–417 of SEQ ID NO:5).

Another embodiment of the invention features a protein of the invention, preferably a Lor-2 protein, which contains a signal sequence. As used herein, a "signal sequence" refers to a peptide containing about 25 amino acids which occurs at the N-terminus of secretory proteins and which contains a large number of hydrophobic amino acid residues. For example, a signal sequence contains at least about 17–33 amino acid residues, preferably about 20–30 amino acid residues, more preferably about 24–26 amino acid residues, and more preferably about 25 amino acid residues, and has at least about 35–65%, preferably about 38–50%, and more preferably about 40–45% hydrophobic amino acid residues (e.g., Valine, Leucine, Isoleucine or Phenylalanine). Such a "signal sequence", also referred to in the art as a "signal peptide", serves to direct a protein containing such a sequence to a lipid bilayer. For example, in one embodiment, a Lor-2 protein contains a signal sequence containing about amino acids 1–25 of SEQ ID NO:2.

In yet another embodiment, a protein of the invention, preferably a Lor-2 protein, encodes a mature protein. As used herein, the term "mature protein" refers to a protein of the invention, preferably a Lor-2 protein, from which the signal peptide has been cleaved. In an exemplary embodiment, a mature Lor-2 protein contains amino acid residues 26 to 753 of SEQ ID NO:2.

In yet another embodiment, Lor-2 family members include at least 1, 2, 3, 4, 5 or more N-glycosylation sites. Predicted N-glycosylation sites are found, for example, from about amino acid 111–114, 266–269, 390–393, 481–484, and 625–628 of SEQ ID NO:2.

Lor-2 family members can further include at least 1, 2, 3, 4, 5, 6, 7, 8, or more or more Protein kinase C ("PKC") phosphorylation sites. Predicted PKC phosphorylation sites are found, for example, from about amino acid 97–99, 104–106, 221–223, 268–270, 352–354, 510–512, 564–566, and 649–651 of SEQ ID NO:2.

Lor-2 family members can further include at least 1, 2, 3, 4, 5, 6, 7, 8, 9, 10, 11, 12, 13, 14, or more Casein kinase II phosphorylation sites. Predicted casein kinase II phosphorylation sites are found, for example, from about amino acid 31–34, 68–71, 115–118, 120–123, 135–138, 330–333, 352–355, 377–380, 392–395, 411–414, 424–427, 493–496, 527–530, and 617–620 of SEQ ID NO:2.

Lor-2 family members can further include at least 1, 2, 3, 4, 5, 6, 7, 8, 9, 10, 11, 12, 13, 14, 15, 16, 17, 18, 19, or more N-myristoylation sites. Predicted N-myristoylation sites are found, for example, from about amino acids 13–18, 116–121, 130–135, 273–278, 312–317, 359–364, 378–383, 403–408, 443–448, 451–456, 463–468, 470–475, 489–494, 506–511, 515–520, 521–526, 626–631, 661–666, and 746–751 of SEQ ID NO:2.

Lor-2 family members can further include at least one or more amidation sites. A predicted amidation site is found, for example, from amino acid 117–180 of SEQ ID NO:2. As used herein, the site(s) have a consensus sequence selected from: N-{P}-[ST]-{P}, where N is a glycosylation site (see PROSITE document PS00001); [ST]-X-[RK], where S or T is a phosphorylation site (see PROSITE document PS00005); [ST]-X (2)-[DE], where S or T is a phosphorylation site (see PROSITE document PS00006); G-{EDRKHPFYW}-X (2)-[STAGCN]-{P}, where G is an N-myristoylation site (see PROSITE Accession No. PS00008); and X-G-[RK]-[RK]. where X is an amidation site (see PROSITE document PS00009). These sites are further described at http://expasy.hcuge.ch/cgi-bin/get-prodoc-entry?PDOC00001, PDOC00005, PDOC00006, PDOC00008,and PS00009, respectively.

Isolated proteins of the present invention, preferably Lor-2 proteins, have an amino acid sequence sufficiently homologous to the amino acid sequence of SEQ ID NO:2 or are encoded by a nucleotide sequence which includes a nucleotide sequence sufficiently homologous to SEQ ID NO:1. As used herein, the term "sufficiently homologous" includes a first amino acid or nucleotide sequence which contains at least a minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40% or 50% homology, preferably 55%, 60%, 65%, 70% or 75% homology, more preferably 80%, 85%, 90%, 91%, 92%, 93%, 94%, 95%, 96%, 97%, 98% or 99% homology across the amino acid sequences of the domains and contain at least one and preferably two structural domains or motifs, are defined herein as sufficiently homologous. Furthermore, amino acid or nucleotide sequences which share at least 30%, 40% or 50% homology, preferably 55%, 60%, 65%, 70% or 75% homology, more preferably 80%, 85%, 90%, 91%, 92%, 93%, 94%, 95%, 96%, 97%, 98% or 99% homology and share a common functional activity are defined herein as sufficiently homologous.

Accordingly, another embodiment of the invention features isolated Lor-2 proteins and polypeptides having a Lor-2 activity. Preferred proteins are Lor-2 proteins having at least a signal sequence, a LOX domain, and at least one SRRD signature. Other preferred proteins are Lor-2 proteins having at least two, three, or four SRRD signatures. Other preferred proteins are Lor-2 proteins having at least a signal sequence, a LOX domain, and a SRCR domain. Other preferred proteins are Lor-2 proteins having at least a signal sequence, a LOX domain, and at least two SCRC domains. Other preferred proteins are Lor-2 proteins having at least a signal sequence, a LOX domain, and at least three SCRC domains. Other preferred proteins are Lor-2 proteins having at least a signal sequence, a LOX domain, and at least four SCRC domains.

The nucleotide sequence of the isolated human Lor-2 cDNA and the predicted amino acid sequence of the human Lor-2 polypeptide are shown in FIGS. 1 and 2 (SEQ ID NOs: 1, 2), respectively.

The human Lor-2 cDNA (set forth in SEQ ID NO:1), which is approximately 2920 nucleotides in length, encodes a protein having a molecular weight of approximately 83.166 kD (with signal sequence) and 80.404 kD (without signal sequence) and which is approximately 753 (with signal sequence) (SEQ ID NO:2) and 728 amino acid residues (without signal sequence) in length. An ~3.0 kb Lor-2 message was found to be expressed most tissues tested but was most highly expressed in heart and placenta (at least heart, brain, placenta, lung, liver, skeletal muscle, kidney, and pancreas tissues were tested). High expression of Lor-2 was also observed in the G361 melanoma cell line and in the SW480 adenocarcinoma colon cell line (at least G361, SW480, HL60, Hela 53, K562, Molty, Raji, and A549 cell lines were tested).

In a preferred embodiment, Lor-2 proteins of the invention have an amino acid sequence of at least 600–900, preferably about 650–850, more preferably about 700–800, and even more preferably about 720–760, 728 or 753 amino acid residues in length.

As used interchangeably herein, a "Lor-2 activity", "biological activity of Lor-2" or "functional activity of Lor-2", includes an activity exerted by a Lor-2 protein, polypeptide or nucleic acid molecule as determined in vivo, in vitro, or in situ, according to standard techniques. In one embodiment, a Lor-2 activity is a direct activity, such as an association with a Lor-2-target molecule. As used herein, a "target molecule" is a molecule with which a Lor-2 protein binds or interacts in nature, such that Lor-2-mediated function is achieved. A Lor-2 target molecule can be a Lor-2 protein or polypeptide of the present invention or a non-Lor-2 molecule. For example, a Lor-2 target molecule can be a non-Lor-2 protein molecule. Alternatively, a Lor-2 activity is an indirect activity, such as an activity mediated by interaction of the Lor-2 protein with a Lor-2 target molecule such that the target molecule modulates a downstream cellular activity (e.g., interaction of a Lor-2 molecule with a Lor-2 target molecule can modulate the activity of that target molecule on a cardiac cell).

In a preferred embodiment, a Lor-2 activity is at least one or more of the following activities: (i) interaction of a Lor-2 protein with a Lor-2 target molecule; (ii) interaction of a Lor-2 protein with a Lor-2 target molecule, wherein the Lor-2 target is a ligand; (iii) interaction of a Lor-2 protein with a Lor-2 target molecule, wherein the Lor-2 target is an extracellular matrix component (e.g., collagen or elastin); and (iv) modification of a Lor-2 target molecule (e.g., postranslational modification).

In yet another preferred embodiment, a Lor-2 activity is at least one or more of the following activities: (1) crosslinking an extracellular matrix component; (2) regulating bone resorption and/or metabolism; (3) regulating copper metabolism; (4) modulating maturation, stabilization and/or degradation of extracellular matrix components; (5) regulating cellular signaling; and (6) regulating cellular adhesion (e.g adhesion of a tumor cell).

In another embodiment of the invention, a Lor-2 molecule or preferably, a Lor-2 modulator, is useful for regulating, preventing and/or treating at least one or more of the following diseases or disorders: (1) diseases or disorders involving impaired copper metabolism (e.g., type IX of the Ehlers-Danlos syndrome and the Menkes syndrome); (2) bone disorders (e.g., osteoporosis or osteoarthritis); (3) fibrotic disorders (e.g., atherosclerosis, tissue and/or organ fibrosis); (4) proliferative disorders (e.g., cancer, for example, prostate cancer, breast cancer, lung cancer and the like); (5) vascular disorders (e.g., ischemia, ischemic-reperfusion injury); and (6) cardiac trauma (e.g., iatrogenic, accidental).

In yet another embodiment of the invention, a Lor-2 molecule or preferably, a Lor-2 modulator, is useful for regulating, preventing and/or treating at least one or more of the following diseases or disorders: (1) cardiac hypertrophy and cardiomyopathy; (2) cardiac pathologies; (3) myocardial hypertrophy and cardiovascular lesions; (4) myocardial aneurysms; (5) atherosclerotic cardiovascular disease; (6) fibrotic disease; (7) osteoporosis; (8) metastasis/prostate cancer; (9) cellular senescence/tumor suppression; (10) tumor progression; (11) liver fibrosis; (12) wound healing; (13) hypertension; (14) diabetes; (15) arthritis; and (16) bone disease (e.g., osteoporosis or osteoarthritis).

In yet another embodiment, a Lor-2 modulator is useful for regulating (e.g., inhibiting) tumor progression. For example, Lor-2 may be secreted by a tumor cell facilitating adhesion (e.g., enhancing the adhesive properties) of the cell. Accordingly, Lor-2 modulators can be used to affect the adhesive properties of tumor cells (e.g., to surrounding tissues).

In yet another embodiment, a Lor-2 modulator, is useful for regulating or preventing immunosuppression by tumor cells. For example, Lor-2 may be secreted by a tumor cell, conferring on that cell a growth advantage (e.g., maintaining the growth, differentiation, and transformed phenotype of the tumor cell). In such a situation, secreted Lor-2 can inhibit cytoxicity (e.g, lymphocytotoxicity, for example, IL-2-induced lymphocytotoxicity). Accordingly, Lor-2 may function to suppress the generation and/or proliferation of lymphocytic cells (e.g., lymphocyte-activated killer cells).

Various aspects of the invention are described in further detail in the following subsections:

I. Isolated Nucleic Acid Molecules

One aspect of the invention pertains to isolated nucleic acid molecules that encode Lor-2 proteins or biologically active portions thereof, as well as nucleic acid fragments for use as hybridization probes to identify Lor-2-encoding nucleic acids (e.g., Lor-2 mRNA) and fragments for use as PCR primers for the amplification or mutation of Lor-2 nucleic acid molecules. As used herein, the term "nucleic acid molecule" is intended to include DNA molecules (e.g, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from chromosomal DNA, e.g., other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Lor-2 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, or a portion thereof, can be isolated using standard molecular biology techniques and the sequence information provided herein. For Example, using all or portion of the nucleic acid sequence of SEQ ID NO:1, the nucleotide sequence of, as a hybridization probe, Lor-2 nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1 can be isolated by the polymerase chain reaction (PCR) using synthetic oligonucleotide primers designed based upon the sequence of SEQ ID NO:1.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to Lor-2 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:3. The sequence of SEQ ID NO:3 corresponds to the coding region of human Lor-2 cDNA. This cDNA comprises sequences encoding the human Lor-2 protein (i.e., "the coding region", from nucleotides 143–2401 of SEQ ID NO:1).

In yet another embodiment, an isolated nucleic acid molecule of the invention comprises the nucleotide sequence shown in SEQ ID NO:1. The sequence of SEQ ID NO:1 corresponds to the coding and noncoding regions of human Lor-2 cDNA. This cDNA comprises sequences encoding the human Lor-2 protein (i.e., "the coding region", from nucleotides 143–2401) and noncoding regions (i.e., from nucleotides 1–142 and from nucleotides 2402–2920).

In another preferred embodiment, an isolated nucleic acid molecule of the invention comprises a nucleic acid molecule which is a complement of the nucleotide sequence shown in SEQ ID NO:1 or a portion of any of these nucleotide sequences. A nucleic acid molecule which is complementary to the nucleotide sequence shown in SEQ ID NO:1 is one which is sufficiently complementary to the nucleotide sequence shown in SEQ ID NO:1 such that it can hybridize to the nucleotide sequence shown in SEQ ID NO:1 thereby forming a stable duplex.

In still another preferred embodiment, an isolated nucleic acid molecule of the present invention comprises a nucleotide sequence which is at least about 60–65%, 65–70%, 70–75%, 75–80%, 80–85%, 85–90%, 90–95%, or 99%, or more homologous to the nucleotide sequences shown in SEQ ID NO:1, or a portion of any of these nucleotide sequences.

Moreover, the nucleic acid molecule of the invention can comprise only a portion of the nucleic acid sequence shown in SEQ ID NO:1, for example a fragment which can be used as a probe or primer or a fragment encoding a portion of a Lor-2 protein. The nucleotide sequence determined from the cloning of the Lor-2 gene allows for the generation of probes and primers designed for use in identifying and/or cloning other Lor-2 family members, as well as Lor-2 homologues from other species. The probe/primer typically comprises substantially purified oligonucleotide. The oligonucleotide typically comprises a region of nucleotide sequence that hybridizes under stringent conditions to at least about 12 or 15, preferably about 18 or 20, preferably about 22 or 25, more preferably about 30, 35, 40, 45, 50, 55, 60, 65, or 75 consecutive nucleotides of a sense sequence shown in SEQ ID NO:1 of an anti-sense sequence of SEQ ID NO:1, or of a naturally occurring mutant of SEQ ID NO:1.

Probes based on the Lor-2 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a Lor-2 protein, such as by measuring a level of a Lor-2-encoding nucleic acid in a sample of cells from a subject e.g., detecting Lor-2 mRNA levels or determining whether a genomic Lor-2 gene has been mutated or deleted.

A nucleic acid fragment encoding a "biologically active portion of a Lor-2 protein" can be prepared by isolating a portion of the nucleotide sequence of SEQ ID NO:1, which encodes a polypeptide having a Lor-2 biological activity (the biological activities of the Lor-2 proteins have previously been described), expressing the encoded portion of the Lor-2 protein (e.g., by recombinant expression in vitro) and assessing the activity of the encoded portion of the Lor-2 protein.

The invention further encompasses nucleic acid molecules that differ from the nucleotide sequence shown in SEQ ID NO:1 due to degeneracy of the genetic code and thus encode the same Lor-2 proteins as those encoded by the nucleotide sequence shown in SEQ ID NO:1. In another embodiment, an isolated nucleic acid molecule of the invention has a nucleotide sequence encoding a protein having the amino acid sequence shown in SEQ ID NO:2.

In addition to the Lor-2 nucleotide sequences shown in SEQ ID NO:1, it will be appreciated by those skilled in the art that DNA sequence polymorphisms that lead to changes in the amino acid sequences of the Lor-2 proteins may exist within a population (e.g., the human population). Such genetic polymorphism in the Lor-2 genes may exist among individuals within a population due to natural allelic variation. As used herein, the terms "gene" and "recombinant gene" refer to nucleic acid molecules isolated from chromosomal DNA, which include an open reading frame encoding a Lor-2 protein, preferably a mammalian Lor-2 protein. A gene includes coding DNA sequences, non-coding regulatory sequences, and introns. As used herein, a gene refers to an isolated nucleic acid molecule, as defined herein.

Allelic variants of human Lor-2 include both functional and non-functional Lor-2 proteins. Functional allelic variants are naturally occurring amino acid sequence variants of the human Lor-2 protein that maintain the ability to bind a Lor-2 ligand and/or modulate a Lor-2 function. Functional allelic variants will typically contain only conservative substitution of one or more amino acids of SEQ ID NO:2 or substitution, deletion or insertion of non-critical residues in non-critical regions of the protein.

Non-functional allelic variants are naturally occurring amino acid sequence variants of the human Lor-2 protein that do not have the ability to either bind a Lor-2 ligand and/or modulate a Lor-2 function. Non-functional allelic variants will typically contain a non-conservative substitution, a deletion, or insertion or premature truncation of the amino acid sequence of SEQ ID NO:2 or a substitution, insertion or deletion in critical residues or critical regions.

The present invention further provides non-human orthologues of the human Lor-2 protein. Orthologues of the human Lor-2 protein are proteins that are isolated from non-human organisms and possess the same Lor-2 ligand binding and/or modulation of a Lor-2 function capabilities of the human Lor-2 protein. Orthologues of the human Lor-2 protein can readily be identified as comprising an amino acid sequence that is substantially homologous to SEQ ID NO:2.

Moreover, nucleic acid molecules encoding other Lor-2 family members (e.g., Lor-2-2), and thus which have a nucleotide sequence which differs from the Lor-2 sequences of SEQ ID NO:1 are intended to be within the scope of the invention. For example, a rat Lor-2 cDNA can be identified based on the nucleotide sequence of human Lor-2. Moreover, nucleic acid molecules encoding Lor-2 proteins from different species, and thus which have a nucleotide sequence which differs from the Lor-2 sequences of SEQ ID NO:1 are intended to be within the scope of the invention.

Nucleic acid molecules corresponding to natural allelic variants and homologues of the Lor-2 cDNAs of the invention can be isolated based on their homology to the Lor-2 nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1. In other embodiment, the nucleic acid is at least 18, 20, 22, 25, 30, 50, 100, 250, 500, 550, or 600 nucleotides in length. As used herein, the term "hybridizes under stringent conditions" is intended to describe conditions for hybridization and washing under which nucleotide sequences at least about 60%, 65%, 70%, 75%, 80%, 85%, 90%,95%, 98%, 99% or more homologous to each other typically remain hybridized to each other. Preferably, the conditions are such that sequences at least about 50%, at least about 60%, at least about 70%, more preferably at least about 80%, even more preferably at least about 85% to 90%, more preferably at least 95% homologous to each other typically remain hybridized to each other. Such stringent conditions are known to those skilled in the art and can be found in *Current Protocols in Molecular Biology,* John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50° C., preferably at 55° C., preferably at 60° C. and even more preferably at 65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the Lor-2 sequences that may exist in the population, the skilled artisan will further appreciate that changes can be introduced by mutation into the nucleotide sequences of SEQ ID NO:1, thereby leading to changes in the amino acid sequence of the encoded Lor-2 proteins, without altering the functional ability of the Lor-2 proteins. For example, nucleotide substitutions leading to amino acid substitutions at "non-essential" amino acid residues can be made in the sequence of SEQ ID NO:1. A "non-essential" amino acid residue is a residue that can be altered from the wild-type sequence of Lor-2 (e.g., the sequence of SEQ ID NO:2) without altering the biological activity, whereas an "essential" amino acid residue is required for biological activity. For example, amino acid residues that are conserved among the Lor-2 proteins of the present invention, are predicted to be particularly unamenable to alteration (e.g., amino acid residues conserved among the proteins aligned in FIG. 5). Moreover, amino acid residues that are defined by the SRCR domains are particularly unamenable to alteration. Furthermore, additional amino acid residues that are conserved between the Lor-2 proteins of the present invention and other members of the lysyl oxidase superfamily or protein families containing LOX are not likely to be amenable to alteration.

Accordingly, another aspect of the invention pertains to nucleic acid molecules encoding Lor-2 proteins that contain changes in amino acid residues that are not essential for activity. Such Lor-2 proteins differ in amino acid sequence from SEQ ID NO:2 yet retain biological activity. In one embodiment, the isolated nucleic acid molecule comprises a nucleotide sequence encoding a protein, wherein the protein comprises an amino acid sequence at least about 60%, 65%, 70%, 75%, 80%, 85%, 90%, 95%, 98%, 99% or more homologous to the amino acid sequence shown in SEQ ID NO:2.

An isolated nucleic acid molecule encoding a Lor-2 protein homologous to the protein having an amino acid sequence as set forth in SEQ ID NO:2 can be created by introducing one or more nucleotide substitutions, additions or deletions into the nucleotide sequence shown in SEQ ID NO:1, such that one or more amino acid substitutions, additions or deletions are introduced into the encoded protein. Mutations can be introduced into the nucleotide sequence shown in SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a Lor-2 protein is preferably replaced with another amino acid residue from the same side chain family. Alternatively, in another embodiment, mutations can be introduced randomly along all or part of a Lor-2 coding sequence, such as by saturation mutagenesis, and the resultant mutants can be screened for Lor-2 biological activity to identify mutants that retain activity. Following mutagenesis of the nucleotide sequence shown in SEQ ID NO:1, the encoded protein can be expressed recombinantly and the activity of the protein can be determined.

In a preferred embodiment, a mutant Lor-2 protein can be assayed for the ability to (1) crosslink an extracellular matrix component; (2) regulate bone resorption; (3) regulate copper metabolism; (4) modulate maturation and/or stabilize extracellular matrix components; (5) regulate cellular signaling; (6) regulate cellular adhesion; (7) regulate cardiac cellular processes; or (8) modulate a Lor-2-related disorder as defined herein.

In addition to the nucleic acid molecules encoding Lor-2 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Lor-2 coding strand, or to only a portion thereof. In one embodiment, an antisense nucleic acid molecule is antisense to a "coding region" of the coding strand of a nucleotide sequence encoding Lor-2. The term "coding region" refers to the region of the nucleotide sequence comprising codons which are translated into amino acid residues (e.g., the coding region of human Lor-2 corresponds to 143–2401 of SEQ ID NO:1). In another embodiment, the antisense nucleic acid molecule is antisense to a "noncoding region" of the coding strand of a nucleotide sequence encoding Lor-2. The term "noncoding region" refers to 5' and 3' sequences which flank the coding region that are not translated into amino acids (i.e., also referred to as 5', which corresponds to 1–142 of SEQ ID NO:1 and 3' untranslated regions, which corresponds to 2402–2920 of SEQ ID NO:1).

Given the coding strand sequences encoding Lor-2 disclosed herein (e.g., SEQ ID NO:1), antisense nucleic acids of the invention can be designed according to the rules of Watson and Crick base pairing. The antisense nucleic acid molecule can be complementary to the entire coding region of Lor-2 mRNA, but more preferably is an oligonucleotide which is antisense to only a portion of the coding or noncoding region of Lor-2 mRNA. For example, the antisense oligonucleotide can be complementary to the region surrounding the translation start site of Lor-2 mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a Lor-2 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave Lor-2 mRNA transcripts to thereby inhibit translation of Lor-2 mRNA. A ribozyme having specificity for a Lor-2-encoding nucleic acid can be designed based upon the nucleotide sequence of a Lor-2 cDNA disclosed herein (i.e., SEQ ID NO:1). For example, a derivative of a Tetrahymena L-19 IVS RNA can be constructed in which the nucleotide sequence of the active site is complementary to the nucleotide sequence to be cleaved in a Lor-2-encoding mRNA. See, e.g., Cech et al. U.S. Pat. No. 4,987,071; and Cech et al. U.S. Pat. No. 5,116,742. Alternatively, Lor-2 mRNA can be used to select a catalytic RNA having a specific ribonuclease activity from a pool of RNA molecules. See, e.g, Bartel, D. and Szostak, J. W. (1993) *Science* 261:1411–1418.

Alternatively, Lor-2 gene expression can be inhibited by targeting nucleotide sequences complementary to the regulatory region of the Lor-2 (e.g., the Lor-2 promoter and/or enhancers) to form triple helical structures that prevent transcription of the Lor-2 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the Lor-2 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al PNAS 93: 14670–675.

PNAs of Lor-2 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of Lor-2 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of Lor-2 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of Lor-2 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810, published Dec. 15, 1988) or the blood-brain barrier (see, e.g., PCT Publication No. WO89/10134, published Apr. 25, 1988). In addition, oligonucleotides can be modified with hybridization-triggered cleavage agents (See, e.g., Krol et al (1988) *BioTechniques* 6:958–976) or intercalating agents. (See, e.g., Zon (1988) *Pharm. Res.* 5:539–549). To this end, the oligonucleotide may be conjugated to another molecule, (e.g, a peptide, hybridization triggered cross-linking agent, transport agent, or hybridization-triggered cleavage agent).

II. Isolated Lor-2 Proteins and Anti-Lor-2 Antibodies

One aspect of the invention pertains to isolated Lor-2 proteins, and biologically active portions thereof, as well as polypeptide fragments suitable for use as immunogens to raise anti-Lor-2 antibodies. In one embodiment, native Lor-2 proteins can be isolated from cells or tissue sources by an appropriate purification scheme using standard protein purification techniques. In another embodiment, Lor-2 proteins are produced by recombinant DNA techniques. Alternative to recombinant expression, a Lor-2 protein or polypeptide can be synthesized chemically using standard peptide synthesis techniques.

An "isolated" or "purified" protein or biologically active portion thereof is substantially free of cellular material or other contaminating proteins from the cell or tissue source from which the Lor-2 protein is derived, or substantially free from chemical precursors or other chemicals when chemically synthesized. The language "substantially free of cellular material" includes preparations of Lor-2 protein in which the protein is separated from cellular components of the cells from which it is isolated or recombinantly produced. In one embodiment, the language "substantially free of cellular material" includes preparations of Lor-2 protein having less than about 30% (by dry weight) of non-Lor-2 protein (also referred to herein as a "contaminating protein"), more preferably less than about 20% of non-Lor-2 protein, still more preferably less than about 10% of non-Lor-2 protein, and most preferably less than about 5% non-Lor-2 protein. When the Lor-2 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of Lor-2 protein in which the protein is separated from chemical precursors or other chemicals which are involved in the synthesis of the protein. In one embodiment, the language "substantially free of chemical precursors or other chemicals" includes preparations of Lor-2 protein having less than about 30% (by dry weight) of chemical precursors or non-Lor-2 chemicals, more preferably less than about 20% chemical precursors or non-Lor-2 chemicals, still more preferably less than about 10% chemical precursors or non-Lor-2 chemicals, and most preferably less than about 5% chemical precursors or non-Lor-2 chemicals.

Biologically active portions of a Lor-2 protein include peptides comprising amino acid sequences sufficiently homologous to or derived from the amino acid sequence of the Lor-2 protein, e.g., the amino acid sequence shown in SEQ ID NO: 2, which include less amino acids than the full length Lor-2 proteins, and exhibit at least one activity of a Lor-2 protein. Typically, biologically active portions comprise a domain or motif with at least one activity of the Lor-2 protein. A biologically active portion of a Lor-2 protein can be a polypeptide which is, for example, 10, 15, 25, 50, 100 or more amino acids in length. In another embodiment, a biologically active portion of a Lor-2 protein comprises a signal sequence and/or is secreted. In another embodiment, a biologically active portion of a Lor-2 protein lacks a signal sequence and/or is intracellular.

It is to be understood that a preferred biologically active portion of a Lor-2 protein of the present invention may contain at least one of the above-identified structural domains. A more preferred biologically active portion of a Lor-2 protein may contain at least two of the above-identified structural domains. Moreover, other biologically active portions, in which other regions of the protein are deleted, can be prepared by recombinant techniques and evaluated for one or more of the functional activities of a native Lor-2 protein.

In a preferred embodiment, the Lor-2 protein has an amino acid sequence shown in SEQ ID NO:2. In other embodiments, the Lor-2 protein is substantially homologous to the amino acid sequence shown in SEQ ID NO:2, and retains the functional activity of a protein having the amino acid sequence shown in SEQ ID NO:2, yet differs in amino acid sequence due to natural allelic variation or mutagenesis, as described in detail in subsection I above.

Accordingly, in another embodiment, the Lor-2 protein is a protein which comprises an amino acid sequence at least about 60%, 65%, 70%, 75%, 80%, 85%, 90%, 95%, 98%, 99%, or more homologous to the amino acid sequence of SEQ ID NO:2, and retains the functional activity of the Lor-2 proteins shown in SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the Lor-2 amino acid sequence of SEQ ID NO:2 having 753 amino acid residues, at least 300, preferably at least 400, more preferably at least 500, even more preferably at least 600, and even more preferably at least 650, 700 or 753 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989) which has been incorporated into the ALIGN program (version 2.0) (available at http://vega.igh.cnrs.fr/bin/align-guess.cgi), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to Lor-2 nucleic acid molecules of the invention. BLAST protein searches can be performed with the XBLAST program, score=50, wordlength=3 to obtain amino acid sequences homologous to Lor-2 protein molecules of the invention. To obtain gapped alignments for comparison purposes, Gapped BLAST can be utilized as described in Altschul et al., (1997) *Nucleic Acids Res.* 25(17) :3389–3402. When utilizing BLAST and Gapped BLAST programs, the default parameters of the respective programs (e.g., XBLAST and NBLAST) can be used. See http://www.ncbi.nlm.nih.gov.

The invention also provides Lor-2 chimeric or fusion proteins. As used herein, a Lor-2 "chimeric protein" or "fusion protein" comprises a Lor-2 polypeptide operatively linked to a non-Lor-2 polypeptide. A "Lor-2 polypeptide" refers to a polypeptide having an amino acid sequence corresponding to Lor-2, whereas a "non-Lor-2 polypeptide" refers to a polypeptide having an amino acid sequence corresponding to a protein which is not substantially homologous to the Lor-2 protein, e.g., a protein which is different from the Lor-2 protein and which is derived from the same or a different organism. Within a Lor-2 fusion protein the Lor-2 polypeptide can correspond to all or a portion of a Lor-2 protein. In a preferred embodiment, a Lor-2 fusion protein comprises at least one biologically active portion of a Lor-2 protein. In another preferred embodiment, a Lor-2 fusion protein comprises at least two biologically active portions of a Lor-2 protein. Within the fusion protein, the term "operatively linked" is intended to indicate that the Lor-2 polypeptide and the non-Lor-2 polypeptide are fused in-frame to each other. The non-Lor-2 polypeptide can be fused to the N-terminus or C-terminus of the Lor-2 polypeptide.

For example, in one embodiment, the fusion protein is a GST-Lor-2 fusion protein in which the Lor-2 sequences are fused to the C-terminus of the GST sequences. Such fusion proteins can facilitate the purification of recombinant Lor-2. In another embodiment, the fusion protein is a Lor-2 protein containing a heterologous signal sequence at its N-terminus. For example, the native murine Lor-2 signal sequence (i.e., about amino acids 1 to 25 of SEQ ID NO:2) can be removed and replaced with a signal sequence from another protein. In certain host cells (e.g., mammalian host cells), expression and/or secretion of Lor-2 can be increased through use of a heterologous signal sequence.

The Lor-2 fusion proteins of the invention can be incorporated into pharmaceutical compositions and administered to a subject in vivo. The Lor-2 fusion proteins can be used to affect the bioavailability of a Lor-2 target molecule. Use of Lor-2 fusion proteins may be useful therapeutically for the treatment of cardiovascular disorders (e.g., congestive heart failure). Moreover, the Lor-2-fusion proteins of the invention can be used as immunogens to produce anti-Lor-2 antibodies in a subject, to purify Lor-2 ligands and in screening assays to identify molecules which inhibit the interaction of Lor-2 with a Lor-2 target molecule.

Preferably, a Lor-2 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A Lor-2-encoding nucleic acid can be cloned into such an expression vector such that the fusion moiety is linked in-frame to the Lor-2 protein.

The present invention also pertains to variants of the Lor-2 proteins which function as either Lor-2 agonists (mimetics) or as Lor-2 antagonists. Variants of the Lor-2 proteins can be generated by mutagenesis, e.g., discrete point mutation or truncation of a Lor-2 protein. An agonist of the Lor-2 proteins can retain substantially the same, or a subset, of the biological activities of the naturally occurring form of a Lor-2 protein. An antagonist of a Lor-2 protein can inhibit one or more of the activities of the naturally occurring form of the Lor-2 protein by, for example, competitively inhibiting the protease activity of a Lor-2 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the Lor-2 protein.

In one embodiment, variants of a Lor-2 protein which function as either Lor-2 agonists (mimetics) or as Lor-2 antagonists can be identified by screening combinatorial libraries of mutants, e.g., truncation mutants, of a Lor-2 protein for Lor-2 protein agonist or antagonist activity. In one embodiment, a variegated library of Lor-2 variants is generated by combinatorial mutagenesis at the nucleic acid level and is encoded by a variegated gene library. A variegated library of Lor-2 variants can be produced by, for example, enzymatically ligating a mixture of synthetic oligonucleotides into gene sequences such that a degenerate set of potential Lor-2 sequences is expressible as individual polypeptides, or alternatively, as a set of larger fusion proteins (e.g., for phage display) containing the set of Lor-2 sequences therein. There are a variety of methods which can be used to produce libraries of potential Lor-2 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Lor-2 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a Lor-2 protein coding sequence can be used to generate a variegated population of Lor-2 fragments for screening and subsequent selection of variants of a Lor-2 protein. In one embodiment, a library of coding sequence fragments can be generated by treating a double stranded PCR fragment of a Lor-2 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, and internal fragments of various sizes of the Lor-2 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Lor-2 proteins. The most widely used techniques, which are amendable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify Lor-2 variants (Arkin and Yourvan (1992) *PNAS* 89:7811–7815; Delgrave et al. (1993) *Protein Engineering* 6(3):327–331).

In one embodiment, cell based assays can be exploited to analyze a variegated Lor-2 library. For example, a library of expression vectors can be transfected into a cell line which ordinarily synthesizes and secretes Lor-2. The transfected cells are then cultured such that Lor-2 and a particular mutant Lor-2 are secreted and the effect of expression of the mutant on Lor-2 activity in cell supernatants can be detected, e.g., by any of a number of enzymatic assays. Plasmid DNA can then be recovered from the cells which score for inhibition, or alternatively, potentiation of Lor-2 activity, and the individual clones further characterized.

An isolated Lor-2 protein, or a portion or fragment thereof, can be used as an immunogen to generate antibodies that bind Lor-2 using standard techniques for polyclonal and monoclonal antibody preparation. A full-length Lor-2 protein can be used or, alternatively, the invention provides antigenic peptide fragments of Lor-2 for use as immunogens. The antigenic peptide of Lor-2 comprises at least 8 amino acid residues of the amino acid sequence shown in SEQ ID NO:2 and encompasses an epitope of Lor-2 such that an antibody raised against the peptide forms a specific immune complex with Lor-2. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of Lor-2 that are located on the surface of the protein, e.g., hydrophilic regions, hydrophobic regions, alpha regions, beta regions, coil regions, turn regions, flexible regions, and antigenicity as shown in FIG. 4. In one embodiment, an antigenic peptide is included within amino acids 49–56 of SEQ ID NO:2. In another embodiment, an antigenic peptide is included within amino acids 291–305 of SEQ ID NO:2. In yet another embodiment, an antigenic peptide is included within amino acid 735–749 of SEQ ID NO:2.

A Lor-2 immunogen typically is used to prepare antibodies by immunizing a suitable subject, (e.g., rabbit, goat, mouse or other mammal) with the immunogen. An appropriate immunogenic preparation can contain, for example, recombinantly expressed Lor-2 protein or a chemically synthesized Lor-2 polypeptide. The preparation can further include an adjuvant, such as Freund's complete or incomplete adjuvant, or similar immunostimulatory agent. Immunization of a suitable subject with an immunogenic Lor-2 preparation induces a polyclonal anti-Lor-2 antibody response.

Accordingly, another aspect of the invention pertains to anti-Lor-2 antibodies. The term "antibody" as used herein refers to immunoglobulin molecules and immunologically active portions of immunoglobulin molecules, i.e., molecules that contain an antigen binding site which specifically binds (immunoreacts with) an antigen, such as Lor-2. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind Lor-2. The term "monoclonal antibody" or "monoclonal antibody composition", as used herein, refers to a population of antibody molecules that contain only one species of an antigen binding site capable of immunoreacting with a particular epitope of Lor-2. A monoclonal antibody composition thus typically displays a single binding affinity for a particular Lor-2 protein with which it immunoreacts.

Polyclonal anti-Lor-2 antibodies can be prepared as described above by immunizing a suitable subject with a Lor-2 immunogen. The anti-Lor-2 antibody titer in the immunized subject can be monitored over time by standard techniques, such as with an enzyme linked immunosorbent assay (ELISA) using immobilized Lor-2. If desired, the antibody molecules directed against Lor-2 can be isolated from the mammal (e.g., from the blood) and further purified by well known techniques, such as protein A chromatography to obtain the IgG fraction. At an appropriate time after immunization, e.g., when the anti-Lor-2 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Theraphy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36).

Alternative to preparing monoclonal antibody-secreting hybridomas, a monoclonal anti-Lor-2 antibody can be identified and isolated by screening a recombinant combinatorial immunoglobulin library (e.g, an antibody phage display library) with Lor-2 to thereby isolate immunoglobulin library members that bind Lor-2. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09197; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

Additionally, recombinant anti-Lor-2 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-Lor-2 antibody (e.g., monoclonal antibody) can be used to isolate Lor-2 by standard techniques, such as affinity chromatography or immunoprecipitation. An anti-Lor-2 antibody can facilitate the purification of natural Lor-2 from cells and of recombinantly produced Lor-2 expressed in host cells. Moreover, an anti-Lor-2 antibody can be used to detect Lor-2 protein (e.g., in a cellular lysate or cell supernatant) in order to evaluate the abundance and pattern of expression of the Lor-2 protein. Anti-Lor-2 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a Lor-2 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., Lor-2 proteins, mutant forms of Lor-2 proteins, fusion proteins, etc.).

The recombinant expression vectors of the invention can be designed for expression of Lor-2 proteins in prokaryotic or eukaryotic cells. For example, Lor-2 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in Lor-2 activity assays, (e.g., direct assays or competitive assays described in detail below), or to generate antibodies specific for Lor-2 proteins, for example. In a preferred embodiment, a Lor-2 fusion protein expressed in a retroviral expression vector of the present invention can be utilized to infect bone marrow cells which are subsequently transplanted into irradiated recipients. The pathology of the subject recipient is then examined after sufficient time has passed (e.g. six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn 1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the Lor-2 expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, Lor-2 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to Lor-2 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics,* Vol. 1(1) 1986.

Another aspect of the invention pertains to host cells into which a Lor-2 nucleic acid molecule of the invention is introduced, e.g., a Lor-2 nucleic acid molecule within a recombinant expression vector or a Lor-2 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a Lor-2 protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a Lor-2 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i. e., express) a Lor-2 protein. Accordingly, the invention further provides methods for producing a Lor-2 protein using the host cells of the invention. In one embodiment, the method comprises culturing the host cell of invention (into which a recombinant expression vector encoding a Lor-2 protein has been introduced) in a suitable medium such that a Lor-2 protein is produced. In another embodiment, the method further comprises isolating a Lor-2 protein from the medium or the host cell.

The host cells of the invention can also be used to produce nonhuman transgenic animals. For example, in one embodiment, a host cell of the invention is a fertilized oocyte or an embryonic stem cell into which Lor-2-coding sequences have been introduced. Such host cells can then be used to create non-human transgenic animals in which exogenous Lor-2 sequences have been introduced into their genome or homologous recombinant animals in which endogenous Lor-2 sequences have been altered. Such animals are useful for studying the function and/or activity of a Lor-2 and for identifying and/or evaluating modulators of Lor-2 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous Lor-2 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a Lor-2-encoding nucleic acid into the male pronuclei of a fertilized oocyte, e.g., by microinjection, retroviral infection, and allowing the oocyte to develop in a pseudopregnant female foster animal. The cDNA having the nucleotide sequence depicted in SEQ ID NO:1 can be introduced as a transgene into the genome of a non-human animal. Alternatively, a nonhuman homologue of a human Lor-2 gene, such as a mouse or rat Lor-2 gene, can be used as a transgene. Alternatively, a Lor-2 gene homologue, such as a Lor-2-1 gene can be isolated based on hybridization to the Lor-2 cDNA sequences shown in SEQ ID NO:1 and used as a transgene. Intronic sequences and polyadenylation signals can also be included in the transgene to increase the efficiency of expression of the transgene. A tissue-specific regulatory sequence(s) can be operably linked to a Lor-2 transgene to direct expression of a Lor-2 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of a Lor-2 transgene in its genome and/or expression of Lor-2 mRNA in tissues or cells of the animals. A transgenic founder animal can then be used to breed additional animals carrying the transgene. Moreover, transgenic animals carrying a transgene encoding a Lor-2 protein can further be bred to other transgenic animals carrying other transgenes.

To create a homologous recombinant animal, a vector is prepared which contains at least a portion of a Lor-2 gene into which a deletion, addition or substitution has been introduced to thereby alter, e.g., functionally disrupt, the Lor-2 gene. The Lor-2 gene can be a human gene, but more preferably, is a non-human homologue of a human Lor-2 gene (e.g., a cDNA isolated by stringent hybridization with the nucleotide sequence of SEQ ID NO:1). For example, a mouse Lor-2 gene can be used to construct a homologous recombination nucleic acid molecule, e.g., a vector, suitable for altering an endogenous Lor-2 gene in the mouse genome. In a preferred embodiment, the homologous recombination nucleic acid molecule is designed such that, upon homologous recombination, the endogenous Lor-2 gene is functionally disrupted (i.e., no longer encodes a functional protein; also referred to as a "knock out" vector). Alternatively, the homologous recombination nucleic acid molecule can be designed such that, upon homologous recombination, the endogenous Lor-2 gene is mutated or otherwise altered but still encodes functional protein (e.g., the upstream regulatory region can be altered to thereby alter the expression of the endogenous Lor-2 protein). In the homologous recombination nucleic acid molecule, the altered portion of the Lor-2 gene is flanked at its 5' and 3' ends by additional nucleic acid sequence of the Lor-2 gene to allow for homologous recombination to occur between the exogenous Lor-2 gene carried by the homologous recombination nucleic acid molecule and an endogenous Lor-2 gene in a cell, e.g., an embryonic stem cell. The additional flanking Lor-2 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced Lor-2 gene has homologously recombined with the endogenous Lor-2 gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach,* E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813. In brief, a cell, e.g., a somatic cell, from the transgenic animal can be isolated and induced to exit the growth cycle and enter $G_o$ phase. Alternatively, a cell, e.g., an embryonic stem cell, from the inner cell mass of a developing embryo can be transformed with a preferred transgene. Alternatively, a cell, e.g., a somatic cell, from cell culture line can be transformed with a preferred transgene and induced to exit the growth cycle and enter $G_o$ phase. The cell can then be fused, e.g., through the use of electrical pulses, to an enucleated mammalian oocyte. The reconstructed oocyte is then cultured such that it develops to morula or blastocyst and then transferred to pseudopregnant female foster animal. The offspring borne of this female foster animal will be a clone of the animal from which the nuclear donor cell, e.g., the somatic cell, is isolated.

IV. Pharmaceutical Compositions

The Lor-2 nucleic acid molecules, Lor-2 proteins, and anti-Lor-2 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, oral. Solutions or suspensions used for parenteral, application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a Lor-2 protein or anti-Lor-2 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

As described herein, a Lor-2 protein of the invention has one or more of the following activities: (i) interaction of a Lor-2 protein with a Lor-2 target molecule; (ii) interaction of a Lor-2 protein with a Lor-2 target molecule, wherein the Lor-2 target is a ligand; (iii) interaction of a Lor-2 protein with a Lor-2 target molecule, wherein the Lor-2 target is an extracellular matrix component (e.g., collagen or elastin); and (iv) modification of a Lor-2 target molecule (e.g., postranslational modification).

Further as described herein, a Lor-2 protein of the invention has one or more of the above activities and can thus be used in, for example: (1) crosslinking an extracellular matrix component; (2) regulating bone resorption; (3) regulating copper metabolism; (4) modulating maturation and/or stabilization of extracellular matrix components; (5) regulating cellular signaling; (6) regulating cellular adhesion; (7) regulating cardiac cellular processes; and (8) modulating a Lor-2-related disorder as defined herein.

The isolated nucleic acid molecules of the invention can be used, for example, to express Lor-2 protein (e.g., via a recombinant expression vector in a host cell in gene therapy applications), to detect Lor-2 mRNA (e.g., in a biological sample) or a genetic alteration in a Lor-2 gene, and to modulate Lor-2 activity, as described further below. The Lor-2 proteins can be used to treat disorders characterized by insufficient or excessive production of a Lor-2 or Lor-2 target molecules. In addition, the Lor-2 proteins can be used to screen for naturally occurring Lor-2 target molecules, to screen for drugs or compounds which modulate Lor-2 activity, as well as to treat disorders characterized by insufficient or excessive production of Lor-2 protein or production of Lor-2 protein forms which have decreased or aberrant activity compared to Lor-2 wild type protein. Moreover, the anti-Lor-2 antibodies of the invention can be used to detect and isolate Lor-2 proteins, regulate the bioavailability of Lor-2 proteins, and modulate Lor-2 activity.

Accordingly one embodiment of the present invention involves a method of use (e.g., a diagnostic assay, prognostic assay, or a prophylactic/therapeutic method of treatment) wherein a molecule of the present invention (e.g., a Lor-2 protein, Lor-2 nucleic acid, or a Lor-2 modulator) is used, for example, to diagnose, prognose and/or treat a disease and/or condition in which any of the aforementioned activities (i.e., activities (i)–(iv) and (1)–(7) in the above paragraph) is indicated. In another embodiment, the present invention involves a method of use (e.g., a diagnostic assay, prognostic assay, or a prophylactic/therapeutic method of treatment) wherein a molecule of the present invention (e.g., a Lor-2 protein, Lor-2 nucleic acid, or a Lor-2 modulator) is used, for example, for the diagnosis, prognosis, and/or treatment of subjects, preferably a human subject, in which any of the aforementioned activities is pathologically perturbed. In a preferred embodiment, the methods of use (e.g., diagnostic assays, prognostic assays, or prophylactic/ therapeutic methods of treatment) involve administering to a subject, preferably a human subject, a molecule of the present invention (e.g., a Lor-2 protein, Lor-2 nucleic acid, or a Lor-2 modulator) for the diagnosis, prognosis, and/or therapeutic treatment. In another embodiment, the methods of use (e.g, diagnostic assays, prognostic assays, or prophylactic/therapeutic methods of treatment) involve administering to a human subject a molecule of the present invention (e.g., a Lor-2 protein, Lor-2 nucleic acid, or a Lor-2 modulator).

A. Screening Assays:

The invention provides a method (also referred to herein as a "screening assay") for identifying modulators, i.e., candidate or test compounds or agents (e.g., peptides, peptidomimetics, small molecules or other drugs) which bind to Lor-2 proteins, have a stimulatory or inhibitory effect on, for example, Lor-2 expression or Lor-2 activity, or have a stimulatory or inhibitory effect on, for example, the activity of a Lor-2 target molecule.

In one embodiment, the invention provides assays for screening candidate or test compounds which are target molecules of a Lor-2 protein or polypeptide or biologically active portion thereof. In another embodiment, the invention provides assays for screening candidate or test compounds which bind to or modulate the activity of a Lor-2 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:1979; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. patent '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a Lor-2 protein or biologically active portion thereof is contacted with a test compound and the ability of the test compound to modulate Lor-2 activity determined. Determining the ability of the test compound to modulate Lor-2 activity can be accomplished by monitoring the bioactivity of the Lor-2 protein or biologically active portion thereof. The cell, for example, can be of mammalian origin or a yeast cell. In a preferred embodiment, the cell is a tumor cell (e.g., a cell isolated/cultured from a tumor or a tumor cell line). Determining the ability of the test compound to modulate Lor-2 activity can be accomplished, for example, by coupling the Lor-2 protein or biologically active portion thereof with a radioisotope or enzymatic label such that binding of the Lor-2 protein or biologically active portion thereof to its cognate target molecule can be determined by detecting the labeled Lor-2 protein or biologically active portion thereof in a complex. For example, compounds (e.g., Lor-2 protein or biologically active portion thereof) can be labeled with $_{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., Lor-2 protein or biologically active portion thereof) to interact with its cognate target molecule without the labeling of any of the interactants. For example, a microphysiometer can be used to detect the interaction of a compound with its cognate target molecule without the labeling of either the compound or the receptor. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, the assay comprises contacting a cell which expresses a Lor-2 protein or biologically active portion thereof, with a target molecule to form an assay mixture, contacting the assay mixture with a test compound, and determining the ability of the test compound to modulate the activity of the Lor-2 protein or biologically active portion thereof, wherein determining the ability of the test compound to modulate the activity of the Lor-2 protein or biologically active portion thereof, comprises determining the ability of the test compound to modulate a biological activity of the Lor-2 expressing cell (e.g., determining the ability of the test compound to modulate a Lor-2-related activity as defined herein).

In another preferred embodiment, the assay comprises contacting a cell which is responsive to a Lor-2 protein or biologically active portion thereof, with a Lor-2 protein or biologically-active portion thereof, to form an assay mixture, contacting the assay mixture with a test compound, and determining the ability of the test compound to modulate the activity of the Lor-2 protein or biologically active portion thereof, wherein determining the ability of the test compound to modulate the activity of the Lor-2 protein or biologically active portion thereof comprises determining the ability of the test compound to modulate a biological activity of the Lor-2-responsive cell (e.g., determining the ability of the test compound to modulate a Lor-2-related activity as defined herein).

In another embodiment, an assay is a cell-based assay comprising contacting a cell expressing a Lor-2 target molecule with a test compound and determining the ability of the test compound to modulate (e.g. stimulate or inhibit) the activity of the Lor-2 target molecule. Determining the ability of the test compound to modulate the activity of a Lor-2 target molecule can be accomplished, for example, by determining the ability of the Lor-2 protein to bind to or interact with the Lor-2 target molecule.

Determining the ability of the Lor-2 protein to bind to or interact with a Lor-2 target molecule can be accomplished by one of the methods described above for determining direct binding. In a preferred embodiment, determining the ability of the Lor-2 protein to bind to or interact with a Lor-2 target molecule can be accomplished by determining the activity of the target molecule. For example, the activity of the target molecule can be determined by detecting dephosphorylation of a phosphorylated protein. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a Lor-2 protein or biologically active portion thereof (e.g., a portion comprising at least one, two, three or four SRCR domains) is contacted with a test compound and the ability of the test compound to bind to the Lor-2 protein or biologically active portion thereof is determined. Binding of the test compound to the Lor-2 protein can be determined either directly or indirectly as described above (e.g., labeled test compounds, for example, tritiated test compounds). In a preferred embodiment, the assay includes contacting the Lor-2 protein or biologically active portion thereof with a known compound which binds Lor-2 (e.g., a Lor-2 target molecule) to form an assay mixture, contacting the assay mixture with a test compound, and determining the ability of the test compound to interact with a Lor-2 protein, wherein determining the ability of the test compound to interact with a Lor-2 protein comprises determining the ability of the test compound to preferentially bind to Lor-2 or biologically active portion thereof as compared to the known compound.

In another embodiment, the assay is a cell-free assay in which a Lor-2 protein or biologically active portion thereof is contacted with a test compound and the ability of the test compound to modulate (e.g., stimulate or inhibit) the activity of the Lor-2 protein or biologically active portion thereof is determined. For example, a cell-free assay of the present invention can feature a LOX domain or LOX-related region which is contacted with a test compound and the ability of the test compound to modulate an enzymatic activity of Lor-2 determined. Determining the ability of the test compound to modulate the activity of a Lor-2 protein can be accomplished, for example, by determining the ability of the Lor-2 protein to bind to a Lor-2 target molecule by one of the methods described above for determining direct binding. Determining the ability of the Lor-2 protein to bind to a Lor-2 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a Lor-2 protein can be accomplished by determining the ability of the Lor-2 protein to further modulate the activity of a downstream effector (e.g., a transcriptionally activated cardiovascular-related pathway component) of a Lor-2 target molecule. For example, the activity of the effector molecule on an appropriate target can be determined or the binding of the effector to an appropriate target can be determined as previously described.

In yet another embodiment, the cell-free assay involves contacting a Lor-2 protein or biologically active portion thereof with a known compound which binds the Lor-2 protein to form an assay mixture, contacting the assay mixture with a test compound, and determining the ability of the test compound to interact with the Lor-2 protein, wherein determining the ability of the test compound to interact with the Lor-2 protein comprises determining the ability of the Lor-2 protein to preferentially bind to or modulate the activity of a Lor-2 target molecule.

The cell-free assays of the present invention are amenable to use of both soluble and/or membrane-bound forms of isolated proteins (e.g. Lor-2 proteins or biologically active portions thereof or receptors to which Lor-2 targets bind). In the case of cell-free assays in which a membrane-bound form of an isolated protein is used (e.g., a cell surface receptor) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N, N-dimethyl-3-ammonio-1-propane sulfonate.

In more than one embodiment of the above assay methods of the present invention, it may be desirable to immobilize either Lor-2 or its target molecule to facilitate separation of complexed from uncomplexed forms of one or both of the proteins, as well as to accommodate automation of the assay. Binding of a test compound to a Lor-2 protein, or interaction of a Lor-2 protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/Lor-2 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or Lor-2 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of Lor-2 binding or activity determined using standard techniques.

Other techniques for immobilizing proteins on matrices can also be used in the screening assays of the invention. For example, either a Lor-2 protein or a Lor-2 target molecule can be immobilized utilizing conjugation of biotin and streptavidin. Biotinylated Lor-2 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with Lor-2 protein or target molecules but which do not interfere with binding of the Lor-2 protein to its target molecule can be derivatized to the wells of the plate, and unbound target or Lor-2 protein trapped in the wells by antibody conjugation. Methods for detecting such complexes, in addition to those described above for the GST-immobilized complexes, include immunodetection of complexes using antibodies reactive with the Lor-2 protein or target molecule, as well as enzyme-linked assays which rely on detecting an enzymatic activity associated with the Lor-2 protein or target molecule.

In another embodiment, modulators of Lor-2 expression are identified in a method wherein a cell is contacted with a candidate compound and the expression of Lor-2 mRNA or protein in the cell is determined. The level of expression of Lor-2 mRNA or protein in the presence of the candidate compound is compared to the level of expression of Lor-2 mRNA or protein in the absence of the candidate compound. The candidate compound can then be identified as a modulator of Lor-2 expression based on this comparison. For example, when expression of Lor-2 mRNA or protein is greater (statistically significantly greater) in the presence of the candidate compound than in its absence, the candidate compound is identified as a stimulator of Lor-2 mRNA or protein expression. Alternatively, when expression of Lor-2 mRNA or protein is less (statistically significantly less) in the presence of the candidate compound than in its absence, the candidate compound is identified as an inhibitor of Lor-2 mRNA or protein expression. The level of Lor-2 mRNA or protein expression in the cells can be determined by methods described herein for detecting Lor-2 mRNA or protein.

In yet another aspect of the invention, the Lor-2 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with Lor-2 ("Lor-2-binding proteins" or "Lor-2-bp") and are involved in Lor-2 activity. Such Lor-2-binding proteins are also likely to be involved in the propagation of signals by the Lor-2 proteins or Lor-2 targets as, for example, downstream elements of a Lor-2-mediated signaling pathway. Alternatively, such Lor-2-binding proteins are likely to be Lor-2 inhibitors.

The two-hybrid system is based on the modular nature of most transcription factors, which consist of separable DNA-binding and activation domains. Briefly, the assay utilizes two different DNA constructs. In one construct, the gene that codes for a Lor-2 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Lor-2-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Lor-2 protein.

This invention further pertains to novel agents identified by the above-described screening assays and to processes for producing such agents by use of these assays. Accordingly, in one embodiment, the present invention includes a compound or agent obtainable by a method comprising the steps of any one of the aformentioned screening assays (e.g., cell-based assays or cell-free assays). For example, in one embodiment, the invention includes a compound or agent obtainable by a method comprising contacting a cell which expresses Lor-2 with a test compound and the determining the ability of the test compound to bind to, or modulate the activity of, or expression of, the Lor-2 target molecule. In another embodiment, the invention includes a compound or agent obtainable by a method comprising contacting a cell which expresses a Lor-2 target molecule with a test compound and the determining the ability of the test compound to bind to, or modulate the activity of, or expression of, the Lor-2 target molecule.

In another embodiment, the invention includes a compound or agent obtainable by a method comprising contacting a Lor-2 target molecule with a Lor-2 protein or biologically-active portion thereof, to form an assay mixture, contacting the assay mixture with a test compound, and determining the ability of the test compound to interact with, or modulate the activity of, the Lor-2 target molecule. In another embodiment, the invention includes a compound or agent obtainable by a method comprising contacting a Lor-2 protein or biologically active portion thereof with a test compound and determining the ability of the test compound to bind to, or modulate (e.g, stimulate or inhibit) the activity of, the Lor-2 protein or biologically active portion thereof. In yet another embodiment, the present invention includes a compound or agent obtainable by a method comprising contacting a Lor-2 protein or biologically active portion thereof with a known compound which binds the Lor-2 protein to form an assay mixture, contacting the assay mixture with a test compound, and determining the ability of the test compound to interact with, or modulate the activity of the Lor-2 protein.

Accordingly, it is within the scope of this invention to further use an agent identified as described herein in an appropriate animal model. For example, an agent identified as described herein (e.g., a Lor-2 modulating agent, an antisense Lor-2 nucleic acid molecule, a Lor-2-specific antibody, or a Lor-2-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The present invention also pertains to uses of novel agents identified by the above-described screening assays for diagnoses, prognoses, and treatments as described herein. Accordingly, it is within the scope of the present invention to use such agents in the design, formulation, synthesis, manufacture, and/or production of a drug or pharmaceutical composition for use in diagnosis, prognosis, or treatment, as described herein. For example, in one embodiment, the present invention includes a method of synthesizing or producing a drug or pharmaceutical composition by reference to the structure and/or properties of a compound obtainable by one of the above-described screening assays. For example, a drug or pharmaceutical composition can be synthesized based on the structure and/or properties of a compound obtained by a method in which a cell which expresses Lor-2 (or a Lor-2 target molecule) is contacted with a test compound and the ability of the test compound to bind to, or modulate the activity of, the Lor-2 (or Lor-2 target molecule) is determined. In another exemplary embodiment, the present invention includes a method of synthesizing or producing a drug or pharmaceutical composition based on the structure and/or properties of a compound obtainable by a method in which a Lor-2 protein or biologically active portion thereof is contacted with a test compound and the ability of the test compound to bind to, or modulate (e.g., stimulate or inhibit) the activity of, the Lor-2 protein or biologically active portion thereof is determined.

In a preferred embodiment, the present invention includes a method or process for producing a drug, pharmaceutical compound or pharmaceutical composition comprising identifying a compound or agent which modulates (e.g., activates, inhibits, mimics, etc.) the expression or activity of a Lor-2 protein or Lor-2 target molecule and modifying the compound or agent such that a drug, pharmaceutical compound or pharmaceutical composition is produced. In another embodiment, the present invention includes a method or process for producing a drug, pharmaceutical compound or pharmaceutical composition comprising identifying a compound or agent which modulates (e.g., activates, inhibits, mimics, etc.) the expression or activity of a Lor-2 protein or Lor-2 target molecule, synthesizing the compound or agent so-identified and modifying the compound or agent such that a drug, pharmaceutical compound or pharmaceutical composition is produced. Modifying the compound or agent so-identified can include, for example, changing (e.g., altering or deriviting) the compound or agent such that the compound or agent is better suited for administration to a subject. For example, the compound or agent can be modified according to routine medicinal chemistry practices to achieve greater stability (e.g., longer half-life) upon administration, increased solubility (e.g., in a pharmaceutically acceptable carrier), better absorption, reduced side effects, ease of administration, and the like. Drugs, pharmaceutical compounds and pharmaceutical compositions so-formulated are also intended to be within the scope of the present invention.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the Lor-2 nucleotide sequences, described herein, can be used to map the location of the Lor-2 genes on a chromosome. The mapping of the Lor-2 sequences to chromosomes is an important first step in correlating these sequences with genes associated with disease.

Briefly, Lor-2 genes can be mapped to chromosomes by preparing PCR primers (preferably 15–25 bp in length) from the Lor-2 nucleotide sequences. Computer analysis of the Lor-2 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the Lor-2 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the Lor-2 nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *PNAS*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the Lor-2 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The Lor-2 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the Lor-2 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The Lor-2 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:1 are used, a more appropriate number of primers for positive individual identification would be 500–2,000.

If a panel of reagents from Lor-2 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial Lor-2 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the Lor-2 nucleotide sequences or portions thereof, e.g., fragments derived from the noncoding regions of SEQ ID NO:1 having a length of at least 20 bases, preferably at least 30 bases.

The Lor-2 nucleotide sequences described herein can further be used to provide polynucleotide reagents, e.g., labeled or labelable probes which can be used in, for example, an in situ hybridization technique, to identify a specific tissue, e.g., cardiovascular tissue. This can be very useful in cases where a forensic pathologist is presented with a tissue of unknown origin. Panels of such Lor-2 probes can be used to identify tissue by species and/or by organ type, e.g., heart.

In a similar fashion, these reagents, e.g., Lor-2 primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining Lor-2 protein and/or nucleic acid expression as well as Lor-2 activity, in the context of a biological sample (e.g., blood, serum, cells, tissue, e.g., heart) to thereby determine whether an individual is afflicted with a disease or disorder, or is at risk of developing a disorder, associated with aberrant Lor-2 expression or activity. The invention also provides for prognostic (or predictive) assays for determining whether an individual is at risk of developing a disorder associated with Lor-2 protein, nucleic acid expression or activity. For example, mutations in a Lor-2 gene can be assayed in a biological sample. Alternatively, the presence of Lor-2 expression and/or activity can be used in determining whether a person is at risk of having a tumor or at risk of having a tumor metastasize. Such assays can be used for prognostic or predictive purpose to thereby phophylactically treat an individual prior to the onset or progression of a disorder characterized by or associated with Lor-2 protein, nucleic acid expression or activity (e.g., tumor progression). In another example, the invention provides methods of determining the metastatic potential of a tumor.

Another aspect of the invention pertains to monitoring the influence of agents (e.g., drugs, compounds) on the expression or activity of Lor-2 in clinical trials.

These and other agents are described in further detail in the following sections.

1. Diagnostic Assays

An exemplary method for detecting the presence or absence of Lor-2 protein or nucleic acid in a biological sample involves obtaining a biological sample from a test subject and contacting the biological sample with a compound or an agent capable of detecting Lor-2 protein or nucleic acid (e.g., mRNA, genomic DNA) that encodes Lor-2 protein such that the presence of Lor-2 protein or nucleic acid is detected in the biological sample. A preferred agent for detecting Lor-2 mRNA or genomic DNA is a labeled nucleic acid probe capable of hybridizing to Lor-2 mRNA or genomic DNA. The nucleic acid probe can be, for example, a full-length Lor-2 nucleic acid, such as the nucleic acid of SEQ ID NO:1, such as an oligonucleotide of at least 15, 30, 50, 100, 250 or 500 nucleotides in length and sufficient to specifically hybridize under stringent conditions to Lor-2 mRNA or genomic DNA. Other suitable probes for use in the diagnostic assays of the invention are described herein.

A preferred agent for detecting Lor-2 protein is an antibody capable of binding to Lor-2 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect Lor-2 mRNA, protein, or genomic DNA in a biological sample in vitro as well as in vivo. For example, in vitro techniques for detection of Lor-2 mRNA include Northern hybridizations and in situ hybridizations. In vitro techniques for detection of Lor-2 protein include enzyme linked immunosorbent assays (ELISAs), Western blots, immunoprecipitations and immunofluorescence. In vitro techniques for detection of Lor-2 genomic DNA include Southern hybridizations. Furthermore, in vivo techniques for detection of Lor-2 protein include introducing into a subject a labeled anti-Lor-2 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. Preferred biological samples are from serum, or heart tissue, isolated by conventional means from a subject. Also preferred are biological samples from tumors (e.g., tumor biopsies). Additional preferred biological samples include prostate tissue, liver tissue, breast tissue, skeletal muscle tissue, brain tissue, colon tissue, heart tissue, ovarian tissue, kidney tissue, lung tissue, vascular tissue, aortic tissue, thyroid tissue, placental tissue, intestinal tissue, cervical tissue, splenic tissue, esophageal tissue, thymic tissue, tonsillar tissue, lymph nodes and osteogenic cells. A particularly preferred sample is from breast tissue.

In another embodiment, the methods further involve obtaining a control biological sample from a control subject, contacting the control sample with a compound or agent capable of detecting Lor-2 protein, mRNA, or genomic DNA, such that the presence of Lor-2 protein, mRNA or genomic DNA is detected in the biological sample, and comparing the presence of Lor-2 protein, mRNA or genomic DNA in the control sample with the presence of Lor-2 protein, mRNA or genomic DNA in the test sample. In one embodiment, increased levels of Lor-2 protein, mRNA or DNA (e.g., cDNA or genomic DNA) in the test sample as compared to the control sample is determinative or predictive of a Lor-2-related aberrancy (e.g., a proliferative disorder of disease, for example, cancer). For example, 2-fold levels of expression of Lor-2 in the test sample as compared to the control sample may be determinative or predictive of a Lor-2-related aberrancy. Preferably, 5-fold, 10-fold, 100-fold, 500-fold or 1000-fold levels of expression of Lor-2 in the test sample as compared to the control sample may be determinative or predictive of a Lor-2-related aberrancy.

The invention also encompasses kits for detecting the presence of Lor-2 in a biological sample. For example, the kit can comprise a labeled compound or agent capable of detecting Lor-2 protein or mRNA in a biological sample; means for determining the amount of Lor-2 in the sample; and means for comparing the amount of Lor-2 in the sample with a standard. The compound or agent can be packaged in a suitable container. The kit can further comprise instructions for using the kit to detect Lor-2 protein or nucleic acid.

2. Prognostic Assays

The diagnostic methods described herein can furthermore be utilized to identify subjects having or at risk of developing a disease or disorder associated with aberrant Lor-2 expression or activity. As used herein, the term "aberrant" includes a Lor-2 expression or activity which deviates from the wild type Lor-2 expression or activity. Aberrant expression or activity includes increased or decreased expression or activity, as well as expression or activity which does not follow the wild type developmental pattern of expression or the subcellular pattern of expression. For example, aberrant Lor-2 expression or activity is intended to include the cases in which a mutation in the Lor-2 gene causes the Lor-2 gene to be under-expressed or over-expressed and situations in which such mutations result in a non-functional Lor-2 protein or a protein which does not function in a wild-type fashion, e.g., a protein which does not interact with a Lor-2 ligand or one which interacts with a non-Lor-2 ligand.

The assays described herein, such as the preceding diagnostic assays or the following assays, can be utilized to identify subjects having or at risk of developing a disease or disorder associated with aberrant Lor-2 expression or activity. For example, the assays described herein, such as the preceding diagnostic assays or the following assays, can be utilized to identify a subject having or at risk of developing a disorder associated with Lor-2 protein, nucleic acid expression or activity such a cardiovascular disorder (e.g., congestive heart failure). Alternatively, the prognostic assays can be utilized to identify a subject having or at risk for developing a cardiovascular disorder. Thus, the present invention provides a method for identifying a disease or disorder associated with aberrant Lor-2 expression or activity in which a test sample is obtained from a subject and Lor-2 protein or nucleic acid (e.g., mRNA, genomic DNA) is detected, wherein the presence of Lor-2 protein or nucleic acid is diagnostic for a subject having or at risk of developing a disease or disorder associated with aberrant Lor-2 expression or activity. As used herein, a "test sample" refers to a biological sample obtained from a subject of interest. For example, a test sample can be a biological fluid (e.g., serum), cell sample, or tissue (e.g., heart).

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant Lor-2 expression or activity. For example, such methods can be used to determine whether a subject can be effectively treated with an agent for a cardiovascular disorder (e.g., congestive heart failure). For example, such methods can be used to determine whether a subject can be effectively treated with an agent for a cardiovascular disorder. Thus, the present invention provides methods for determining whether a subject can be effectively treated with an agent for a disorder associated with aberrant Lor-2 expression or activity in which a test sample is obtained and Lor-2 protein or nucleic acid expression or activity is detected (e.g., wherein the abundance of Lor-2 protein or nucleic acid expression or activity is diagnostic for a subject that can be administered the agent to treat a disorder associated with aberrant Lor-2 expression or activity.)

The methods of the invention can also be used to detect genetic alterations in a Lor-2 gene, thereby determining if a subject with the altered gene is at risk for a disorder characterized by aberrant cardiovascular development. In preferred embodiments, the methods include detecting, in a sample of cells from the subject, the presence or absence of a genetic alteration characterized by at least one of an alteration affecting the integrity of a gene encoding a Lor-2-protein, or the mis-expression of the Lor-2 gene. For example, such genetic alterations can be detected by ascertaining the existence of at least one of 1) a deletion of one or more nucleotides from a Lor-2 gene; 2) an addition of one or more nucleotides to a Lor-2 gene; 3) a substitution of one or more nucleotides of a Lor-2 gene, 4) a chromosomal rearrangement of a Lor-2 gene; 5) an alteration in the level of a messenger RNA transcript of a Lor-2 gene, 6) aberrant modification of a Lor-2 gene, such as of the methylation pattern of the genomic DNA, 7) the presence of a non-wild type splicing pattern of a messenger RNA transcript of a Lor-2 gene, 8) a non-wild type level of a Lor-2-protein, 9) allelic loss of a Lor-2 gene, and 10) inappropriate post-translational modification of a Lor-2-protein. As described herein, there are a large number of assay techniques known in the art which can be used for detecting alterations in a Lor-2 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the Lor-2-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a Lor-2 gene under conditions such that hybridization and amplification of the Lor-2-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et all, 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Lor-2 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Lor-2 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in Lor-2 can be identified in two dimensional arrays containing light-generated DNA probes as described in Cronin, M. T. et al, supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Lor-2 gene and detect mutations by comparing the sequence of the sample Lor-2 with the corresponding wild-type (control) sequence. Examples of sequencing reactions include those based on techniques developed by Maxim and Gilbert ((1977) *PNAS* 74:560) or Sanger ((1977) *PNAS*

74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the Lor-2 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type Lor-2 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Lor-2 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a Lor-2 sequence, e.g., a wild-type Lor-2 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Lor-2 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat Res* 285:125–144; and Hayashi (1992) *Genet Anal Tech Appl* 9:73–79). Single-stranded DNA fragments of sample and control Lor-2 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Lor-2 gene.

Furthermore, any cell type or tissue in which Lor-2 is expressed may be utilized in the prognostic assays described herein.

3. Monitoring of Effects During Clinical Trials

Monitoring the influence of agents (e.g., drugs, compounds) on the expression or activity of a Lor-2 protein (e.g., modulation of cardiovascular performance) can be applied not only in basic drug screening, but also in clinical trials. For example, the effectiveness of an agent determined by a screening assay as described herein to increase Lor-2 gene expression, protein levels, or upregulate Lor-2 activity, can be monitored in clinical trials of subjects exhibiting decreased Lor-2 gene expression, protein levels, or downregulated Lor-2 activity. Alternatively, the effectiveness of an agent determined by a screening assay to decrease Lor-2 gene expression, protein levels, or downregulate Lor-2 activity, can be monitored in clinical trials of subjects exhibiting increased Lor-2 gene expression, protein levels, or upregulated Lor-2 activity. In such clinical trials, the expression or activity of a Lor-2 gene, and preferably, other genes that have been implicated in, for example, a developmental disorder can be used as a "read out" or markers of the phenotype of a particular cell.

For example, and not by way of limitation, genes, including Lor-2, that are modulated in cells by treatment with an agent (e.g, compound, drug or small molecule) which modulates Lor-2 activity (e.g, identified in a screening assay as described herein) can be identified. Thus, to study the effect of agents on cardiovascular disorders, for example, in a clinical trial, cells can be isolated and RNA prepared and analyzed for the levels of expression of Lor-2 and other genes implicated in a cardiovascular disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of Lor-2 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a Lor-2 protein, mRNA, or genomic DNA in the preadministration sample; (iii) obtaining one or more post-administration samples from the subject; (iv) detecting the level of expression or activity of the Lor-2 protein, mRNA, or genomic DNA in the post-administration samples; (v) comparing the level of expression or activity of the Lor-2 protein, mRNA, or genomic DNA in the pre-administration sample with the Lor-2 protein, mRNA, or genomic DNA in the post administration sample or samples; and (vi) altering the administration of the agent to the subject accordingly. For example, increased administration of the agent may be desirable to increase the expression or activity of Lor-2 to higher levels than detected, i.e., to increase the effectiveness of the agent. Alternatively, decreased administration of the agent may be desirable to decrease expression or activity of Lor-2 to lower levels than detected, i.e. to decrease the effectiveness of the agent. According to such an embodiment, Lor-2 expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant Lor-2 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the Lor-2 molecules of the present invention or Lor-2 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant Lor-2 expression or activity, by administering to the subject a Lor-2 or an agent which modulates Lor-2 expression or at least one Lor-2 activity. Subjects at risk for a disease which is caused or contributed to by aberrant Lor-2 expression or activity can be identified by, for example, any or a combination of diagnostic or prognostic assays as described herein. Administration of a prophylactic agent can occur prior to the manifestation of symptoms characteristic of the Lor-2 aberrance, such that a disease or disorder is prevented or, alternatively, delayed in its progression. Depending on the type of Lor-2 aberrancy, for example, a Lor-2, Lor-2 agonist or Lor-2 antagonist agent can be used for treating the subject. The appropriate agent can be determined based on screening assays described herein. The prophylactic methods of the present invention are further discussed in the following subsections.

2. Therapeutic Methods

Another aspect of the invention pertains to methods of modulating Lor-2 expression or activity for therapeutic purposes. Accordingly, in an exemplary embodiment, the modulatory method of the invention involves contacting a cell with a Lor-2 or agent that modulates one or more of the activities of Lor-2 protein activity associated with the cell. An agent that modulates Lor-2 protein activity can be an agent as described herein, such as a nucleic acid or a protein, a naturally-occurring target molecule of a Lor-2 protein, a Lor-2 antibody, a Lor-2 agonist or antagonist, a peptidomimetic of a Lor-2 agonist or antagonist, or other small molecule. In one embodiment, the agent stimulates one or more Lor-2 activities. Examples of such stimulatory agents include active Lor-2 protein and a nucleic acid molecule encoding Lor-2 that has been introduced into the cell. In another embodiment, the agent inhibits one or more Lor-2 activities. Examples of such inhibitory agents include antisense Lor-2 nucleic acid molecules, anti-Lor-2 antibodies, and Lor-2 inhibitors. These modulatory methods can be performed in vitro (e.g., by culturing the cell with the agent), in vivo (e.g., by administering the agent to a subject), or alternatively in situ (e.g., at the site of lesion or injury). As such, the present invention provides methods of treating an individual afflicted with a disease or disorder characterized by aberrant expression or activity of a Lor-2 protein or nucleic acid molecule. In one embodiment, the method involves administering an agent (e.g., an agent identified by a screening assay described herein), or combination of agents that modulates (e.g., upregulates or downregulates) Lor-2 expression or activity. In another embodiment, the method involves administering a Lor-2 protein or nucleic acid molecule as therapy to compensate for reduced or aberrant Lor-2 expression or activity.

Stimulation of Lor-2 activity is desirable in situations in which Lor-2 is abnormally downregulated and/or in which increased Lor-2 activity is likely to have a beneficial effect. For example, stimulation of Lor-2 activity is desirable in situations in which a Lor-2 is downregulated and/or in which increased Lor-2 activity is likely to have a beneficial effect. Likewise, inhibition of Lor-2 activity is desirable in situations in which Lor-2 is abnormally upregulated and/or in which decreased Lor-2 activity is likely to have a beneficial effect.

3. Pharmacogenomics

The Lor-2 molecules of the present invention, as well as agents, or modulators which have a stimulatory or inhibitory effect on Lor-2 activity (e.g., Lor-2 gene expression) as identified by a screening assay described herein can be administered to individuals to treat (prophylactically or therapeutically) disorders associated with aberrant Lor-2 activity (e.g., proliferative disorders, for example, cancer). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a Lor-2 molecule or Lor-2 modulator as well as tailoring the dosage and/or therapeutic regimen of treatment with a Lor-2 molecule or Lor-2 modulator.

Pharmacogenomics deals with clinically significant hereditary variations in the response to drugs due to altered drug disposition and abnormal action in affected persons. See e.g., Eichelbaum, M., *Clin Exp Pharmacol Physiol*, 1996, 23(10–11):983–985 and Linder, M. W., *Clin Chem*, 1977, 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a Lor-2 protein or Lor-2 receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g, N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a Lor-2 molecule or Lor-2 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a Lor-2 molecule or Lor-2 modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLE 1

Identification and Characterization of Human Lor-2 cDNA

In this example, the identification and characterization of the gene encoding human Lor-2 (i.e., Lysyl Oxidase Related-2, also referred to as Myocardium Secreted Protein-18 or "MSP-18") is described.

Isolation of the Human Lor-2 cDNA

The invention is based, at least in part, on the discovery of the human gene encoding Lor-2. Human Lor-2 was isolated from a cDNA library which was prepared from tissue obtained from subjects suffering from congestive heart failure. Briefly, a cardiac tissue sample was obtained from a biopsy of a 42 year old woman suffering from congestive heart failure. mRNA was isolated from the cardiac tissue and a cDNA library was prepared therefrom using art-known methods (described in, for example, *Molecular Cloning A Laboratory Manual*, 2nd Ed., ed. by Sambrook, Fritsch and Maniatis (Cold Spring Harbor Laboratory Press: 1989). Using a program which identifies the presence of signal peptides (Nielsen, H. et al. (1997) *Protein Engineering* 10:1–6) a positive clone was isolated.

The sequence of the positive clone was determined and found to contain an open reading frame. The nucleotide sequence encoding the human Lor-2 protein comprises about 2920 nucleic acids, and has the nucleotide sequence shown in FIG. 1 and set forth as SEQ ID NO:1. The protein encoded by this nucleic acid comprises about 753 amino acids, and has the amino acid sequence shown in FIG. 1 and set forth as SEQ ID NO:2.

Analysis of Human Lor-2

A BLAST search (Altschul et al. (1990) *J Mol. Biol.* 215:403) of the nucleotide and protein sequences of human Lor-2 revealed that Lor-2 is similar to the following protein molecules: a human lysyl oxidase-related protein (Accession No. U89942) having approximately 56.9% identity over amino acids 33–752 of Lor-2 (SEQ ID NO:2); and a second murine lysyl-oxidase related protein; (Accession No.AF053368) having approximately 92.6% identity over amino acids 1–753, e.g., over the entire length) of Lor-2 (SEQ ID NO:2). (Identities were calculated using the LALIGN algorithm of Huang and Miller (1991) *Adv. Appl. Math.* 12:373–381).

The Lor-2 protein is predicted to have a signal peptide from amino acid residues 1–25 of SEQ ID NO:2. Accordingly, a mature Lor-2 protein is predicted to include amino acid residues 26–753 of SEQ ID NO:2. Lor-2 is also predicted to have 5 N-glycosylation sites, 8 protein kinase phosphorylation ("PKC") sites, 14 casein kinase II phosphorylation sites, 19 N-myristoylation sites, and 1 amidation site. Predicted N-glycosylation sites are found, for example, from about amino acid 111–114, 266–269, 390–393, 481–484, and 625–628 of SEQ ID NO:2. Predicted PKC phosphorylation sites are found, for example, from about amino acid 97–99, 104–106, 221–223, 268–270, 352–354, 510–512, 564–566, and 649–651 of SEQ ID NO:2. Predicted casein kinase II phosphorylation sites are found, for example, from about amino acid 31–34, 68–71, 115–118, 120–123, 135–138, 330–333, 352–355, 377–380, 392–395, 411–414, 424–427, 493–496, 527–530, and 617–620 of SEQ ID NO:2. Predicted N-myristoylation sites are found, for example, from about amino acids 13–18, 116–121, 130–135, 273–278, 312–317, 359–364, 378–383, 403–408, 443–448, 451–456, 463–468, 470–475, 489–494, 506–511, 515–520, 521–526, 626–631, 661–666, and 746–751 of SEQ ID NO:2. A predicted amidation site is found, for example, from amino acid 117–180 of SEQ ID NO:2.

Moreover, Lor-2 has a 4 scavenger receptor cysteine-rich domains from amino acid residues 51–145, 183–282, 310–407, and 420–525 of SEQ ID NO:2. The third scavenger receptor cysteine-rich domain includes a speract receptor repeated domain signature from amino acid residues 312–349 of SEQ ID NO:2. Lor-2 further has a lysyl oxidase domain from residues 330–732 of SEQ ID NO:2. (See, for example, FIG. 5). Within the lysyl oxidase domain of Lor-2, there exists a fragment having significant homology to the lysyl oxidase putative copper-binding region, termed the "copper-binding talon". A prosite consensus pattern describing the copper-binding talon is as follows: W-E-W-H-S-C-H-Q-H-Y-H (SEQ ID NO:9) (see also PROSITE documentation PDOC00716 and Krebs and Krawetz (1993) *Biochem. Biophys. Acta* 1202:7–12). Amino acid residues 601–701 of human Lor-2 (SEQ ID NO:2) have ~73% identity with this consensus sequence (8/11 residues) including each of the four conserved histidines, three of which are believed to be copper ligands residing within an octahedral coordination complex of lysyl oxidase.

Analysis of primary and secondary protein structures, as shown in FIG. 4, was performed as follows: alpha, beta turn and coil regions, Garnier-Robson algorithm (Garnier et al. (1978) *J Mol Biol* 120:97); alpha, beta, and turn regions, Chou-Fasman algorithm (Chou and Fasman (1978) *Adv in Enzymol Mol* 47:45–148); hydrophilicity and hydrophobicity plots, Kyte-Doolittle algorithm (Kyte and Doolittle (1982) *J Mol Biol* 157:105–132); alpha amphipathic and beta amphipathic regions, Eisenberg algorithm (Eisenberg et al. (1982) *Nature* 299:371–374); flexible regions, Karplus-Schulz algorithm (Karplus and Schulz (1985) *Naturwissens-Chafen* 72:212–213); antigenic index, Jameson-Wolf algorithm (Jameson and Wolf (1988) *CABIOS* 4:121–136); surface probability plot, Emini algorithm (Emini et al. (1985) *J Virol* 55:836–839).

Prediction of the Chromosomal Location of Lor-2—Electronic Mapping

To predict the chromosomal location of Lor-2, the Lor-2 nucleotide sequence of SEQ ID NO: 1 was used to query, using the BLASTN program (Altschul S. F. et al, (1990) *J. Mol. Biol.* 215: 403–410) with a word length of 12 and using the BLOSUM62 scoring matrix, a database of human nucleotide sequences originating from nucleotide molecules (e.g., EST sequences, STS sequences and the like) that have been mapped to the human genome. Nucleotide sequences which had been previously mapped to human chromosome 2 near the D2S145 marker (e.g., having Accession Nos. AA191602 and R55706) were found to have high sequence identity to portions of the Lor-2 nucleotide sequence (3' UTR sequence) indicating that Lor-2 maps to the same chromosomal location. Moreover, it is predicted that allelic variants of Lor-2 will map the same chromosomal location and species orthologs of Lor-2 will map to loci syntenic with the human Lor-2 locus.

Confirmation and Analysis of the Chromosomal Location of Lor-2—PCR Mapping

The hLor-2 gene was mapped to human chromosome 2 (i.e., 2p11–p13), which is syntenic to mouse chromosome 6, by PCR typing of the Genebridge (G4) radiation hybrid panel (Research Genetics, Inc., Huntsville, Ala.). Typing of the DNA and comparison to radiation hybrid map data at the Whitehead Institute Center for Genome Research (WICGR) tightly linked the hLor-2 gene to a region on human chromosome 2 between WI-5987 (13.9cR) and GCT1B4 (16.7cR).

The huLor-2 primers used in the PCR mapping studies were: forward—GCTTACCAAGAAACCCATGTCAGC (SEQ ID NO:11) and reverse—GGCAGTTAGTCAGGTGCTGC (SEQ ID NO:12). The radiation hybrid mapping studies were performed as follows: PCR reactions of radiation hybrid panels, GeneBridge 4 (Research Genetics, Inc., Huntsville, Ala.) were assembled in duplicate using an automated PCR assembly program on a TECAN Genesis. Each reaction consisted of: 5 μl DNA template (10 ng/μl), 1.5 μl 10×PCR buffer, 1.2 μl dNTPs (2.5 mM), 1.15 μl forward primer (6.6 μM) 1.15 μl reverse primer (6.6 μM0, and 5 μl:75 platinum Taq. The reactions were thermocycled on a Perkin-Elmer 9600 for 95° C. 10 minutes (for the platinum Taq), [95° C. 40 sec, 52° C. 40 sec, 72° C., 50 sec] 35×, 72° C., 5 minutes, 4° C. hold. Resulting PCR products were run out on a 2% agarose gel and visualized on a UV light box.

The positive hybrids for the Genebridge 4 panel were submitted to the Whitehead Genome Center for placement in relation to a framework map.

Human Lor-2 mapped in close proximity to known genes including actin, gamma 2, smooth muscle, enteric ("ACTG2"), nucleolysin TIA1, semaphorin W ("SEMA W"), dysferlin ("DYSF"), docking protein 1 ("DOK1"), glutamine-fructose-6-phosphate transaminase 1 ("GFPT"), the KIAA0331 gene, deoxyguanosine kinase ("DGUOK"), the TSC501 gene, eukaryotic translation initiation factor 3, subunit 10 ("EIF3S1"), tachykinin receptor 1 ("TACR1"), tissue-type plasminogen activator ("PLAT") and dual specificity phosphatase 11 ("DUSP11"). Nearby disease mutations and/or loci include Alstrom syndrome ("ALMS1"), an autosomal recessively inherited syndrome characterized by retinal degeneration, obesity, diabetes mellitus, neurogenous deafness, hepatic dysfunction, and in some cases, late onset cardiomyopathy (see e.g., Alstrom et al. (1959) *Acta Psychiat. Neurol. Scand.* 34 (suppl. 129):1–35; Alter and Moshang (1993) *Am. J. Dis. Child.* 147:97–99; Awazu et al. (1997) *Am. J. Med. Genet.* 69:13–16; Aynaci et al. (1995) (*Letter*) *Clin. Genet.* 48:164–166; Charles et al. (1990) *J. Med. Genet.* 27:590–592; Cohen and Kisch (1994) *Israel J. Med. Sci.* 30:234–236; Collin et al. (1997) *Hum. Molec. Genet.* 6:213–219; Collin et al. (1999) (*Letter*) *Clin. Genet.* 55:61–62; Connolly et al. (1991) *Am. J. Med. Genet.* 40:421–424; Goldstein and Fialkow (1973) *Medicine* 52:53–71; Macari et al. (1998) *Hum. Genet.* 103:658–661; Marshall et al. (1997) *Am. J. Med. Genet.* 73:150–161; Michaud et al. (1996) *J. Pediat.* 128:225–229; Millay et al. (1986) *Am. J. Ophthal.* 102:482–490; Rudiger et al. (1985) *Hum. Genet.* 69:76–78; Russell-Eggitt et al. (1998) *Ophthalmology* 105:1274–1280; Tremblay et al. (1993) *Am. J. Ophthal.* 115:657–665; Warren et al. (1987) *Am. Heart J.* 114:1522–1524 and Weinstein et al. (1969) *New Eng. J. Med.* 281:969–977), orofacial cleft 2 ("OFC2") (see e.g., Carinci et al. (1995) (*Letter*) *Am. J. Hum. Genet.* 56:337–339; Pezzetti et al. (1998) *Genomics* 50:299–305 and Scapoli et al. (1997) *Genomics* 43:216–220) and Parkinsons disease 3 (see e.g., Di Rocco et al. (1996) *Adv. Neurol.* 69:3–11 and Gasser et al. (1998) *Nature Genet.* 18:262–265). Additional information regarding Alstrom syndrome, orofacial cleft 2 and Parkinson disease 3 can be found collected under Accession Nos. 203800, 602966 and 602404, respectively, in the Online Mendelian Inheritance in Man ("OMIM™") database located at http://www.ncbi.nlm.nih.gov/Omim/, the contents of which are incorporated herein by reference.

Moreover, the syntenic location on mouse chromosome 6 is near ovarian teratoma susceptibility 1 ("Ots-1"), dysruption of corticosterone in adrenal cortex cells ("Cor"), brain protein 1 ("Brp1"), lymphocyte antigen 36 ("Ly36"), major liver protein 1 ("Lvp1"), cerebellar deficient folia ("cdf"), motor neuron degeneration 2 ("mnd2"), truncate ("tc") and faded ("fe"). Of particular interest are the Lor-2 neighbors Ots-1 and Cor, both of which a postulated to play a role in tumor susceptibility. The Ots-1 locus was identified by linkage analysis of female LT/Sv mice, a strain characterized by its abnormally high incidence of spontaneous ovarian teratomas, which are extremely rare for other mouse strains. Ots-1 was identified as the single major locus that increases the frequency of teratomas in a semidominant manner (Lee et al. (1997) *Cancer Res.* 57:590–593. Likewise, the cor locus was identified as being associated with a phenotype of the AJ mouse strain (a strain susceptible to many neoplasms and infectious agents, presumably due to a deficiency in the phophylactic activities of endogenous glucocorticoids (e.g., adrenalcortical corticosterone ("CS")) (Thaete et al. (1990) *Proc. Soc. Exp. Biol. Med.* 194:97–102). Accordingly, at least two loci in the near vicinity of mouse Lor-2 on chromosome 6 are associated with tumor susceptibility. Additional information regarding the Ots-1 and Cor loci can be found collected under Accession Nos. MGI:85864 and MGI:58993, respectively, in the Mouse Genomics Informatics database located at http:/www.informatics.jax.org, the contents of which are incorporated herein by reference. Likewise, information regarding the cdf locus, the mnd2 locus and the mouse Lor-2 gene (i.e., the mouse ortholog of human Lor-2) can be found collected under Accession Nos. MGI:86274, MGI:97039 and MGI: 1337004, respectively.

Figure 6:
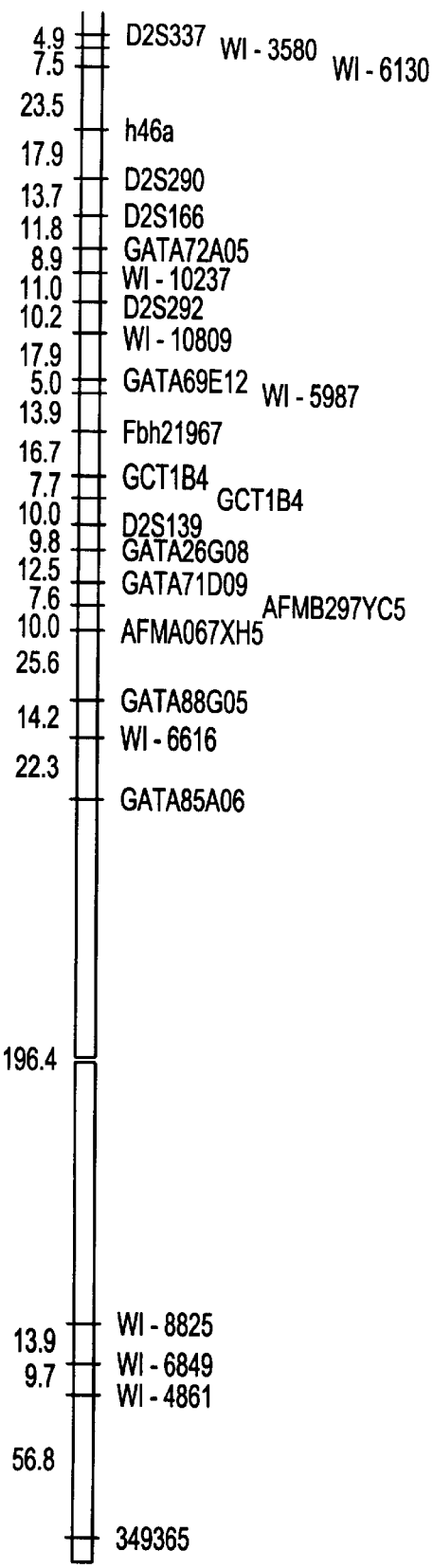
FIG. 6 depicts the results of radiation hybrid mapping of the gene encoding human Lor-2 (i.e., clone Fbh21967). The location of clone Fbh21967, relative to various markers, is depicted as are the relative distances between markers.
Figure 7:
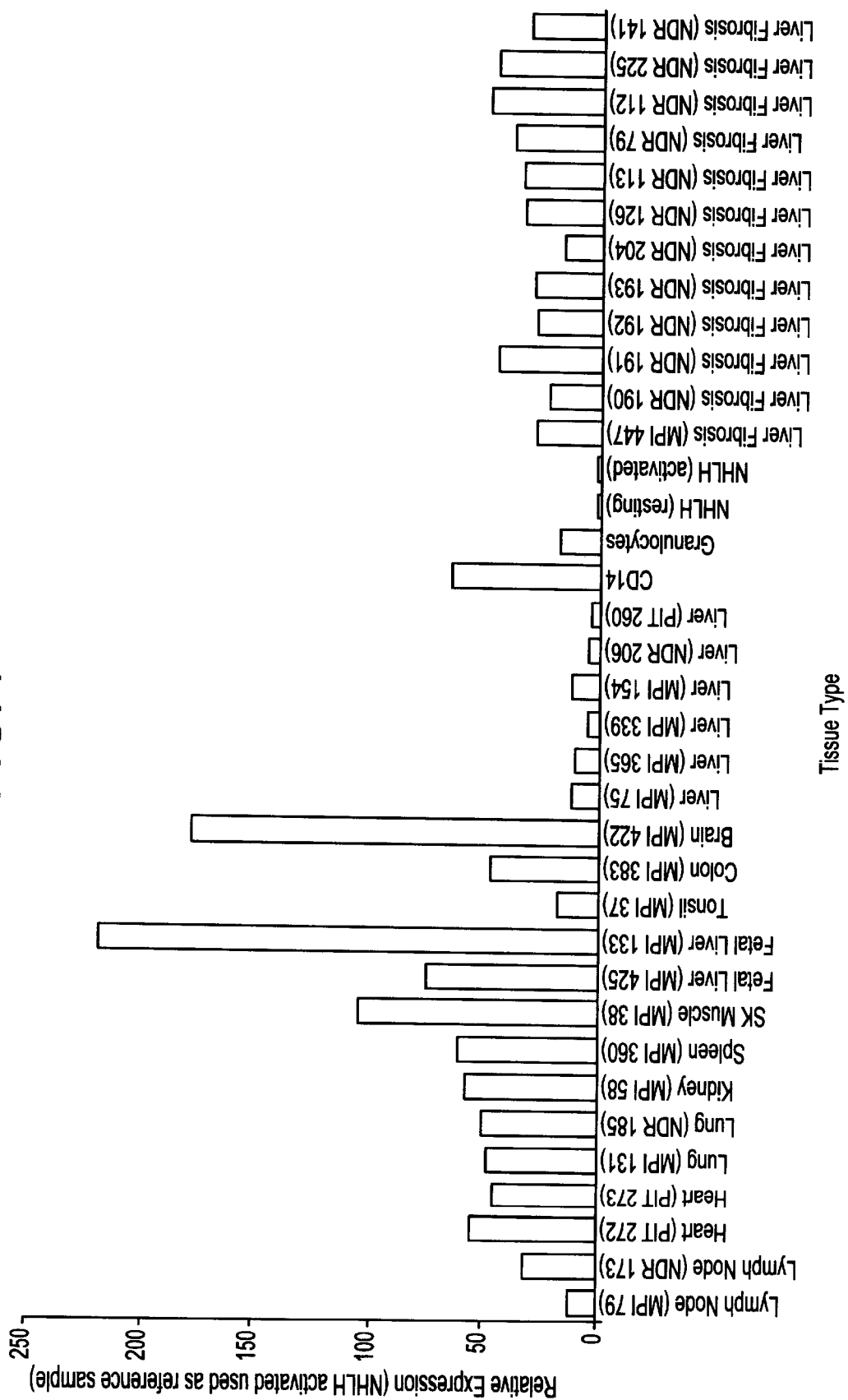
FIG. 7 is a graphic depiction of the relative levels of Lor-2 expression in various normal tissue samples.
Figure 8:
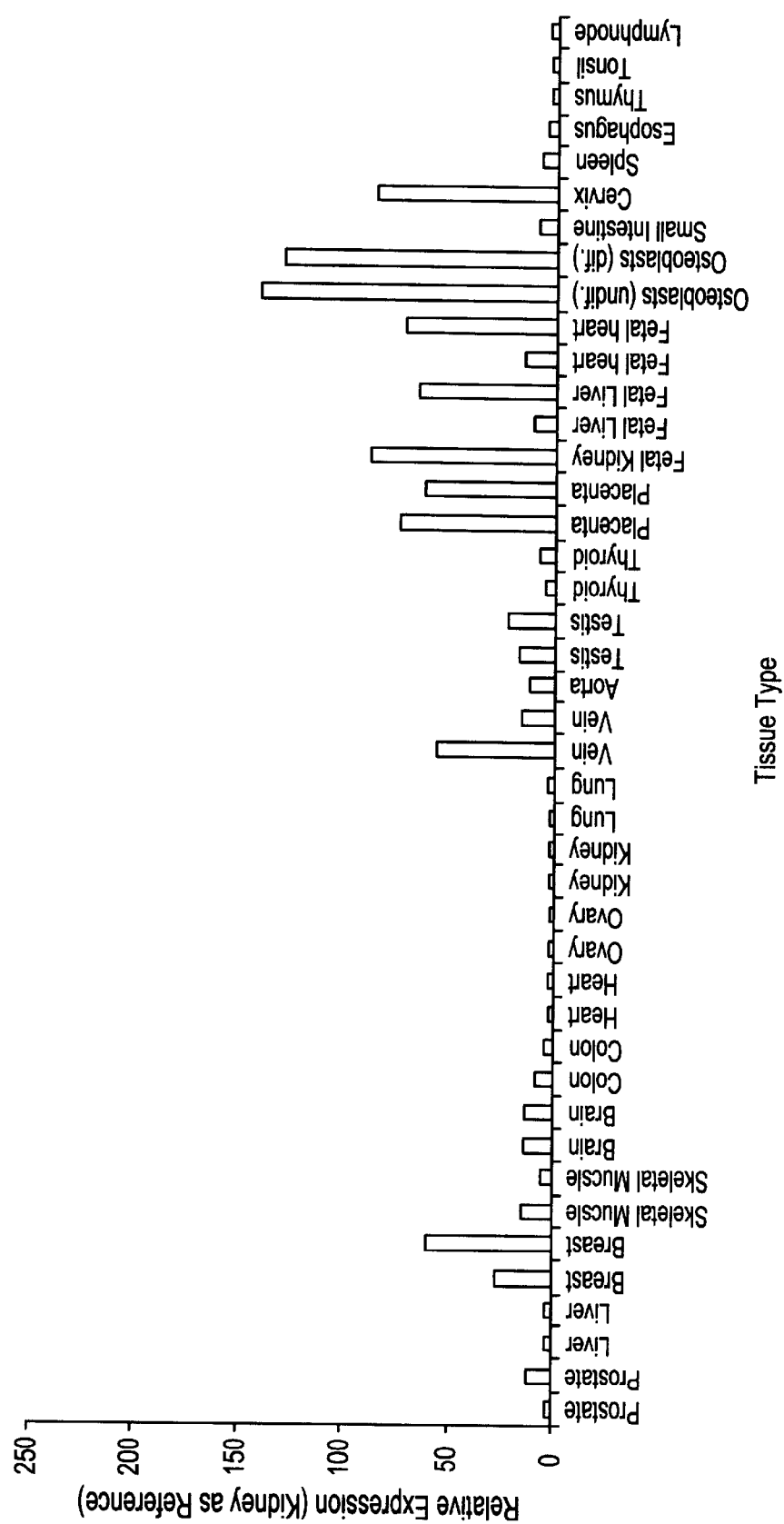
FIG. 8 is a graphic depiction of the relative levels of Lor-2 expression in additional tissue and cell samples.
Figure 9:
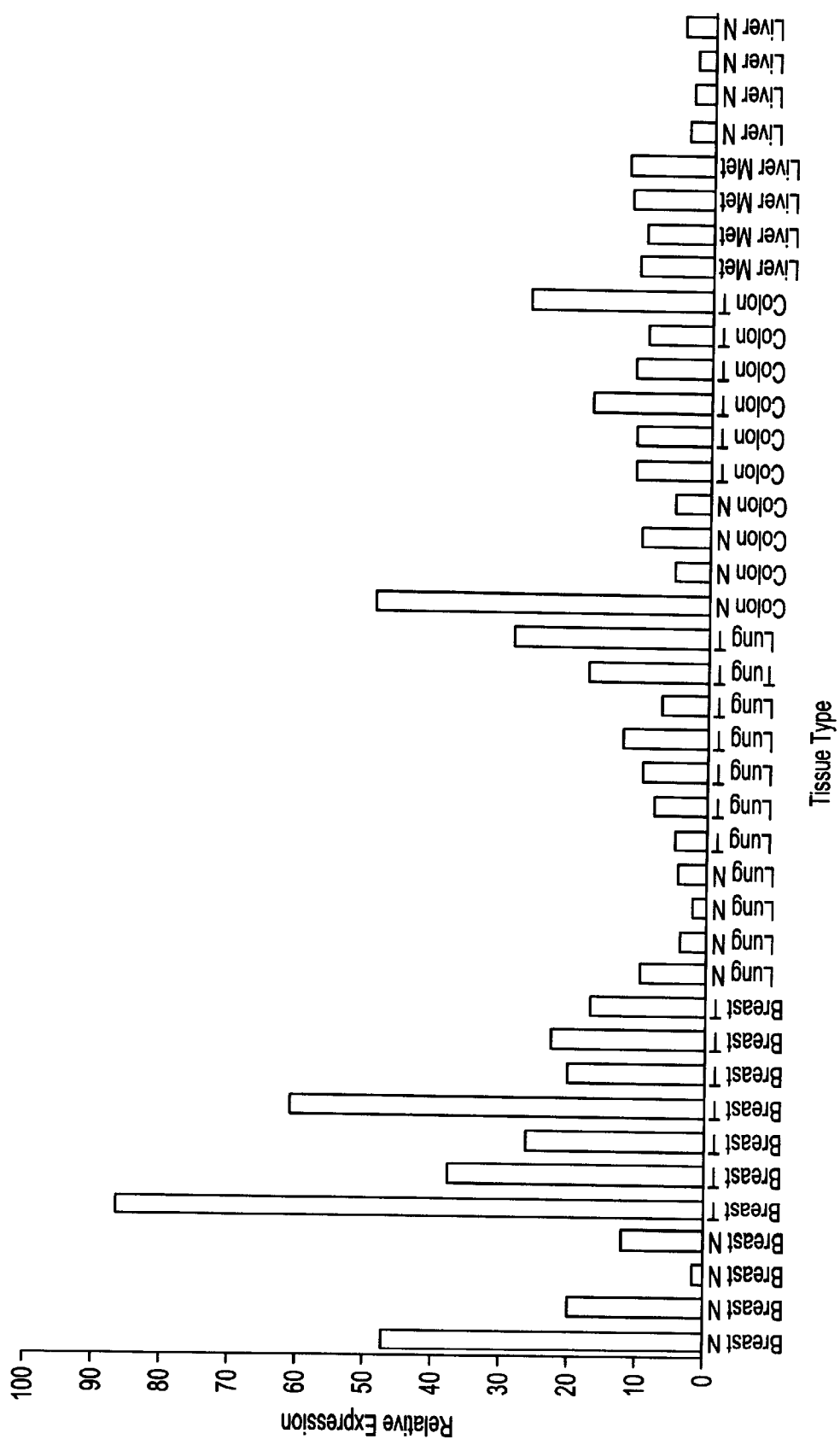
FIG. 9 is a graphic depiction of the relative levels of Lor-2 expression in various normal versus tumor tissue samples.

Additional markers (e.g., EST markers, STS markers and the like) are set forth in FIG. 6, as are the relative distances between markers.

Tissue Distribution of Lor-2 mRNA

Standard molecular biology methods (Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989) were used to construct cDNA libraries in plasmid vectors from multiple human tissues. Individual cDNA clones from each library were isolated and sequenced and their nucleotide sequences were input into a database. The Lor-2 nucleotide sequence of SEQ ID NO:1 was used to query the tissue-specific library cDNA clone nucleotide sequence database using the BLASTN program (Altschul S. F. et al, (1990) *J. Mol. Biol.* 215: 403–410) with a word length of 12 and using the BLOSUM62 scoring matrix. Nucleotide sequences identical to portions of the Lor-2 nucleotide sequence of SEQ ID NO:1 were found in cDNA libraries originating from human endothelial cells, lymph node, bone, heart, neuron, and testes. Lor-2 nucleic acid sequences, fragments thereof, proteins encoded by these sequences, and fragments thereof as well as modulators of Lor-2 gene or protein activity may be useful for diagnosing or treating diseases that involve the tissues in which the Lor-2 mRNA is expressed. Likewise, when a similar analysis was performed using the Lor-2 sequence of SEQ ID NO:1 to query publicly available nucleotide sequence databases (e.g., DBEST databases) using BLAST, sequences having high homology to the 3' untranslated region of human Lor-2 were identified in a Soares placenta normalized library and in Soares testis, B-cell and lung normalized libraries.

Northern blot hybridization with RNA samples was next performed under standard conditions and washed under stringent conditions, i.e., 0.2×SSC at 65° C. A DNA probe was radioactively labeled with $^{32}$P-dCTP using the Prime-It kit (Stratagene, La Jolla, Calif.) according to the instructions of the supplier. Filters containing various tissue and cell line mRNAs were probed in ExpressHyb hybridization solution (Clontech) and washed at high stringency according to manufacturer's recommendations.

On a human mRNA blot containing mRNA from heart, brain, placenta, lung, liver, skeletal muscle, kidney, and pancreas, Lor-2 transcript (~3.0 kb) was detected in all tissues tested but was most strongly detected in heart and placenta. Moreover, Lor-2 mRNA was strongly expressed in the G361 melanoma cell line and in the SW480 adenocarcinoma colon cell lines (as compared to expression in the HL60, HeLa53, K562, Molty, Raji, and SW480 cell lines (SW480 cell line expressing a 2.4 kb transcript). Transcripts of 5 kb and 2 kb were also detected evidencing possible splice variants of Lor-2.

Testing of a larger panel of human tissues revealed the following expression levels. Expression levels were normalized to beta 2 expression.

TABLE I hu Lor-2 Expression in Normal Tissues

| Tissue Source | huLor-2 Expression | Beta 2 Expression | Relative Expression* |
|---|---|---|---|
| Lymph Node (MPI 79) | 30.550 | 18.170 | 10.78 |
| Lymph Node (NDR 173) | 29.930 | 19.190 | 33.59 |
| Heart (PIT 272) | 26.145 | 18.170 | 57.06 |
| Heart (PIT 273) | 29.375 | 19.110 | 46.85 |
| Lung (MPI 131) | 29.650 | 19.480 | 50.04 |
| Lung (NDR 185) | 27.165 | 17.050 | 51.96 |
| Kidney (MPI 58) | 30.695 | 20.790 | 60.13 |
| Spleen (MPI 360) | 27.005 | 17.150 | 62.25 |
| SK Muscle (MPI 38) | 29.480 | 20.400 | 106.15 |
| Fetal Liver (MPI 425) | 30.065 | 20.520 | 75.85 |
| Fetal Liver (MPI 133) | 31.570 | 23.550 | 221.32 |
| Tonsil (MPI 37) | 29.480 | 17.890 | 18.64 |
| Colon (MPI 383) | 30.045 | 19.830 | 48.50 |
| Brain (MPI 422) | 30.525 | 22.220 | 181.65 |
| Liver (MPI 75) | 32.935 | 20.940 | 14.07 |
| Liver (MPI 365) | 31.060 | 18.770 | 11.35 |
| Liver (MPI 339) | 33.985 | 20.740 | 5.92 |
| Liver (MPI 154) | 32.000 | 19.970 | 13.74 |
| Liver (NDR 206) | 33.750 | 20.370 | 5.41 |
| Liver (PIT 260) | 32.705 | 18.970 | 4.23 |
| CD14 | 26.945 | 17.190 | 66.49 |
| Granulocytes | 30.825 | 19.240 | 18.77 |
| NHLH (resting) | 36.595 | 19.920 | 1.10 |
| NHLH (activated) | 35.570 | 19.760 | 1.00 |
| Liver Fibrosis (MPI 447) | 29.320 | 18.300 | 27.67 |
| Liver Fibrosis (NDR 190) | 36.495 | 24.180 | 22.55 |
| Liver Fibrosis (NDR 191) | 30.105 | 19.770 | 44.63 |
| Liver Fibrosis (NDR 192) | 33.415 | 22.410 | 27.95 |
| Liver Fibrosis (NDR 193) | 30.795 | 19.830 | 28.74 |
| Liver Fibrosis (NDR 204) | 33.360 | 21.580 | 16.34 |
| Liver Fibrosis (NDR 126) | 31.900 | 21.180 | 34.18 |
| Liver Fibrosis (NDR 113) | 29.175 | 18.510 | 36.51 |
| Liver Fibrosis (NDR 79) | 3C.870 | 20.390 | 40.22 |
| Liver Fibrosis (NDR 112) | 31.955 | 21.770 | 49.52 |
| Liver Fibrosis (NDR 225) | 30.645 | 20.350 | 45.89 |
| Liver Fibrosis (NDR 141) | 33.045 | 22.250 | 32.45 |

*NHLH activated used as reference sample

Next, Lor-2 expression levels were measured in a variety of tissue and cell samples using the Taqman™ procedure. The Taqman™ procedure is a quantitative, real-time PCR-based approach to detecting mRNA. The RT-PCR reaction exploits the 5' nuclease activity of AmplTaq Gold™ DNA Polymerase to cleave a TaqMan™ probe during PCR. Briefly, cDNA is generated from the samples of interest and serves as the starting materials for PCR amplification. In addition to the 5' and 3' gene-specific primers, a gene-specific oligonucleotide probe (complementary to the region being amplified) is included in the reaction (i.e., the Taqman™ probe). The TaqMan™ probe incldes the oligonucleotide with a fluorescent reporter dye covalently linked to the 5' end of the probe (such as FAM (6-carboxyfluorescein), TET (6-carboxy-4,7,2',7'-tetrachlorofluorescein), JOE (6-carboxy-4,5-dichloro-2,7-dimethoxyfluorescein), or VIC) and a quencher dye (TAMRA (6-carboxy-N,N,N',N'-tetramethylrhodamine) at the 3' end of the probe.

During the PCR reaction, cleavage of the probe separates the reporter dye and the quencher dye, resulting in increased fluorescence of the reporter. Accumulation of PCR products is detected directly by monitoring the increase in fluorescence of the reporter dye. When the probe is intact, the proximity of the reporter dye to the quencher dye results in suppression of the reporter fluorescence. During PCR, if the target of interest is present, the probe specifically anneals between the forward and reverse primer sites. The 5'-3' nucleolytic activity of the AmpliTaq™ Gold DNA Polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in every cycle and does not interfere with the exponential accumulation of product.

TABLE II hu Lor-2 3' UTR Expression in Normal Human Tissues

| Tissue Source | Relative Expression* |
|---|---|
| Prostate | 2.5 |
| Prostate | 10.9 |
| Liver | 2.4 |
| Liver | 2.5 |
| Breast | 26.7 |
| Breast | 59.3 |
| Skeletal Muscle | 13.4 |
| Skeletal Muscle | 5.5 |
| Brain | 12.6 |
| Brain | 12.7 |
| Colon | 7.2 |
| Colon | 3.4 |
| Heart | 1.8 |
| Heart | 1.8 |
| Ovary | 1.8 |
| Ovary | 1.4 |
| Kidney | 1.0 |
| Kidney | 2.3 |
| Lung | 1.8 |
| Lung | 4.2 |
| Vein | 57.5 |
| Vein | 16.1 |
| Aorta | 11.8 |
| Testis | 16.4 |
| Testis | 21.7 |
| Thyroid | 4.4 |
| Thyroid | 7.2 |
| Placenta | 73.3 |
| Placenta | 61.8 |
| Fetal Kidney | 87.7 |
| Fetal Liver | 10.0 |
| Fetal Liver | 64.7 |
| Fetal Heart | 14.4 |
| Fetal Heart | 70.8 |
| Osteoblasts (undif.) | 207.9 |
| Osteoblasts | 128.0 (dif.) |
| Small Intestine | 7.9 |
| Cervix | 86.5 |
| Spleen | 6.3 |
| Esophagus | 2.4 |
| Thymus | 1.4 |
| Tonsil | 1.7 |
| Lymphnode | 3.1 |

*Kidney used as reference sample

The highest expression was observed in osteoblasts, cervix, kidney and placenta on the normal human tissue panel tested.

EXAMPLE 2

Expression of Lor-2 mRNA in Clinical Tumor Samples and in Xenograft Cell Lines

In this example, RT-PCR was used to detect the presence of Lor-2 mRNA in various tumor and metastatic tissue samples as compared to normal tissue samples. RT-PCR was also used to detect the presence of Lor-2 mRNA in various xenograft cell lines. In breast tissue, Lor-2 mRNA was detected in 0/1 normal tissue samples as compared to 3/4 tumor clinical samples after 30 cycles of PCR. In xenograft cell lines isolated from breast tissue, Lor-2 mRNA was detected in 1/1 normal and 3/3 xenograft cell lines (cell lines MCF7, ZR75 and T47D). In lung tissue, Lor-2 mRNA was detected in 0/2 normal tissue samples as compared to 2/8 tumor tissue samples. In xenograft cell lines isolated from lung tissue, Lor-2 mRNA was detected in 0/5 xenograft cell lines after 30 cycles of PCR. In a second experiment performed with lung tissue, Lor-2 mRNA was detected in 2/2 normal and 8/8 tumor tissue samples, as well as in 5/5 xenograft cell lines (cell lines A549, H69, H125, H322 and H460) after 35 cycles of PCR. In colon tissue, Lor-2 mRNA was detected in 2/2 normal, 5/5 tumor and 5/5 metastatic samples, as well as in 7/7 xenograft cell lines (cell lines HCT116, HCT15, HT29, SW620, SW480, DLD1 and KM12) after 35 cycles of PCR. In liver tissue, LOR-2 mRNA was detected in 2/2 normal samples after 35 cycles of PCR. These data reveal that there exists a correlation between tumors and Lor-2 expression, at least in breast and lung tissues.

To further investigate this finding, Lor-2 mRNA levels were measured by quantitative PCR using the Taqman™ procedure as described above. The procedure was carried out on cDNA generated from various carcinoma samples and compared to normal counterpart tissue samples. In 5/7 breast carcinomas, a 2–86 fold upregulation of Lor-2 was observed as compared to 2/4 normal breast tissue samples. Likewise, in 4/7 lung carcinomas, a 2–17 fold upregulation was observed as compared to 3/4 normal lung tissue samples. The relative levels of Lor-2 mRNA detected in various normal, tumor and metastases samples are set forth in Table III.

Table III hu Lor-2 Expression -
Taqman Analysis of Oncology Panel

| Tissue Source | Relative Expression |
|---|---|
| Breast N | 46.85 |
| Breast N | 18.96 |
| Breast N | 1.00 |
| Breast N | 11.75 |
| Breast T | 86.52 |
| Breast T | 37.27 |
| Breast T | 25.72 |
| Breast T | 60.76 |
| Breast T | 19.84 |
| Breast T | 22.24 |
| Breast T | 16.26 |
| Lung N | 9.32 |
| Lung N | 3.34 |
| Lung N | 1.65 |
| Lung N | 3.84 |
| Lung T | 4.26 |
| Lung T | 7.39 |
| Lung T | 9.13 |
| Lung T | 12.08 |
| Lung T | 6.48 |
| Lung T | 17.27 |
| Lung T | 28.15 |
| Colon N | 48.50 |
| Colon N | 4.94 |
| Colon N | 10.09 |
| Colon N | 4.94 |
| Colon T | 10.78 |
| Colon T | 10.89 |
| Colon T | 17.39 |
| Colon T | 10.82 |
| Colon T | 9.09 |
| Colon T | 26.63 |
| Liver Met | 10.93 |
| Liver Met | 10.30 |
| Liver Met | 12.25 |
| Liver Met | 12.91 |
| Liver N | 4.30 |
| Liver N | 3.69 |
| Liver N | 3.48 |
| Liver N | 5.41 |

These data reveal a significant upregulation of Lor-2 mRNA in at least breast and lung carcinomas. Moreover, there was a significant upregulation of Lor-2 expression in metastatic as compared to normal liver samples. Given that the mRNA for Lor-2 is expressed in a variety of tumors, with significant upregulation in carcinoma samples in comparison to normal samples, it is believed that inhibition of Lor-2 activity may inhibit tumor progression by affecting the adhesive properties of the tumor cells to surrounding tissues.

EXAMPLE 3

Expression of Recombinant Lor-2 Protein in Bacterial Cells

In this example, Lor-2 is expressed as a recombinant glutathione-S-transferase (GST) fusion polypeptide in *E. coli* and the fusion polypeptide is isolated and characterized. Specifically, Lor-2 is fused to GST and this fusion polypeptide is expressed in *E. coli*, e.g., strain PEB199. Expression of the GST-Lor-2 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

EXAMPLE 4

Expression of Recombinant Lor-2 Protein in COS Cells

To express the Lor-2 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire Lor-2 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the Lor-2 DNA sequence is amplified by PCR using two primers. The 5' primer contains the restriction site of interest followed by approximately twenty nucleotides of the Lor-2 coding sequence starting from the initiation codon; the 3' end sequence contains complementary sequences to the other restriction site of interest, a translation stop codon, the HA tag or FLAG tag and the last 20 nucleotides of the Lor-2 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the Lor-2 gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the Lor-2-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning. A Laboratory Manual. 2nd, ed., Cold Spring Harbor Laboratory,* Cold Spring Harbor Laboratory Press, Cold Spring Harbor, N.Y., 1989. The expression of the Lor-2 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual,* Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the Lor-2 coding sequence is cloned directly into the polylinker of the pCDNA/Amp vector using the appropriate restriction sites. The resulting plasmid is transfected into COS cells in the manner described above, and the expression of the Lor-2 polypeptide is detected by radiolabelling and immunoprecipitation using a Lor-2 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for identifying a compound which binds to a Lor-2 polypeptide, comprising:
   a) contacting the polypeptide, or a cell expressing the polypeptide with a test compound; and
   b) determining whether the polypeptide binds to the test compound, wherein said Lor-2 polypeptide is at least 93% identical to a polypeptide comprising the amino acid sequence of SEQ ID NO:2 and has a Lor-2 activity selected from the group consisting of an aminotransferase activity, peptidyl lysine oxidation, oxidative deamination of lysine, and copper binding.

2. The method of claim 1, wherein the binding of the test compound to the Lor-2 polypeptide is detected by a method selected from the group consisting of:
   a) detection of binding by direct detection of test compound/polypeptide binding;
   b) detection of binding using a competition binding assay; and
   c) detection of binding using an assay for the Lor-2 activity.

3. A method for identifying a compound which modulates the activity of a Lor-2 polypeptide comprising:
   a) contacting a Lor-2 polypeptide with a test compound; and
   b) determining the effect of the test compound on the activity of the polypeptide to thereby identify a compound which modulates the activity of the polypeptide, wherein said Lor-2 polypeptide is at least 93% identical to a polypeptide comprising the amino acid sequence of SEQ ID NO:2 and has a Lor-2 activity selected from the group consisting of an aminotransferase activity, peptidyl lysine oxidation, oxidative deamination of lysine, and copper binding.

4. A method of identifying a compound which modulates tumor progression comprising:
   a) contacting a Lor-2 polypeptide with a test compound; and
   b) determining the effect of the test compound on the activity of the polypeptide to thereby identify a compound which modulates The activity of the polypeptide, such that the compound which modulates tumor progression is identified, wherein said Lor-2 polypeptide is at least 93% identical to a polypeptide comprising the amino acid sequence of SEQ ID NO:2 and has a Lor-2 activity selected from the group consisting of an aminotransferase activity, peptidyl lysine oxidation, oxidative deamination of lysine, and copper binding.

5. A method of identifying a compound which modulates metastasis comprising:

a) contacting a Lor-2 polypeptide with a test compound; and b) determining the effect of the test compound on the activity of the polypeptide to thereby identify a compound which modulates the activity of the polypeptide, such that The compound which modulates metastasis is identified, wherein said Lor-2 polypeptide is at least 93% identical to a polypeptide comprising the amino acid sequence of SEQ ID NO:2 and has a Lor-2 activity selected from the group consisting of an aminotransferase activity, peptidyl lysine oxidation, oxidative deamination of lysine, and copper binding.

6. The method of any one of claims 3, 4, 5 which involves identification of an inhibitory compound.

7. The method of any one of claims 1–2, 3 or 4–5, wherein the Lor-2 polypeptide is at least 95% identical to a polypeptide comprising the amino acid of SEQ ID NO:2.

8. The method of any one of claims 1–2, 3 or 4–5 wherein the Lor-2 polypeptide is at least 97% identical to a polypeptide comprising the amino acid sequence of SEQ ID NO:2.

9. The method of any one of claims 1–2, 3 or 4–5 wherein the Lor-2 polypeptide comprises the amino acid sequence of SEQ ID NO:2.

10. A method for identifying a compound which binds to a Lor-2 polypeptide, comprising:

a) contacting the polypeptide, or a cell expressing the polypeptide with a test compound; and b) determining whether the polypeptide binds to the test compound, wherein said Lor-2 polypeptide is encoded by a nucleotide sequence which is at least 98% identical to a nucleic acid comprising the nucleotide sequence of SEQ ID NO:1 and has a Lor-2 activity selected from the group consisting of an aminotransferase activity, peptidyl lysine oxidation, oxidative deamination of lysine, and copper binding.

11. The method of claim 10, wherein the binding of the test compound to the Lor-2 polypeptide is detected by a method selected from the group consisting of:

a) detection of binding by direct detection of test compound/polypeptide binding;

b) detection of binding using a competition binding assay; and c) detection of binding using an assay for the Lor-2 activity.

12. A method for identifying a compound which modulates the activity of a Lor-2 polypeptide comprising:

a) contacting a Lor-2 polypeptide with a test compound; and b) determining the effect of the test compound on the activity of the polypeptide to thereby identify a compound which modulates the activity of the polypeptide, wherein said Lor-2 polypeptide is encoded by a nucleotide sequence which is at least 98% identical to a nucleic acid comprising the nucleotide sequence of SEQ ID NO:1 and has a Lor-2 activity selected from the group consisting of an aminotransferase activity, peptidyl lysine oxidation, oxidative deamination of lysine, and copper binding.

13. A method of identifying a compound which modulates tumor progression comprising:

a) contacting a Lor-2 polypeptide with a test compound; and b) determining the effect of the test compound on the activity of the polypeptide to thereby identify a compound which modulates the activity of the polypeptide, such that the compound which modulates tumor progression is identified, wherein said Lor-2 polypeptide is encoded by a nucleotide sequence which is at least 98% identical to a nucleic acid comprising the nucleotide sequence of SEQ ID NO:1 and has a Lor-2 activity selected from the group consisting of an aminotransferase activity, peptidyl lysine oxidation, oxidative deamination of lysine, and copper binding.

14. A method of identifying a compound which modulates metastasis comprising:

a) contacting a Lor-2 polypeptide with a test compound; and b) determining the effect of the test compound on the activity of the polypeptide to thereby identify a compound which modulates the activity of the polypeptide, such that the compound which modulates metastasis is identified, wherein said Lor-2 polypeptide is encoded by a nucleotide sequence which is at least 98% identical to a nucleic acid comprising the nucleotide sequence of SEQ ID NO:1 and has a Lor-2 activity selected from the group consisting of an aminotransferase activity, peptidyl lysine oxidation, oxidative deamination of lysine, and copper binding.

15. The method of any one of claims 12, 13 or 14 which involves identification of an inhibitory compound.

16. The method of any one of claims 10–14 wherein the Lor-2 polypeptide is encoded by a nucleotide sequence which is at least 99% identical to a nucleic acid comprising the nucleotide sequence of SEQ ID NO:1.

17. The method of any one of claims 10–14 wherein the Lor-2 polypeptide is encoded by a nucleic acid comprising the nucleotide sequence of SEQ ID NO:1.

* * * * *

UNITED STATES PATENT AND TRADEMARK OFFICE
CERTIFICATE OF CORRECTION

PATENT NO. : 6,300,092 B1
DATED : October 9, 2001
INVENTOR(S) : Mehran M. Khodadoust and Kyle J. MacBeth Page 1 of 1

It is certified that error appears in the above-identified patent and that said Letters Patent is hereby corrected as shown below:

<u>Column 2,</u>
Line 66, please remove the capitalized "<u>T</u>" (alphabet) within the word "<u>T</u>he" and replace it with a lower case "<u>t</u>" (alphabet) to read as:
-- compound which modulates the activity of the peptide,... --

<u>Column 1,</u>
Line 16, please remove the capitalized "<u>T</u>" (alphabet) within the word "<u>T</u>he" and replace it with a lower case "<u>t</u>" (alphabet) to read as:
-- such that the compound which modulates metatasis is identified,... --

Signed and Sealed this

Twenty-first Day of May, 2002

Attest:

Attesting Officer

JAMES E. ROGAN
*Director of the United States Patent and Trademark Office*

SEQUENCE LISTING

<160> NUMBER OF SEQ ID NOS: 12

<210> SEQ ID NO 1
<211> LENGTH: 2920
<212> TYPE: DNA
<213> ORGANISM: Homo sapiens
<220> FEATURE:
<221> NAME/KEY: CDS
<222> LOCATION: (143)..(2401)

<400> SEQUENCE: 1

```
cgtccgccac gcgtccggac tagttctaga tcgcgagcgg ccgcccttt tttttttt          60 ttggaagtcc taggactgat ctccaggacc agcactcttc tcccagccct tagggtcctg      120
ctcggccaag gccttccctg cc atg cga cct gtc agt gtc tgg cag tgg agc       172
                         Met Arg Pro Val Ser Val Trp Gln Trp Ser
                          1               5                  10 ccc tgg ggg ctg ctg ctg tgc ctg ctg tgc agt tcg tgc ttg ggg tct        220
Pro Trp Gly Leu Leu Leu Cys Leu Leu Cys Ser Ser Cys Leu Gly Ser
                15                  20                  25 ccg tcc cct tcc acg ggc cct gag aag aag gcc ggg agc cag ggg ctt        268
Pro Ser Pro Ser Thr Gly Pro Glu Lys Lys Ala Gly Ser Gln Gly Leu
            30                  35                  40 cgg ttc cgg ctg gct ggc ttc ccc agg aag ccc tac gag ggc cgc gtg        316
Arg Phe Arg Leu Ala Gly Phe Pro Arg Lys Pro Tyr Glu Gly Arg Val
        45                  50                  55 gag ata cag cga gct ggt gaa tgg ggc acc atc tgc gat gat gac ttc        364
Glu Ile Gln Arg Ala Gly Glu Trp Gly Thr Ile Cys Asp Asp Asp Phe
    60                  65                  70 acg ctg cag gct gcc cac atc ctc tgc cgg gag ctg ggc ttc aca gag        412
Thr Leu Gln Ala Ala His Ile Leu Cys Arg Glu Leu Gly Phe Thr Glu
75                  80                  85                  90 gcc aca ggc tgg acc cac agt gcc aaa tat ggc cct gga aca ggc cgc        460
Ala Thr Gly Trp Thr His Ser Ala Lys Tyr Gly Pro Gly Thr Gly Arg
                95                 100                 105 atc tgg ctg gac aac ttg agc tgc agt ggg acc gag cag agt gtg act        508
Ile Trp Leu Asp Asn Leu Ser Cys Ser Gly Thr Glu Gln Ser Val Thr
            110                 115                 120
```

```
gaa tgt gcc tcc cgg ggc tgg ggg aac agt gac tgt acg cac gat gag       556
Glu Cys Ala Ser Arg Gly Trp Gly Asn Ser Asp Cys Thr His Asp Glu
        125                 130                 135 gat gct ggg gtc atc tgc aaa gac cag cgc ctc cct ggc ttc tcg gac       604
Asp Ala Gly Val Ile Cys Lys Asp Gln Arg Leu Pro Gly Phe Ser Asp
    140                 145                 150 tcc aat gtc att gag gta gag cat cac ctg caa gtg gag gag gtg cga       652
Ser Asn Val Ile Glu Val Glu His His Leu Gln Val Glu Glu Val Arg
155                 160                 165                 170 att cga ccc gcc gtt ggg tgg ggc aga cga ccc ctg ccc gtg acg gag       700
Ile Arg Pro Ala Val Gly Trp Gly Arg Arg Pro Leu Pro Val Thr Glu
                175                 180                 185 ggg ctg gtg gaa gtc agg ctt cct gac ggc tgg tcg caa gtg tgc gac       748
Gly Leu Val Glu Val Arg Leu Pro Asp Gly Trp Ser Gln Val Cys Asp
            190                 195                 200 aaa ggc tgg agc gcc cac aac agc cac gtg gtc tgc ggg atg ctg ggc       796
Lys Gly Trp Ser Ala His Asn Ser His Val Val Cys Gly Met Leu Gly
            205                 210                 215 ttc ccc agc gaa aag agg gtc aac gcg gcc ttc tac agg ctg cta gcc       844
Phe Pro Ser Glu Lys Arg Val Asn Ala Ala Phe Tyr Arg Leu Leu Ala
        220                 225                 230 caa cgg cag caa cac tcc ttt ggt ctg cat ggg gtg gcg tgc gtg ggc       892
Gln Arg Gln Gln His Ser Phe Gly Leu His Gly Val Ala Cys Val Gly
235                 240                 245                 250 acg gag gcc cac ctc tcc ctc tgt tcc ctg gag ttc tat cgt gcc aat       940
Thr Glu Ala His Leu Ser Leu Cys Ser Leu Glu Phe Tyr Arg Ala Asn
                255                 260                 265 gac acc gcc agg tgc cct ggg ggg ggc cct gca gtg gtg agc tgt gtg       988
Asp Thr Ala Arg Cys Pro Gly Gly Gly Pro Ala Val Val Ser Cys Val
            270                 275                 280 cca ggc cct gtc tac gcg gca tcc agt ggc cag aag aag caa caa cag      1036
Pro Gly Pro Val Tyr Ala Ala Ser Ser Gly Gln Lys Lys Gln Gln Gln
        285                 290                 295 tcg aag cct cag ggg gag gcc cgt gtc cgt cta aag ggc ggc gcc cac      1084
Ser Lys Pro Gln Gly Glu Ala Arg Val Arg Leu Lys Gly Gly Ala His
300                 305                 310 cct gga gag ggc cgg gta gaa gtc ctg aag gcc agc aca tgg ggc aca      1132
Pro Gly Glu Gly Arg Val Glu Val Leu Lys Ala Ser Thr Trp Gly Thr
315                 320                 325                 330 gtc tgt gac cgc aag tgg gac ctg cat gca gcc agc gtg gtg tgt cgg      1180
Val Cys Asp Arg Lys Trp Asp Leu His Ala Ala Ser Val Val Cys Arg
                335                 340                 345 gag ctg ggc ttc ggg agt gct cga gaa gct ctg agt ggc gct cgc atg      1228
Glu Leu Gly Phe Gly Ser Ala Arg Glu Ala Leu Ser Gly Ala Arg Met
            350                 355                 360 ggg cag ggc atg ggt gct atc cac ctg agt gaa gtt cgc tgc tct gga      1276
Gly Gln Gly Met Gly Ala Ile His Leu Ser Glu Val Arg Cys Ser Gly
        365                 370                 375 cag gag ctc tcc ctc tgg aag tgc ccc cac aag aac atc aca gct gag      1324
Gln Glu Leu Ser Leu Trp Lys Cys Pro His Lys Asn Ile Thr Ala Glu
        380                 385                 390 gat tgt tca cat agc cag gat gcc ggg gtc cgg tgc aac cta cct tac      1372
Asp Cys Ser His Ser Gln Asp Ala Gly Val Arg Cys Asn Leu Pro Tyr
395                 400                 405                 410 act ggg gca gag acc agg atc cga ctc agt ggg ggc cgc agc caa cat      1420
Thr Gly Ala Glu Thr Arg Ile Arg Leu Ser Gly Gly Arg Ser Gln His
                415                 420                 425 gag ggg cga gtc gag gtg caa ata ggg gga cct ggg ccc ctt cgc tgg      1468
Glu Gly Arg Val Glu Val Gln Ile Gly Gly Pro Gly Pro Leu Arg Trp
```

-continued

|  |  |  |  |  |  |  |  |  |  |  |  |  |  |  |  |  |
|---|---|---|---|---|---|---|---|---|---|---|---|---|---|---|---|---|
|  |  |  | 430 |  |  |  | 435 |  |  |  | 440 |  |  |  |  |  |
| ggc | ctc | atc | tgt | ggg | gat | gac | tgg | ggg | acc | ctg | gag | gcc | atg | gtg | gcc | 1516 |
| Gly | Leu | Ile | Cys | Gly | Asp | Asp | Trp | Gly | Thr | Leu | Glu | Ala | Met | Val | Ala |  |
|  |  |  | 445 |  |  |  | 450 |  |  |  | 455 |  |  |  |  |  |
| tgt | agg | caa | ctg | ggt | ctg | ggc | tac | gcc | aac | cac | ggc | ctg | cag | gag | acc | 1564 |
| Cys | Arg | Gln | Leu | Gly | Leu | Gly | Tyr | Ala | Asn | His | Gly | Leu | Gln | Glu | Thr |  |
|  | 460 |  |  |  |  | 465 |  |  |  |  | 470 |  |  |  |  |  |
| tgg | tac | tgg | gac | tct | ggg | aat | ata | aca | gag | gtg | gtg | atg | agt | gga | gtg | 1612 |
| Trp | Tyr | Trp | Asp | Ser | Gly | Asn | Ile | Thr | Glu | Val | Val | Met | Ser | Gly | Val |  |
| 475 |  |  |  |  | 480 |  |  |  |  | 485 |  |  |  |  | 490 |  |
| cgc | tgc | aca | ggg | act | gag | ctg | tcc | ctg | gat | cag | tgt | gcc | cat | cat | ggc | 1660 |
| Arg | Cys | Thr | Gly | Thr | Glu | Leu | Ser | Leu | Asp | Gln | Cys | Ala | His | His | Gly |  |
|  |  |  |  | 495 |  |  |  |  | 500 |  |  |  |  | 505 |  |  |
| acc | cac | atc | acc | tgc | aag | agg | aca | ggg | acc | cgc | ttc | act | gct | gga | gtc | 1708 |
| Thr | His | Ile | Thr | Cys | Lys | Arg | Thr | Gly | Thr | Arg | Phe | Thr | Ala | Gly | Val |  |
|  |  |  | 510 |  |  |  | 515 |  |  |  | 520 |  |  |  |  |  |
| atc | tgt | tct | gag | act | gca | tca | gat | ctg | ttg | ctg | cac | tca | gca | ctg | gtg | 1756 |
| Ile | Cys | Ser | Glu | Thr | Ala | Ser | Asp | Leu | Leu | Leu | His | Ser | Ala | Leu | Val |  |
|  |  | 525 |  |  |  |  | 530 |  |  |  |  | 535 |  |  |  |  |
| cag | gag | acc | gcc | tac | atc | gaa | gac | cgg | ccc | ctg | cat | atg | ttg | tac | tgt | 1804 |
| Gln | Glu | Thr | Ala | Tyr | Ile | Glu | Asp | Arg | Pro | Leu | His | Met | Leu | Tyr | Cys |  |
|  | 540 |  |  |  |  | 545 |  |  |  |  | 550 |  |  |  |  |  |
| gct | gcg | gaa | gag | aac | tgc | ctg | gcc | agc | tca | gcc | cgc | tca | gcc | aac | tgg | 1852 |
| Ala | Ala | Glu | Glu | Asn | Cys | Leu | Ala | Ser | Ser | Ala | Arg | Ser | Ala | Asn | Trp |  |
| 555 |  |  |  |  | 560 |  |  |  |  | 565 |  |  |  |  | 570 |  |
| ccc | tat | ggt | cac | cgg | cgt | ctg | ctc | cga | ttc | tcc | tcc | cag | atc | cac | aac | 1900 |
| Pro | Tyr | Gly | His | Arg | Arg | Leu | Leu | Arg | Phe | Ser | Ser | Gln | Ile | His | Asn |  |
|  |  |  |  | 575 |  |  |  |  | 580 |  |  |  |  | 585 |  |  |
| ctg | gga | cga | gct | gac | ttc | agg | ccc | aag | gct | ggg | cgc | cac | tcc | tgg | gtg | 1948 |
| Leu | Gly | Arg | Ala | Asp | Phe | Arg | Pro | Lys | Ala | Gly | Arg | His | Ser | Trp | Val |  |
|  |  |  | 590 |  |  |  | 595 |  |  |  | 600 |  |  |  |  |  |
| tgg | cac | gag | tgc | cat | ggg | cat | tac | cac | agc | atg | gac | atc | ttc | act | cac | 1996 |
| Trp | His | Glu | Cys | His | Gly | His | Tyr | His | Ser | Met | Asp | Ile | Phe | Thr | His |  |
|  | 605 |  |  |  |  | 610 |  |  |  |  | 615 |  |  |  |  |  |
| tat | gat | atc | ctc | acc | cca | aat | ggc | acc | aag | gtg | gct | gag | ggc | cac | aaa | 2044 |
| Tyr | Asp | Ile | Leu | Thr | Pro | Asn | Gly | Thr | Lys | Val | Ala | Glu | Gly | His | Lys |  |
|  | 620 |  |  |  |  | 625 |  |  |  |  | 630 |  |  |  |  |  |
| gct | agt | ttc | tgt | ctc | gaa | gac | act | gag | tgt | cag | gag | gat | gtc | tcc | aag | 2092 |
| Ala | Ser | Phe | Cys | Leu | Glu | Asp | Thr | Glu | Cys | Gln | Glu | Asp | Val | Ser | Lys |  |
| 635 |  |  |  |  | 640 |  |  |  |  | 645 |  |  |  |  | 650 |  |
| cgg | tat | gag | tgt | gcc | aac | ttt | gga | gag | caa | ggc | atc | act | gtg | ggt | tgc | 2140 |
| Arg | Tyr | Glu | Cys | Ala | Asn | Phe | Gly | Glu | Gln | Gly | Ile | Thr | Val | Gly | Cys |  |
|  |  |  | 655 |  |  |  |  | 660 |  |  |  |  | 665 |  |  |  |
| tgg | gat | ctc | tac | cgg | cat | gac | att | gac | tgt | cag | tgg | att | gac | atc | acg | 2188 |
| Trp | Asp | Leu | Tyr | Arg | His | Asp | Ile | Asp | Cys | Gln | Trp | Ile | Asp | Ile | Thr |  |
|  |  | 670 |  |  |  |  | 675 |  |  |  |  | 680 |  |  |  |  |
| gat | gtg | aag | cca | gga | aac | tac | att | ctc | cag | gtt | gtc | atc | aac | cca | aac | 2236 |
| Asp | Val | Lys | Pro | Gly | Asn | Tyr | Ile | Leu | Gln | Val | Val | Ile | Asn | Pro | Asn |  |
|  |  | 685 |  |  |  |  | 690 |  |  |  |  | 695 |  |  |  |  |
| ttt | gaa | gta | gca | gag | agt | gac | ttt | acc | aac | aat | gca | atg | aaa | tgt | aac | 2284 |
| Phe | Glu | Val | Ala | Glu | Ser | Asp | Phe | Thr | Asn | Asn | Ala | Met | Lys | Cys | Asn |  |
|  | 700 |  |  |  |  | 705 |  |  |  |  | 710 |  |  |  |  |  |
| tgc | aaa | tat | gat | gga | cat | aga | atc | tgg | gtg | cac | aac | tgc | cac | att | ggt | 2332 |
| Cys | Lys | Tyr | Asp | Gly | His | Arg | Ile | Trp | Val | His | Asn | Cys | His | Ile | Gly |  |
| 715 |  |  |  |  | 720 |  |  |  |  | 725 |  |  |  |  | 730 |  |
| gat | gcc | ttc | agt | gaa | gag | gcc | aac | agg | agg | ttt | gaa | cgc | tac | cct | ggc | 2380 |
| Asp | Ala | Phe | Ser | Glu | Glu | Ala | Asn | Arg | Arg | Phe | Glu | Arg | Tyr | Pro | Gly |  |
|  |  |  |  | 735 |  |  |  |  | 740 |  |  |  |  | 745 |  |  |
| cag | acc | agc | aac | cag | att | atc | taagtgccac | tgccctctgc | aaaccaccac |  |  |  |  |  |  | 2431 |

-continued

Gln Thr Ser Asn Gln Ile Ile
            750

```
tggcccctaa tggcaggggt ctgaggctgc cattacctca ggagcttacc aagaaaccca   2491
tgtcagcaac cgcactcatc agaccatgca ctatggatgt ggaactgtca agcagaagtt   2551
ttcaccctcc ttcagaggcc agctgtcagt atctgtagcc aagcatggga atctttgctc   2611
ccaggcccag caccgagcag aacagaccag agcccaccac accacaaaga gcagcacctg   2671
actaactgcc cacaaaagat ggcagcagct cattttcttt aataggaggt caggatggtc   2731
agctccagta tctcccctaa gtttaggggg atacagcttt acctctagcc ttttggtggg   2791
ggaaaagatc cagccctccc acctcatttt ttactataat atgttgctag gtataatttt   2851
attttatata aaagtgtttt ctgtgattct tcagaaaaaa aaaaaaaaa aaaaaaaaa    2911 aaaaaaaaa                                                            2920
```

<210> SEQ ID NO 2
<211> LENGTH: 753
<212> TYPE: PRT
<213> ORGANISM: Homo sapiens

<400> SEQUENCE: 2

Met Arg Pro Val Ser Val Trp Gln Trp Ser Pro Trp Gly Leu Leu Leu
 1               5                  10                  15

Cys Leu Leu Cys Ser Ser Cys Leu Gly Ser Pro Ser Pro Ser Thr Gly
                20                  25                  30

Pro Glu Lys Lys Ala Gly Ser Gln Gly Leu Arg Phe Arg Leu Ala Gly
            35                  40                  45

Phe Pro Arg Lys Pro Tyr Glu Gly Arg Val Glu Ile Gln Arg Ala Gly
        50                  55                  60

Glu Trp Gly Thr Ile Cys Asp Asp Phe Thr Leu Gln Ala Ala His
 65                  70                  75                  80

Ile Leu Cys Arg Glu Leu Gly Phe Thr Glu Ala Thr Gly Trp Thr His
                85                  90                  95

Ser Ala Lys Tyr Gly Pro Gly Thr Gly Arg Ile Trp Leu Asp Asn Leu
            100                 105                 110

Ser Cys Ser Gly Thr Glu Gln Ser Val Thr Glu Cys Ala Ser Arg Gly
        115                 120                 125

Trp Gly Asn Ser Asp Cys Thr His Asp Glu Asp Ala Gly Val Ile Cys
    130                 135                 140

Lys Asp Gln Arg Leu Pro Gly Phe Ser Asp Ser Asn Val Ile Glu Val
145                 150                 155                 160

Glu His His Leu Gln Val Glu Glu Val Arg Ile Arg Pro Ala Val Gly
                165                 170                 175

Trp Gly Arg Arg Pro Leu Pro Val Thr Glu Gly Leu Val Glu Val Arg
            180                 185                 190

Leu Pro Asp Gly Trp Ser Gln Val Cys Asp Lys Gly Trp Ser Ala His
        195                 200                 205

Asn Ser His Val Val Cys Gly Met Leu Gly Phe Pro Ser Glu Lys Arg
    210                 215                 220

Val Asn Ala Ala Phe Tyr Arg Leu Leu Ala Gln Arg Gln Gln His Ser
225                 230                 235                 240

Phe Gly Leu His Gly Val Ala Cys Val Gly Thr Glu Ala His Leu Ser
                245                 250                 255

Leu Cys Ser Leu Glu Phe Tyr Arg Ala Asn Asp Thr Ala Arg Cys Pro
            260                 265                 270

-continued

```
Gly Gly Gly Pro Ala Val Val Ser Cys Val Pro Gly Pro Val Tyr Ala
            275                 280                 285
Ala Ser Ser Gly Gln Lys Lys Gln Gln Gln Ser Lys Pro Gln Gly Glu
290                 295                 300
Ala Arg Val Arg Leu Lys Gly Ala His Pro Gly Glu Gly Arg Val
305                 310                 315                 320
Glu Val Leu Lys Ala Ser Thr Trp Gly Thr Val Cys Asp Arg Lys Trp
                325                 330                 335
Asp Leu His Ala Ala Ser Val Val Cys Arg Glu Leu Gly Phe Gly Ser
            340                 345                 350
Ala Arg Glu Ala Leu Ser Gly Ala Arg Met Gly Gln Gly Met Gly Ala
            355                 360                 365
Ile His Leu Ser Glu Val Arg Cys Ser Gly Gln Glu Leu Ser Leu Trp
    370                 375                 380
Lys Cys Pro His Lys Asn Ile Thr Ala Glu Asp Cys Ser His Ser Gln
385                 390                 395                 400
Asp Ala Gly Val Arg Cys Asn Leu Pro Tyr Thr Gly Ala Glu Thr Arg
                405                 410                 415
Ile Arg Leu Ser Gly Gly Arg Ser Gln His Glu Gly Arg Val Glu Val
            420                 425                 430
Gln Ile Gly Gly Pro Gly Pro Leu Arg Trp Gly Leu Ile Cys Gly Asp
    435                 440                 445
Asp Trp Gly Thr Leu Glu Ala Met Val Ala Cys Arg Gln Leu Gly Leu
            450                 455                 460
Gly Tyr Ala Asn His Gly Leu Gln Glu Thr Trp Tyr Trp Asp Ser Gly
465                 470                 475                 480
Asn Ile Thr Glu Val Val Met Ser Gly Val Arg Cys Thr Gly Thr Glu
                485                 490                 495
Leu Ser Leu Asp Gln Cys Ala His His Gly Thr His Ile Thr Cys Lys
            500                 505                 510
Arg Thr Gly Thr Arg Phe Thr Ala Gly Val Ile Cys Ser Glu Thr Ala
        515                 520                 525
Ser Asp Leu Leu Leu His Ser Ala Leu Val Gln Glu Thr Ala Tyr Ile
530                 535                 540
Glu Asp Arg Pro Leu His Met Leu Tyr Cys Ala Ala Glu Glu Asn Cys
545                 550                 555                 560
Leu Ala Ser Ser Ala Arg Ser Ala Asn Trp Pro Tyr Gly His Arg Arg
                565                 570                 575
Leu Leu Arg Phe Ser Ser Gln Ile His Asn Leu Gly Arg Ala Asp Phe
            580                 585                 590
Arg Pro Lys Ala Gly Arg His Ser Trp Val Trp His Glu Cys His Gly
        595                 600                 605
His Tyr His Ser Met Asp Ile Phe Thr His Tyr Asp Ile Leu Thr Pro
    610                 615                 620
Asn Gly Thr Lys Val Ala Glu Gly His Lys Ala Ser Phe Cys Leu Glu
625                 630                 635                 640
Asp Thr Glu Cys Gln Glu Asp Val Ser Lys Arg Tyr Glu Cys Ala Asn
                645                 650                 655
Phe Gly Glu Gln Gly Ile Thr Val Gly Cys Trp Asp Leu Tyr Arg His
            660                 665                 670
Asp Ile Asp Cys Gln Trp Ile Asp Ile Thr Asp Val Lys Pro Gly Asn
        675                 680                 685
```

-continued

Tyr Ile Leu Gln Val Val Ile Asn Pro Asn Phe Glu Val Ala Glu Ser
    690             695             700

Asp Phe Thr Asn Asn Ala Met Lys Cys Asn Cys Lys Tyr Asp Gly His
705             710             715             720

Arg Ile Trp Val His Asn Cys His Ile Gly Asp Ala Phe Ser Glu Glu
            725             730             735

Ala Asn Arg Arg Phe Glu Arg Tyr Pro Gly Gln Thr Ser Asn Gln Ile
        740             745             750

Ile

<210> SEQ ID NO 3
<211> LENGTH: 2262
<212> TYPE: DNA
<213> ORGANISM: Homo sapiens

<400> SEQUENCE: 3

| | | | | | |
|---|---|---|---|---|---|
| atgcgacctg | tcagtgtctg | gcagtggagc | ccctgggggc | tgctgctgtg | cctgctgtgc | 60 |
| agttcgtgct | ggggtctcc | gtccccttcc | acgggccctg | agaagaaggc | cgggagccag | 120 |
| gggcttcggt | tccggctggc | tggcttcccc | aggaagcccg | acgagggccg | cgtggagata | 180 |
| cagcgagctg | gtgaatgggg | caccatctgc | gatgatgact | tcacgctgca | ggctgcccac | 240 |
| atcctctgcc | gggagctggg | cttcacagag | gccacaggct | ggacccacag | tgccaaatat | 300 |
| ggccctggaa | caggccgcat | ctggctggac | aacttgagct | gcagtgggac | cgagcagagt | 360 |
| gtgactgaat | gtgcctcccg | gggctggggg | aacagtgact | gtacgcacga | tgaggatgct | 420 |
| ggggtcatct | gcaaagacca | gcgcctccct | ggcttctcgg | actccaatgt | cattgaggta | 480 |
| gagcatcacc | tgcaagtgga | ggaggtgcga | attcgacccg | ccgttgggtg | gggcagacga | 540 |
| cccctgcccg | tgacggaggg | gctggtggaa | gtcaggcttc | ctgacggctg | gtcgcaagtg | 600 |
| tgcgacaaag | gctggagcgc | ccacaacagc | cacgtggtct | gcgggatgct | gggcttcccc | 660 |
| agcgaaaaga | gggtcaacgc | ggccttctac | aggctgctag | cccaacggca | gcaacactcc | 720 |
| tttggtctgc | atgggggtgg | cgtgcgtggc | acggaggccc | acctctccct | ctgttccctg | 780 |
| gagttctatc | gtgccaatga | caccgccagg | tgccctgggg | ggggccctgc | agtggtgagc | 840 |
| tgtgtgccag | gccctgtcta | cgcggcatcc | agtggccaga | agaagcaaca | acagtcgaag | 900 |
| cctcagggg | aggcccgtgt | ccgtctaaag | gcggcgccc | accctggaga | gggccgggta | 960 |
| gaagtcctga | aggccagcac | atggggcaca | gtctgtgacc | gcaagtggga | cctgcatgca | 1020 |
| gccagcgtgg | tgtgtcggga | gctgggcttc | gggagtgctc | gagaagctct | gagtggcgct | 1080 |
| cgcatggggc | agggcatggg | tgctatccac | ctgagtgaag | ttcgctgctc | tggacaggag | 1140 |
| ctctcccct | ggaagtgccc | ccacaagaac | atcacagctg | aggattgttc | acatagccag | 1200 |
| gatgccgggg | tccggtgcaa | cctaccttac | actggggcag | agaccaggat | ccgactcagt | 1260 |
| gggggccgca | gccaacatga | ggggcgagtc | gaggtgcaaa | tagggggacc | tgggccccttt | 1320 |
| cgctggggcc | tcatctgtgg | ggatgactgg | gggaccctgg | aggccatggt | ggcctgtagg | 1380 |
| caactgggtc | tgggctacgc | caaccacggc | ctgcaggaga | cctggtactg | ggactctggg | 1440 |
| aatataacag | aggtggtgat | gagtggagtg | cgctgcacag | ggactgagct | gtccctggat | 1500 |
| cagtgtgccc | atcatggcac | ccacatcacc | tgcaagagga | cagggacccg | cttcactgct | 1560 |
| ggagtcatct | gttctgagac | tgcatcagat | ctgttgctgc | actcagcact | ggtgcaggag | 1620 |
| accgcctaca | tcgaagaccg | gcccctgcat | atgttgtact | gtgctgcgga | agagaactgc | 1680 |
| ctggccagct | cagcccgctc | agccaactgg | ccctatggtc | accggcgtct | gctccgattc | 1740 |

-continued

```
tcctcccaga tccacaacct gggacgagct gacttcaggc ccaaggctgg gcgccactcc      1800
tgggtgtggc acgagtgcca tgggcattac cacagcatgg acatcttcac tcactatgat      1860
atcctcaccc caaatggcac caaggtggct gagggccaca agctagttt ctgtctcgaa       1920 gacactgagt gtcaggagga tgtctccaag cggtatgagt gtgccaactt tggagagcaa     1980
ggcatcactg tgggttgctg ggatctctac cggcatgaca ttgactgtca gtggattgac     2040
atcacggatg tgaagccagg aaactacatt ctccaggttg tcatcaaccc aaactttgaa    2100
gtagcagaga gtgactttac caacaatgca atgaaatgta actgcaaata tgatggacat    2160
agaatctggg tgcacaactg ccacattggt gatgccttca gtgaagaggc caacaggagg   2220
tttgaacgct accctggcca gaccagcaac cagattatct aa                         2262
```

<210> SEQ ID NO 4
<211> LENGTH: 38
<212> TYPE: PRT
<213> ORGANISM: Artificial Sequence
<220> FEATURE:
<223> OTHER INFORMATION: Description of Artificial Sequence:SRRD
      signature (consensus sequence)
<220> FEATURE:
<223> OTHER INFORMATION: Xaas at positions 2-6,8,9,11-16,19,20,22-33,and
      35-37 are any amino acid

<400> SEQUENCE: 4

Gly Xaa Xaa Xaa Xaa Gly Xaa Xaa Glu Xaa Xaa Xaa Xaa Xaa Xaa
 1               5                  10                  15

Trp Gly Xaa Xaa Cys Xaa Xaa Xaa Xaa Xaa Xaa Xaa Xaa Xaa Xaa
                20                  25                  30

Xaa Cys Xaa Xaa Xaa Gly
            35

<210> SEQ ID NO 5
<211> LENGTH: 417
<212> TYPE: PRT
<213> ORGANISM: Homo sapiens

<400> SEQUENCE: 5

Met Arg Phe Ala Trp Thr Val Leu Leu Leu Gly Pro Leu Gln Leu Cys
 1               5                  10                  15

Ala Leu Val His Cys Ala Pro Pro Ala Ala Gly Gln Gln Gln Pro Pro
                20                  25                  30

Arg Glu Pro Pro Ala Ala Pro Gly Ala Trp Arg Gln Gln Ile Gln Trp
            35                  40                  45

Glu Asn Asn Gly Gln Val Phe Ser Leu Leu Ser Leu Gly Ser Gln Tyr
        50                  55                  60

Gln Pro Gln Arg Arg Arg Asp Pro Gly Ala Ala Val Pro Gly Ala Ala
 65                 70                  75                  80

Asn Ala Ser Ala Gln Gln Pro Arg Thr Pro Ile Leu Leu Ile Arg Asp
                85                  90                  95

Asn Arg Thr Ala Ala Gly Arg Thr Arg Thr Ala Gly Ser Ser Gly Val
            100                 105                 110

Thr Ala Gly Arg Pro Arg Pro Thr Ala Arg His Trp Phe Gln Ala Gly
        115                 120                 125

Tyr Ser Thr Ser Arg Ala Arg Glu Ala Gly Pro Ser Arg Ala Glu Asn
    130                 135                 140

Gln Thr Ala Pro Gly Glu Val Pro Ala Leu Ser Asn Leu Arg Pro Pro
145                 150                 155                 160

```
Ser Arg Val Asp Gly Met Val Gly Asp Pro Tyr Asn Pro Tyr Lys
            165                 170                 175

Tyr Ser Asp Asp Asn Pro Tyr Asn Tyr Tyr Asp Thr Tyr Glu Arg
            180                 185                 190

Pro Arg Pro Gly Gly Arg Tyr Arg Pro Gly Tyr Gly Thr Gly Tyr Phe
            195                 200                 205

Gln Tyr Gly Leu Pro Asp Leu Val Ala Asp Pro Tyr Tyr Ile Gln Ala
            210                 215                 220

Ser Thr Tyr Val Gln Lys Met Ser Met Tyr Asn Leu Arg Cys Ala Ala
225                 230                 235                 240

Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
            260                 265                 270

Gly Thr Ser Asp Phe Leu Pro Ser Arg Pro Arg Tyr Ser Trp Glu Trp
            275                 280                 285

His Ser Cys His Gln His Tyr His Ser Met Asp Glu Phe Ser His Tyr
            290                 295                 300

Asp Leu Leu Asp Ala Asn Thr Gln Arg Arg Val Ala Glu Gly His Lys
305                 310                 315                 320

Ala Ser Phe Cys Leu Glu Asp Thr Ser Cys Asp Tyr Gly Tyr His Arg
                325                 330                 335

Arg Phe Ala Cys Thr Ala His Thr Gln Gly Leu Ser Pro Gly Cys Tyr
            340                 345                 350

Asp Thr Tyr Gly Ala Asp Ile Asp Cys Gln Trp Ile Asp Ile Thr Asp
            355                 360                 365

Val Lys Pro Gly Asn Tyr Ile Leu Lys Val Ser Val Asn Pro Ser Tyr
            370                 375                 380

Leu Val Pro Glu Ser Asp Tyr Thr Asn Asn Val Val Arg Cys Asp Ile
385                 390                 395                 400

Arg Tyr Thr Gly His His Ala Tyr Ala Ser Gly Cys Thr Ile Ser Pro
                405                 410                 415

Tyr

<210> SEQ ID NO 6
<211> LENGTH: 574
<212> TYPE: PRT
<213> ORGANISM: Homo sapiens

<400> SEQUENCE: 6

Met Ala Leu Ala Arg Gly Ser Arg Gln Leu Gly Ala Leu Val Trp Gly
 1               5                  10                  15

Ala Cys Leu Cys Val Leu Val His Gly Gln Gln Ala Gln Pro Gly Gln
                20                  25                  30

Gly Ser Asp Pro Ala Arg Trp Arg Gln Leu Ile Gln Trp Glu Asn Asn
            35                  40                  45

Gly Gln Val Tyr Ser Leu Leu Asn Ser Gly Ser Glu Tyr Val Pro Ala
        50                  55                  60

Gly Pro Gln Arg Ser Glu Ser Ser Arg Val Leu Leu Ala Gly Ala
65                  70                  75                  80

Pro Gln Ala Gln Gln Arg Arg Ser His Gly Ser Pro Arg Arg Gln
                85                  90                  95

Ala Pro Ser Leu Pro Leu Pro Gly Arg Val Gly Ser Asp Thr Val Arg
            100                 105                 110
```

-continued

```
Gly Gln Ala Arg His Pro Phe Gly Phe Gly Gln Val Pro Asp Asn Trp
        115                 120                 125
Arg Glu Val Ala Val Gly Asp Ser Thr Gly Met Ala Leu Ala Arg Thr
        130                 135                 140
Ser Val Ser Gln Gln Arg His Gly Gly Ser Ala Ser Ser Val Ser Ala
145                 150                 155                 160
Ser Ala Phe Ala Ser Thr Tyr Arg Gln Gln Pro Ser Tyr Pro Gln Gln
                165                 170                 175
Phe Pro Tyr Pro Gln Ala Pro Phe Val Ser Gln Tyr Glu Asn Tyr Asp
                180                 185                 190
Pro Ala Ser Arg Thr Tyr Asp Gln Gly Phe Val Tyr Tyr Arg Pro Ala
                195                 200                 205
Gly Gly Gly Val Gly Ala Gly Ala Ala Val Ala Ser Ala Gly Val
        210                 215                 220
Ile Tyr Pro Tyr Gln Pro Arg Ala Arg Tyr Glu Glu Tyr Gly Gly Gly
225                 230                 235                 240
Glu Glu Leu Pro Glu Tyr Pro Gln Gly Phe Tyr Pro Ala Pro Glu
                245                 250                 255
Arg Pro Tyr Val Pro Pro Pro Pro Pro Asp Gly Leu Asp Arg
                260                 265                 270
Arg Tyr Ser His Ser Leu Tyr Ser Glu Gly Thr Pro Gly Phe Glu Gln
                275                 280                 285
Ala Tyr Pro Asp Pro Gly Pro Glu Ala Ala Gln Ala His Gly Gly Asp
        290                 295                 300
Pro Arg Leu Gly Trp Tyr Pro Tyr Ala Asn Pro Pro Glu Ala
305                 310                 315                 320
Tyr Gly Pro Pro Arg Ala Leu Glu Pro Pro Tyr Leu Pro Val Arg Ser
                325                 330                 335
Ser Asp Thr Pro Pro Gly Gly Glu Arg Asn Gly Ala Gln Gln Gly
                340                 345                 350
Arg Leu Ser Val Gly Ser Val Tyr Arg Pro Asn Gln Asn Gly Arg Gly
        355                 360                 365
Leu Pro Asp Leu Val Pro Asp Pro Asn Tyr Val Gln Ala Ser Thr Tyr
        370                 375                 380
Val Gln Arg Ala His Leu Tyr Ser Leu Arg Cys Ala Ala Glu Glu Lys
385                 390                 395                 400
Cys Leu Ala Ser Thr Ala Tyr Ala Pro Glu Ala Thr Asp Tyr Asp Val
                405                 410                 415
Arg Val Leu Leu Arg Phe Pro Gln Arg Val Lys Asn Gln Gly Thr Ala
        420                 425                 430
Asp Phe Leu Pro Asn Arg Pro Arg His Thr Trp Glu Trp His Ser Cys
        435                 440                 445
His Gln His Tyr His Ser Met Asp Glu Phe Ser His Tyr Asp Leu Leu
        450                 455                 460
Asp Ala Ala Thr Gly Lys Lys Val Ala Glu Gly His Lys Ala Ser Phe
465                 470                 475                 480
Cys Leu Glu Asp Ser Thr Cys Asp Phe Gly Asn Leu Lys Arg Tyr Ala
                485                 490                 495
Cys Thr Ser His Thr Gln Gly Leu Ser Pro Gly Cys Tyr Asp Thr Tyr
                500                 505                 510
Asn Ala Asp Ile Asp Cys Gln Trp Ile Asp Ile Thr Asp Val Gln Pro
        515                 520                 525
```

-continued

```
Gly Asn Tyr Ile Leu Lys Val His Val Asn Pro Lys Tyr Ile Val Leu
    530                 535                 540
Glu Ser Asp Phe Thr Asn Asn Val Val Arg Cys Asn Ile His Tyr Thr
545                 550                 555                 560
Gly Arg Tyr Val Ser Ala Thr Asn Cys Lys Ile Val Gln Ser
                565                 570

<210> SEQ ID NO 7
<211> LENGTH: 774
<212> TYPE: PRT
<213> ORGANISM: Homo sapiens

<400> SEQUENCE: 7

Met Glu Arg Pro Leu Cys Ser His Leu Cys Ser Cys Leu Ala Met Leu
  1               5                  10                  15
Ala Leu Leu Ser Pro Leu Ser Leu Ala Gln Tyr Asp Ser Trp Pro His
                 20                  25                  30
Tyr Pro Glu Tyr Phe Gln Gln Pro Ala Pro Glu Tyr His Gln Pro Gln
             35                  40                  45
Ala Pro Ala Asn Val Ala Lys Ile Gln Leu Arg Leu Ala Gly Gln Lys
         50                  55                  60
Arg Lys His Ser Glu Gly Arg Val Glu Val Tyr Tyr Asp Gly Gln Trp
 65                  70                  75                  80
Gly Thr Val Cys Asp Asp Phe Ser Ile His Ala Ala His Val Val
                 85                  90                  95
Cys Arg Glu Leu Gly Tyr Val Glu Ala Lys Ser Trp Thr Ala Ser Ser
                100                 105                 110
Ser Tyr Gly Lys Gly Glu Gly Pro Ile Trp Leu Asp Asn Leu His Cys
            115                 120                 125
Thr Gly Asn Glu Ala Thr Leu Ala Ala Cys Thr Ser Asn Gly Trp Gly
        130                 135                 140
Val Thr Asp Cys Lys His Thr Glu Asp Val Gly Val Val Cys Ser Asp
145                 150                 155                 160
Lys Arg Ile Pro Gly Phe Lys Phe Asp Asn Ser Leu Ile Asn Gln Ile
                165                 170                 175
Glu Asn Leu Asn Ile Gln Val Glu Asp Ile Arg Ile Arg Ala Ile Leu
            180                 185                 190
Ser Thr Tyr Arg Lys Arg Thr Pro Val Met Glu Gly Tyr Val Glu Val
        195                 200                 205
Lys Glu Gly Lys Thr Trp Lys Gln Ile Cys Asp Lys His Trp Thr Ala
    210                 215                 220
Lys Asn Ser Arg Val Val Cys Gly Met Phe Gly Phe Pro Gly Glu Arg
225                 230                 235                 240
Thr Tyr Asn Thr Lys Val Tyr Lys Met Phe Ala Ser Arg Arg Lys Gln
                245                 250                 255
Arg Tyr Trp Pro Phe Ser Met Asp Cys Thr Gly Thr Glu Ala His Ile
            260                 265                 270
Ser Ser Cys Lys Leu Gly Pro Gln Val Ser Leu Asp Pro Met Lys Asn
        275                 280                 285
Val Thr Cys Glu Asn Gly Leu Pro Ala Val Val Ser Cys Val Pro Gly
    290                 295                 300
Gln Val Phe Ser Pro Asp Gly Pro Ser Arg Phe Arg Lys Ala Tyr Lys
305                 310                 315                 320
Pro Glu Gln Pro Leu Val Arg Leu Arg Gly Gly Ala Tyr Ile Gly Glu
                325                 330                 335
```

-continued

```
Gly Arg Val Glu Val Leu Lys Asn Gly Glu Trp Gly Thr Val Cys Asp
                340                 345                 350
Asp Lys Trp Asp Leu Val Ser Ala Ser Val Val Cys Arg Glu Leu Gly
                355                 360                 365
Phe Gly Ser Ala Lys Glu Ala Val Thr Gly Ser Arg Leu Gly Gln Gly
                370                 375             380
Ile Gly Pro Ile His Leu Asn Glu Ile Gln Cys Thr Gly Asn Glu Lys
385                 390                 395                 400
Ser Ile Ile Asp Cys Lys Phe Asn Ala Glu Ser Gln Gly Cys Asn His
                    405                 410                 415
Glu Glu Asp Ala Gly Val Arg Cys Asn Thr Pro Ala Met Gly Leu Gln
                420                 425                 430
Lys Lys Leu Arg Leu Asn Gly Arg Asn Pro Tyr Glu Gly Arg Val
                435                 440                 445
Glu Val Leu Val Glu Arg Asn Gly Ser Leu Val Trp Gly Met Val Cys
                450                 455                 460
Gly Gln Asn Trp Gly Ile Val Glu Ala Met Val Val Cys Arg Gln Leu
465                 470                 475                 480
Gly Leu Gly Phe Ala Ser Asn Ala Phe Gln Glu Thr Trp Tyr Trp His
                485                 490                 495
Gly Asp Val Asn Ser Asn Lys Val Val Met Ser Gly Val Lys Cys Ser
                500                 505                 510
Gly Thr Glu Leu Ser Leu Ala His Cys Arg His Asp Gly Glu Asp Val
                515                 520                 525
Ala Cys Pro Gln Gly Gly Val Gln Tyr Gly Ala Gly Val Ala Cys Ser
                530                 535                 540
Glu Thr Ala Pro Asp Leu Val Leu Asn Ala Glu Met Val Gln Gln Thr
545                 550                 555                 560
Thr Tyr Leu Glu Asp Arg Pro Met Phe Met Leu Gln Cys Ala Met Glu
                565                 570                 575
Glu Asn Cys Leu Ser Ala Ser Ala Ala Gln Thr Asp Pro Thr Thr Gly
                580                 585                 590
Tyr Arg Arg Leu Leu Arg Phe Ser Ser Gln Ile His Asn Asn Gly Gln
                595                 600                 605
Ser Asp Phe Arg Pro Lys Asn Gly Arg His Ala Trp Ile Trp His Asp
                610                 615                 620
Cys His Arg His Tyr His Ser Met Glu Val Phe Thr His Tyr Asp Leu
625                 630                 635                 640
Leu Asn Leu Asn Gly Thr Lys Val Ala Glu Gly His Lys Ala Ser Phe
                645                 650                 655
Cys Leu Glu Asp Thr Glu Cys Glu Gly Asp Ile Gln Lys Asn Tyr Glu
                660                 665                 670
Cys Ala Asn Phe Gly Asp Gln Gly Ile Thr Met Gly Cys Trp Asp Met
                675                 680                 685
Tyr Arg His Asp Ile Asp Cys Gln Trp Val Asp Ile Thr Asp Val Pro
                690                 695                 700
Pro Gly Asp Tyr Leu Phe Gln Val Val Ile Asn Pro Asn Phe Glu Val
705                 710                 715                 720
Ala Glu Ser Asp Tyr Ser Asn Asn Ile Met Lys Cys Arg Ser Arg Tyr
                725                 730                 735
Asp Gly His Arg Ile Trp Met Tyr Asn Cys His Ile Gly Gly Ser Phe
                740                 745                 750
```

```
Ser Glu Glu Thr Glu Lys Lys Phe Glu His Phe Ser Gly Leu Leu Asn
            755                 760                 765
Asn Gln Leu Ser Pro Gln
            770

<210> SEQ ID NO 8
<211> LENGTH: 754
<212> TYPE: PRT
<213> ORGANISM: murine lysyl oxidase-related protein

<400> SEQUENCE: 8

Met Arg Ala Val Ser Val Trp Tyr Cys Cys Pro Trp Gly Leu Leu Leu
  1               5                  10                  15

Leu His Cys Leu Cys Ser Phe Ser Val Gly Ser Pro Ser Pro Ser Ile
                 20                  25                  30

Ser Pro Glu Lys Lys Val Gly Ser Gln Gly Leu Arg Phe Arg Leu Ala
             35                  40                  45

Gly Phe Pro Arg Lys Pro Tyr Glu Gly Arg Val Glu Ile Gln Arg Ala
         50                  55                  60

Gly Glu Trp Gly Thr Ile Cys Asp Asp Asp Phe Thr Leu Gln Ala Ala
 65                  70                  75                  80

His Val Leu Cys Arg Glu Leu Gly Phe Thr Glu Ala Thr Gly Trp Thr
                 85                  90                  95

His Ser Ala Lys Tyr Gly Pro Gly Thr Gly Arg Ile Trp Leu Asp Asn
                100                 105                 110

Leu Ser Cys Arg Gly Thr Glu Gly Ser Val Thr Glu Cys Ala Ser Arg
            115                 120                 125

Gly Trp Gly Asn Ser Asp Cys Thr His Asp Glu Asp Ala Gly Val Ile
130                 135                 140

Cys Lys Asp Gln Arg Leu Pro Gly Phe Ser Asp Ser Asn Val Ile Glu
145                 150                 155                 160

Val Glu His Gln Leu Gln Val Glu Glu Val Arg Leu Arg Pro Ala Val
                165                 170                 175

Glu Trp Gly Arg Arg Pro Leu Pro Val Thr Glu Gly Leu Val Glu Val
            180                 185                 190

Arg Leu Pro Glu Gly Trp Ser Gln Val Cys Asp Lys Gly Trp Ser Ala
        195                 200                 205

His Asn Ser His Val Val Cys Gly Met Leu Gly Phe Pro Gly Glu Lys
210                 215                 220

Arg Val Asn Met Ala Phe Tyr Arg Met Leu Ala Gln Lys Lys Gln His
225                 230                 235                 240

Ser Phe Gly Leu His Ser Val Ala Cys Val Gly Thr Glu Ala His Leu
                245                 250                 255

Ser Leu Cys Ser Leu Glu Phe Tyr Arg Ala Asn Asp Thr Thr Arg Cys
            260                 265                 270

Ser Gly Gly Asn Pro Ala Val Val Ser Cys Val Leu Gly Pro Leu Tyr
        275                 280                 285

Ala Thr Phe Thr Gly Gln Lys Lys Gln His Ser Lys Pro Gln Gly
        290                 295                 300

Glu Ala Arg Val Arg Leu Lys Gly Gly Ala His Gln Gly Glu Gly Arg
305                 310                 315                 320

Val Glu Val Leu Lys Ala Gly Thr Trp Gly Thr Val Cys Asp Arg Lys
                325                 330                 335

Trp Asp Leu Gln Ala Ala Ser Val Val Cys Pro Glu Leu Gly Phe Gly
            340                 345                 350
```

```
Thr Ala Arg Glu Ala Leu Ser Gly Ala Arg Met Gly Gln Gly Met Gly
        355                 360                 365

Ala Ile His Leu Ser Glu Val Arg Cys Ser Gly Gln Glu Pro Ser Leu
        370                 375                 380

Trp Arg Cys Pro Ser Lys Asn Ile Thr Ala Glu Asp Cys Ser His Ser
385                 390                 395                 400

Gln Asp Ala Gly Val Arg Cys Asn Leu Pro Tyr Thr Gly Val Glu Thr
                405                 410                 415

Lys Ile Arg Leu Ser Gly Gly Arg Ser Arg Tyr Glu Gly Arg Val Glu
        420                 425                 430

Val Gln Ile Gly Ile Pro Gly His Leu Arg Trp Gly Leu Ile Cys Gly
        435                 440                 445

Asp Asp Trp Gly Thr Leu Glu Ala Met Val Ala Cys Arg Gln Leu Gly
        450                 455                 460

Leu Gly Tyr Ala Asn His Gly Leu Gln Glu Thr Trp Tyr Trp Asp Ser
465                 470                 475                 480

Gly Asn Val Thr Glu Val Val Met Ser Gly Val Arg Cys Thr Gly Ser
                485                 490                 495

Glu Leu Ser Leu Asn Gln Cys Ala His His Ser Ser His Ile Thr Cys
                500                 505                 510

Lys Lys Thr Gly Thr Arg Phe Thr Ala Gly Val Ile Cys Ser Glu Thr
        515                 520                 525

Ala Ser Asp Leu Leu His Ser Ala Leu Val Gln Glu Thr Ala Tyr
        530                 535                 540

Ile Glu Asp Arg Pro Leu His Met Leu Tyr Cys Ala Ala Glu Glu Asn
545                 550                 555                 560

Cys Leu Ala Ser Ser Ala Arg Ser Ala Asn Trp Pro Tyr Gly His Arg
                565                 570                 575

Arg Leu Leu Arg Phe Ser Ser Gln Ile His Asn Leu Gly Arg Ala Asp
                580                 585                 590

Phe Arg Pro Lys Ala Gly Arg His Ser Trp Val Trp His Glu Cys His
        595                 600                 605

Gly His Tyr His Ser Met Asp Ile Phe Thr His Tyr Asp Ile Leu Thr
        610                 615                 620

Pro Asn Gly Thr Lys Val Ala Glu Gly His Lys Ala Ser Phe Cys Leu
625                 630                 635                 640

Glu Asp Thr Glu Cys Gln Glu Asp Val Ser Lys Arg Tyr Glu Cys Ala
                645                 650                 655

Asn Phe Gly Glu Gln Gly Ile Thr Val Gly Cys Trp Asp Leu Tyr Arg
                660                 665                 670

His Asp Ile Asp Cys Gln Trp Ile Asp Ile Thr Asp Val Lys Pro Gly
        675                 680                 685

Asn Tyr Ile Leu Gln Val Val Ile Asn Pro Asn Phe Glu Val Ala Glu
        690                 695                 700

Ser Asp Phe Thr Asn Asn Ala Met Lys Cys Asn Cys Lys Tyr Asp Gly
705                 710                 715                 720

His Arg Ile Trp Val His Asn Cys His Ile Gly Asp Ala Phe Ser Glu
                725                 730                 735

Glu Ala Asn Arg Arg Phe Glu Arg Tyr Pro Gly Gln Thr Ser Asn Gln
                740                 745                 750

Ile Val
```

-continued

```
<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Copper
      talon consensus sequence

<400> SEQUENCE: 9

Trp Glu Trp His Ser Cys His Gln His Tyr His
  1               5                  10

<210> SEQ ID NO 10
<211> LENGTH: 451
<212> TYPE: PRT
<213> ORGANISM: Homo sapiens

<400> SEQUENCE: 10

Met Glu Gln Trp Asp His Phe His Asn Gln Gln Glu Asp Thr Asp Ser
  1               5                  10                  15

Cys Ser Glu Ser Val Lys Phe Asp Ala Arg Ser Met Thr Ala Leu Leu
                 20                  25                  30

Pro Pro Asn Pro Lys Asn Ser Pro Ser Leu Gln Glu Lys Leu Lys Ser
             35                  40                  45

Phe Lys Ala Ala Leu Ile Ala Leu Tyr Leu Leu Val Phe Ala Val Leu
 50                  55                  60

Ile Pro Leu Ile Gly Ile Val Ala Ala Gln Leu Leu Lys Trp Glu Thr
 65                  70                  75                  80

Lys Asn Cys Ser Val Ser Ser Thr Asn Ala Asn Asp Ile Thr Gln Ser
                 85                  90                  95

Leu Thr Gly Lys Gly Asn Asp Ser Glu Glu Met Arg Phe Gln Glu
            100                 105                 110

Val Phe Met Glu His Met Ser Asn Met Glu Lys Arg Ile Gln His Ile
            115                 120                 125

Leu Asp Met Glu Ala Asn Leu Met Asp Thr Glu His Phe Gln Asn Phe
        130                 135                 140

Ser Met Thr Thr Asp Gln Arg Phe Asn Asp Ile Leu Leu Gln Leu Ser
145                 150                 155                 160

Thr Leu Phe Ser Ser Val Gln Gly His Gly Asn Ala Ile Asp Glu Ile
                165                 170                 175

Ser Lys Ser Leu Ile Ser Leu Asn Thr Thr Leu Leu Asp Leu Gln Leu
            180                 185                 190

Asn Ile Glu Asn Leu Asn Gly Lys Ile Gln Glu Asn Thr Phe Lys Gln
        195                 200                 205

Gln Glu Glu Ile Ser Lys Leu Glu Glu Arg Val Tyr Asn Val Ser Ala
    210                 215                 220

Glu Ile Met Ala Met Lys Glu Glu Gln Val His Leu Glu Gln Glu Ile
225                 230                 235                 240

Lys Gly Glu Val Lys Val Leu Asn Asn Ile Thr Asn Asp Leu Arg Leu
                245                 250                 255

Lys Asp Trp Glu His Ser Gln Thr Leu Arg Asn Ile Thr Leu Ile Gln
            260                 265                 270

Gly Pro Pro Gly Pro Gly Lys Gly Asp Arg Gly Pro Thr Gly
        275                 280                 285

Glu Ser Gly Pro Arg Gly Phe Pro Gly Pro Ile Gly Pro Gly Leu
    290                 295                 300

Lys Gly Asp Arg Gly Ala Ile Gly Phe Pro Gly Ser Arg Gly Leu Pro
```

```
305                 310                 315                 320
Gly Tyr Ala Gly Arg Pro Gly Asn Ser Gly Pro Lys Gly Gln Lys Gly
                325                 330                 335

Glu Lys Gly Ser Gly Asn Thr Leu Thr Pro Phe Thr Lys Val Arg Leu
            340                 345                 350

Val Gly Gly Ser Gly Pro His Glu Gly Arg Val Glu Ile Leu His Ser
            355                 360                 365

Gly Gln Trp Gly Thr Ile Cys Asp Asp Arg Trp Glu Val Arg Val Gly
        370                 375                 380

Gln Val Val Cys Arg Ser Leu Gly Tyr Pro Gly Val Gln Ala Val His
385                 390                 395                 400

Lys Ala Ala His Phe Gly Gln Gly Thr Gly Pro Ile Trp Leu Asn Glu
                405                 410                 415

Val Phe Cys Phe Gly Arg Glu Ser Ser Ile Glu Glu Cys Lys Ile Arg
                420                 425                 430

Gln Trp Gly Thr Arg Ala Cys Ser His Ser Glu Asp Ala Gly Val Thr
            435                 440                 445

Cys Thr Leu
        450

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 11
gcttaccaag aaacccatgt cagc                                          24

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 12
ggcagttagt caggtgctgc                                               20
```